(12) United States Patent
Lyles

(10) Patent No.: US 7,662,767 B2
(45) Date of Patent: Feb. 16, 2010

(54) POLYNUCLEOTIDE INTERCALATOR INTERCEPTORS AND INHIBITORS

(75) Inventor: Mark B. Lyles, Great Lakes, IL (US)

(73) Assignee: Materials Evolution and Development USA, Inc., San Antonio, TX (US)

( * ) Notice: Subject to any disclaimer, the term of this patent is extended or adjusted under 35 U.S.C. 154(b) by 532 days.

(21) Appl. No.: 10/496,909

(22) PCT Filed: Dec. 6, 2001

(86) PCT No.: PCT/US01/46913

§ 371 (c)(1),
(2), (4) Date: May 27, 2004

(87) PCT Pub. No.: WO02/45707

PCT Pub. Date: Jun. 13, 2002

(65) Prior Publication Data

US 2005/0065335 A1  Mar. 24, 2005

Related U.S. Application Data

(60) Provisional application No. 60/251,906, filed on Dec. 6, 2000.

(51) Int. Cl.
*A01N 61/00* (2006.01)
*A01K 38/00* (2006.01)
*A61K 51/00* (2006.01)
*C12N 11/00* (2006.01)
*A01N 43/04* (2006.01)

(52) U.S. Cl. .............................. 514/1; 514/25; 514/44; 424/1.11; 424/1.65; 435/174

(58) Field of Classification Search ................... 534/1, 534/44; 514/1, 25, 44; 424/1.11, 1.65; 435/174
See application file for complete search history.

(56) References Cited

U.S. PATENT DOCUMENTS 6,822,086 B1 * 11/2004 Papisov .................... 536/24.2

FOREIGN PATENT DOCUMENTS

WO  00/76554 A1  12/2000
WO  93/07883     4/2003

OTHER PUBLICATIONS

Notification of Transmittal of the International PCT Search Report and International PCT Search Report PCT/US01/46913, 10 pages, Jan. 15, 2003.
Traganos, F. et al., "Caffeine Modulates the Effects of DNA-intercalating Drugs in Vitro: a Flow Cytometric and Spectrophotometric Analysis of Caffeine Interaction with Novantrone, Doxorubicin, Ellipticine, and the Doxorubicin Analogue AD198", Abstract, *Cancer Research*, vol. 51, No. 14, XP-002226112, Jul. 15, 1991.
Bedner, E. et al., "Caffeine Dissociates Comlexes between DNA and Intercalating Dyes: Appliaiton for Bleaching Fluorochrome-stained Cells for Their Subsequent Restaining and Analysis by Laser Scanning Cytometry", Abstract, *Cytometry: The Journal of the Society of Analytical Cytology*, vol. 43, No. 1, XP-002226113, Jan. 1, 2001.
Lyles, Mark B., et al., "Caffeine and Other Xanthines as Interceptors and Scavengers of Planar Polyaromatic DNA Intercalators", Proceedings of the American Association for Cancer Research Annual Meeting, No. 41, p. 662, XP-02226111, Mar. 2000.

* cited by examiner

*Primary Examiner*—Jezia Riley
(74) *Attorney, Agent, or Firm*—King & Spalding L.L.P.

(57) ABSTRACT

A method of using modified xanthine molecules as a binding agent is disclosed. Xanthine molecules with at least one substitution of a methyl group at the N1, N3, N7, or N9 position bind to intercalating molecules efficiently. This method can be applied to inhibiting intercalating molecules from binding to nucleic acids, as well as removing intercalating molecules that have been bound to nucleic acids. This method can also be applied to synthesize an efficient drug delivery system for compounds that have low solubility in aqueous media, including anti-neoplastic agents. The method can also be applied to flurosecently labeling nucleic acids.

11 Claims, 26 Drawing Sheets

Fig 2-1
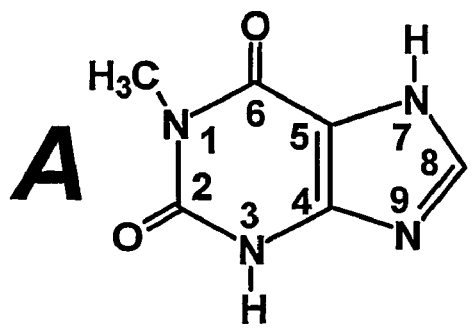
A
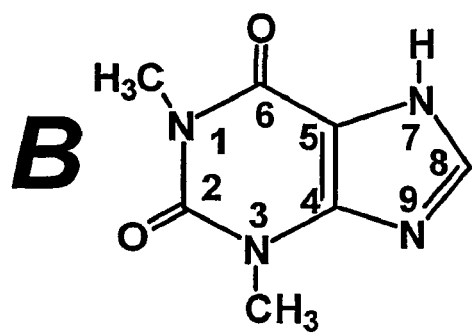
B
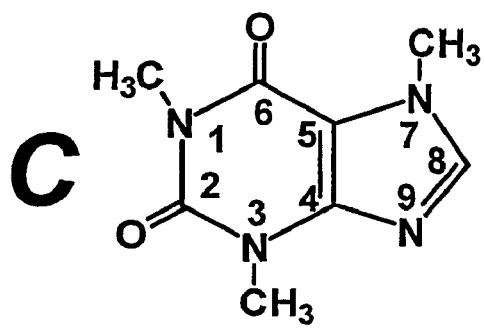
C
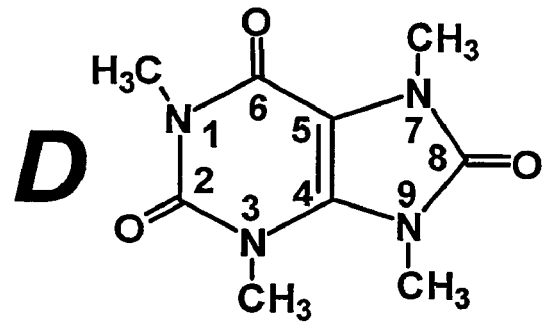
D
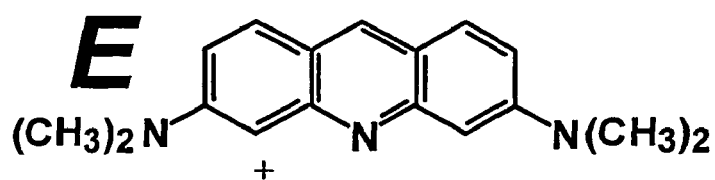
E

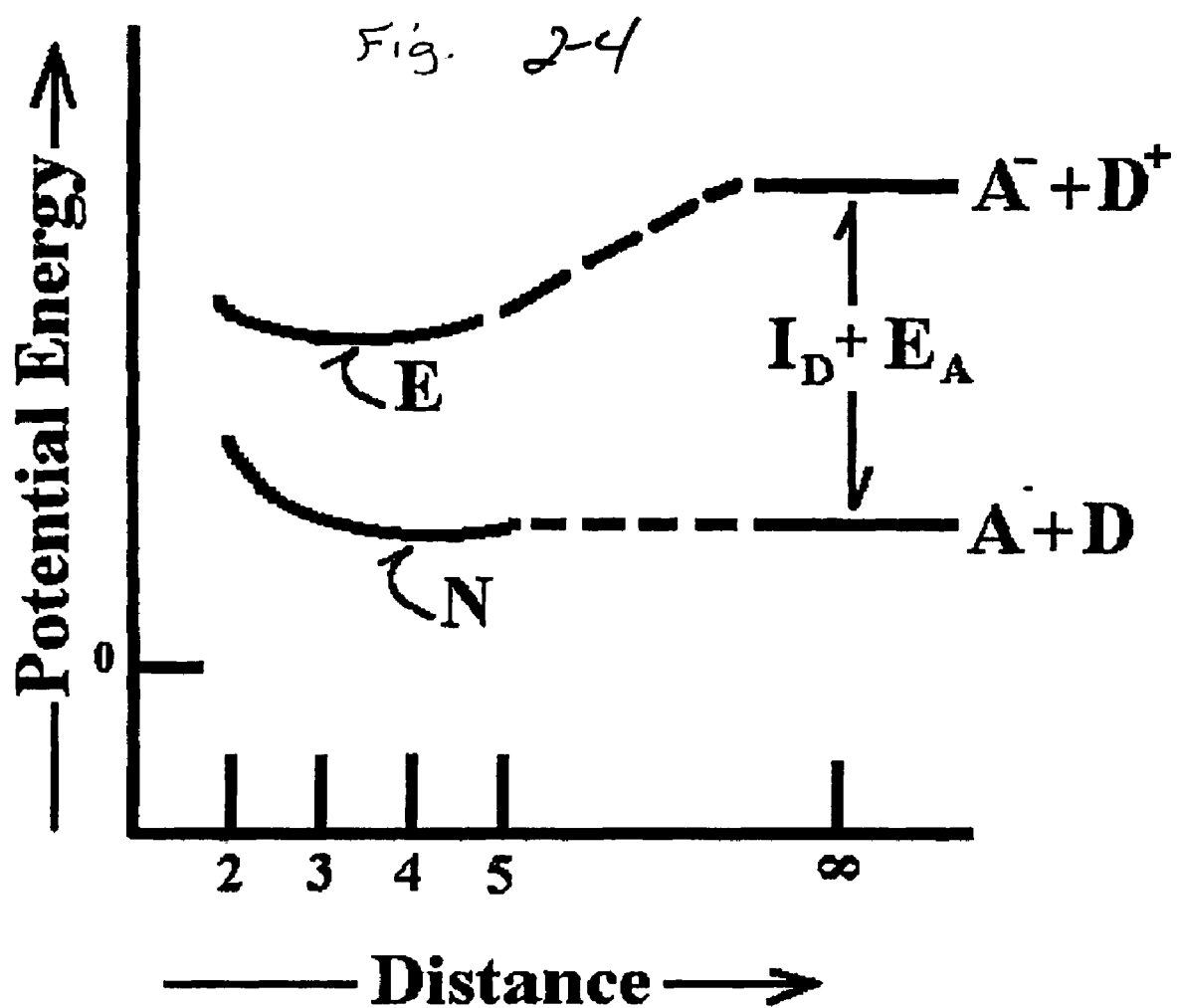

Fig. 3-5
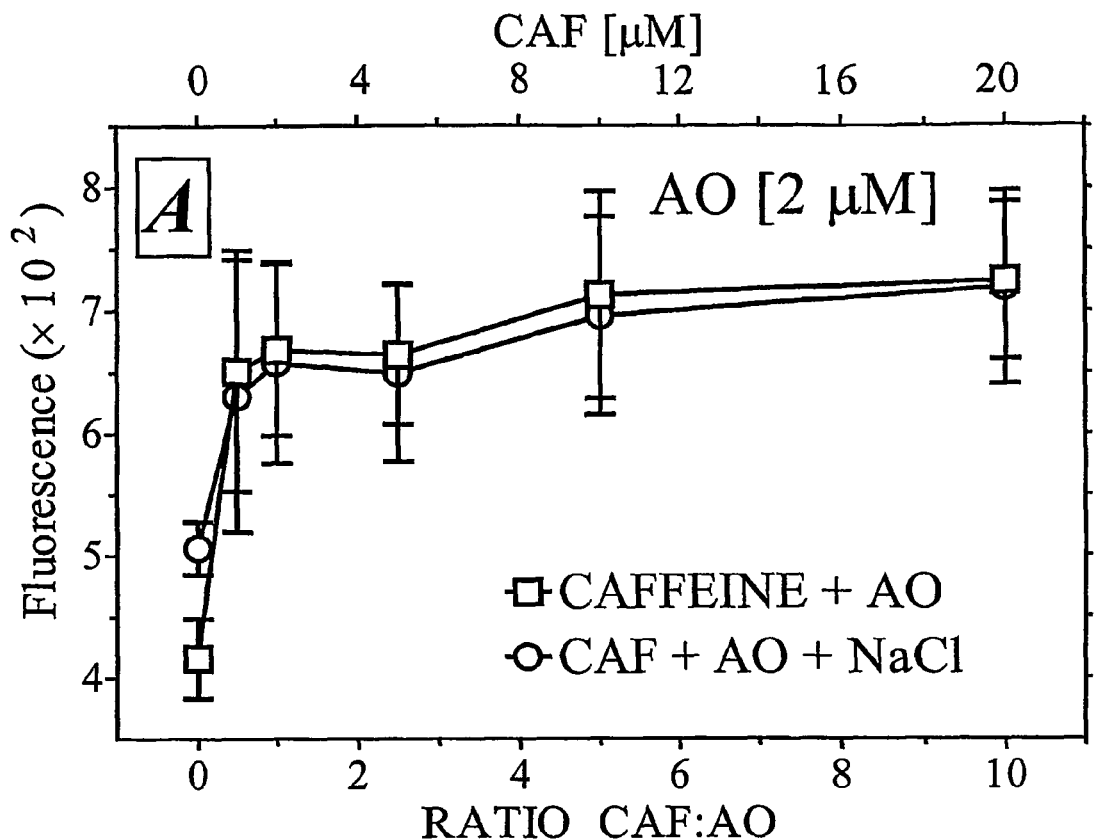
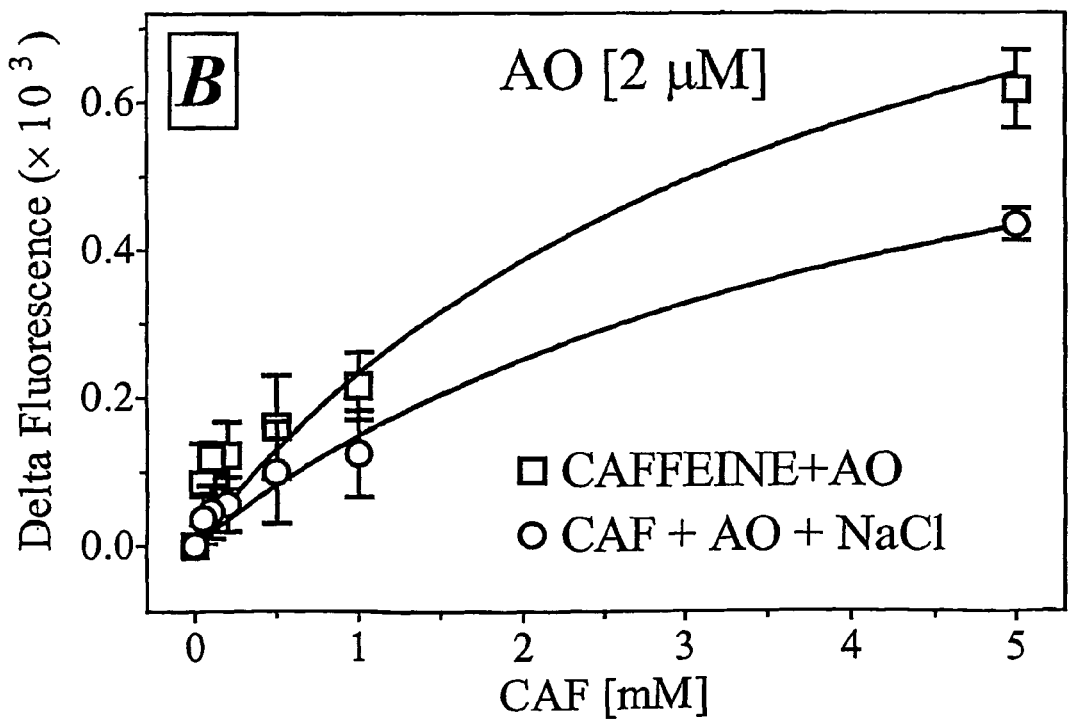

Fig. 4-1
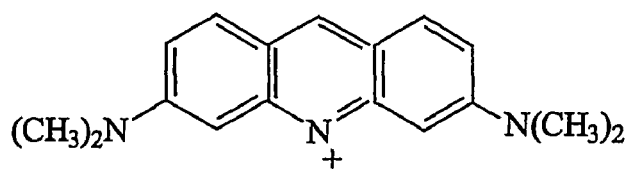
B 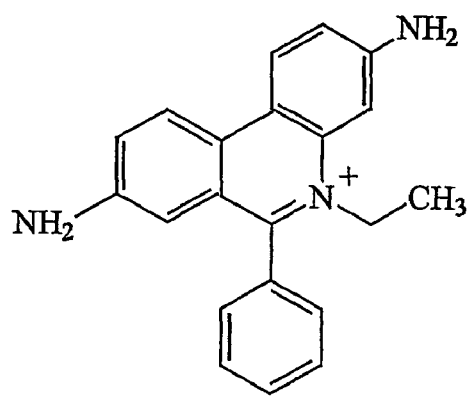
C 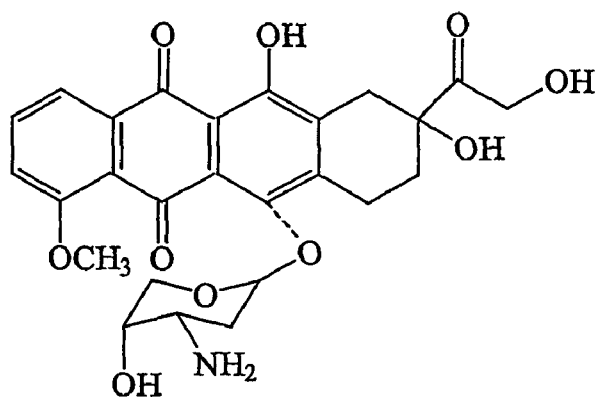
D 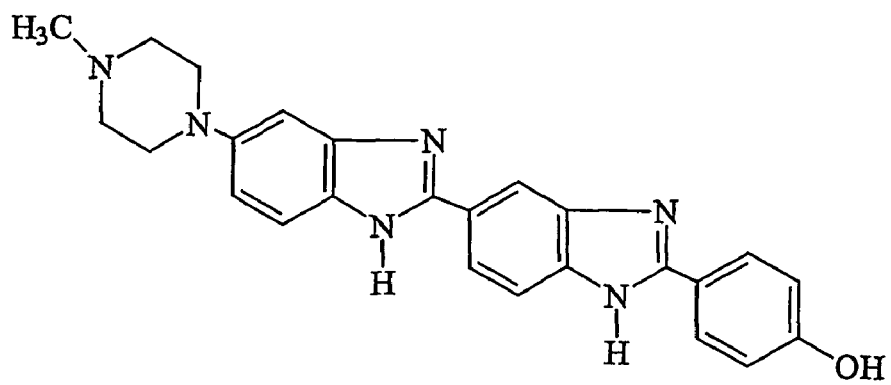

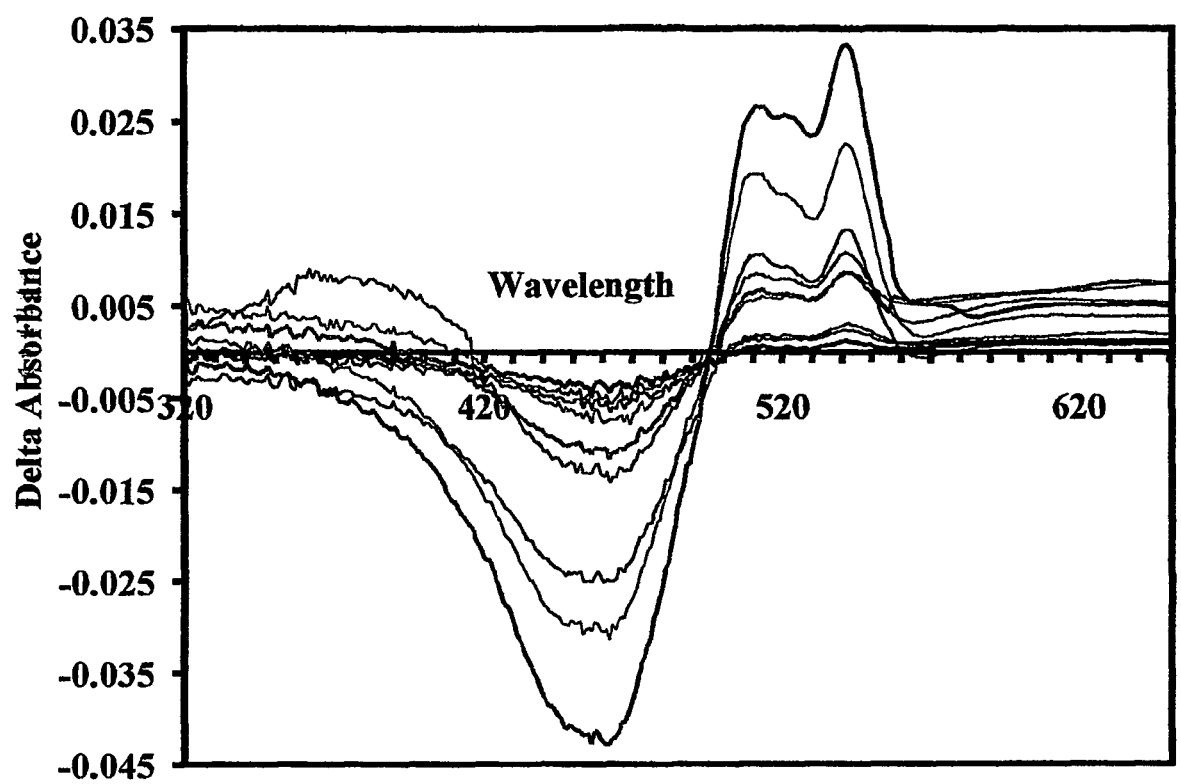
Fig. S-2

POLYNUCLEOTIDE INTERCALATOR INTERCEPTORS AND INHIBITORS

CROSS REFERENCE TO RELATED APPLICATIONS

This application claims the benefit of U.S. Provision Patent Application No. 60/251,906 filed Dec. 6, 2000, and entitled "Interaction of DNA with Xanthines, Acridine Orange, and Caffeine," which is expressly incorporated herein by reference in its entirety.

RIGHTS IN THE INVENTION

This invention was made in part with United States Government support under a grant number DE00152 awarded by the National Institute of Dental Research.

BACKGROUND OF THE INVENTION

This invention relates generally to the field of molecular biology and more specifically to the field of treatment and prevention of DNA binding agents.

Concern for the detrimental and carcinogenic interaction of drugs and chemicals with oral, respiratory tract, and other tissues continues to encourage the study of systems offering potential reduction of cancer risk. One such approach is the interaction of caffeine and other xanthine-like compounds with polynuclear aromatic hydrocarbons and related carcinogenic materials. This interaction likely occurs through a novel mechanism known as polarization bonding. Polarization bonding is the interaction of two planar molecules via a sandwich-like stacking to form a stable complex. This plane-to-plane packing of alternate polarizing and polarizable molecules results in a shortening of the van der Waals distances and thereby provides for the stability and the strength of the complexes formed. Polynuclear aromatic hydrocarbons (PAH), a class of carcinogens found in smokeless tobacco and tobacco smoke are proposed to be initiators of oral and respiratory tract cancer, respectively. FIG. 1-1 shows chemical structures of same PAHs. It should be noted that both xanthines and PAHs are planar molecules, and that planarity has been described as a requirement for carcinogenicity of PAH's as well as for complexation. The phenomenon of polarization bonding, specifically in the formation of xanthine-PAH complexes, has been observed, but has seldom been studied from a cancer prevention point of view. The complexation of PAH's to deoxyribonucleic acid may also be due to polarization bonding with the purine bases of DNA.

The effects of polarization bonding on carcinogenesis and mutagenesis has not specifically been reported in the literature based on Medline and Cancerlit computer searches, however the interaction of polynuclear aromatic hydrocarbons with caffeine and other xanthine-like compounds has been reported. For example, the measurement of the solubility and optical properties of PAHs in solutions of caffeine, TMU, or DNA indicate similar mechanisms in the formation of complexes. The complexation of PAH's to deoxyribonucleic acid may be due specifically to the purine bases comprising DNA. As noted the xanthines and PAHs are planar molecules, and planarity has been described as a requirement for carcinogenicity of PAH's (Pullman, 1955, 1964) as well as complexation (Jones and Neuworth, 1949; Leela and Mason, 1957; Pullman and Pullman, 1958; DeSantis et al., 1960, 1961; Liquori et al., 1962; Van Duuren and Bardi, 1963; Van Duuren, 1964).

Several laboratories have recently reported on the interaction of xanthines and xanthine analogs with carcinogenic polyaromatic DNA intercalators (Larsen et al., 1996; Traganos et al., 1991a, 1991b, 1993; MacLeod et al., 1991,1993; Kapuscinsid and Kimmel, 1993). FIG. 1-2 shows chemical structures of example xanthines. These same xanthines bind with DNA intercalators through an interaction referred to as polarization bonding (McKeown et al., 1951). Polarization bonding, is the $\pi$-$\pi$ interaction and stacking of two planar molecules, where one is polarizing (xanthine) and the other is polarizable (DNA intercalator). The binding of these carcinogens to certain xanthines has been shown to inhibit or reduce their binding to dsDNA (Booth and Boyland, 1953; Shoyab, 1979; Traganos et al., 1991a; MacLeod et al., 1991). Planarity has been described as a necessary requirement for polarization bonding complexation (McKeown et al., 1951; Harding and Wallwork, 1953, 1955; Wallwork, 1961; Liquori et al., 1962; Miller, 1970; Huberman et al., 1976) as well as for intercalation into dsDNA (Booth and Boyland, 1953; DeSantis et al., 1960, 1961; Van Duuren, 1964; Pullman, 1964). Polarization bonding has been proposed as the mechanism for the bonding of carcinogenic polyaromatic hydrocarbons, such as benzo[a]pyrene and dimethyl benzanthracene to the purine bases adenine and guanine within DNA as well as to other xanthine-like molecules (DeSantis et al, 1960, 1961). The specific mechanism by which xanthine-like molecules inhibit polyaromatic DNA intercalating agents (DNA-IAs) from intercalation into dsDNA has been suggested to be due to the formation of a polarization bonding complex between the xanthine and the DNA-IA (Traganos et al., 1991a, 1991b; Kapuscinski and Kimmel, 1993; Tachino et al., 1994; Larsen et al., 1996). The degree of reversibility of the intercalation of DNA-IAs into DNA, in vitro and in vivo, remains to be established.

SUMMARY OF THE INVENTION

According to one embodiment, the present invention is directed to a method of inhibiting complexation of intercalating molecules with polynucleotides. According to a preferred embodiment, the present invention is directed to a method comprising complexing a xanthine molecule to an intercalating molecule. According to one implementation, xanthine is contacted with the intercalating molecule, wherein the xanthine molecule may comprise at least one methyl group at the N1, N3, N7, and/or N9 positions.

According to another embodiment of the present invention, the xanthine molecule may also comprise at least one substitution of an oxygen group or a chlorine group at the C8 position. The present invention may be used on various intercalating molecules, including but not limited to the group consisting of acridine orange, doxorubicin, doxorubicin hydrochloride, novantrone, elipticine, ethidium bromide, Hoeschst 33258, aflatoxin and/or mixtures thereof.

The present inventive methods and/or compounds are also useful in the inhibition of intercalating molecules that are planar polyaromatic hydrocarbon molecules., e.g., benzo(a)pyrene and dimethyl benzanthracene.

According to another embodiment, porphyrins, instead of xanthines may be used to contact with the intercalating molecule.

According to still further embodiments, and depending upon the intercalator and/or intercalators, the number of methyl group substitutions on the xanthine molecule is increased. For example, the xanthine molecule of the present invention may be selected from the group consisting of 1-methyl xanthine, 1,3-dimethyl xanthine, 3,7-dimethyl xanthine, 1,7-dimethyl xanthine, 1,3,7-trimethyl xanthine, 1,3-dimethyl xanthine, 1,3-dimethyl-8-oxy xanthine, 1,3-dimethyl-8-chloro xanthine, 1,3,7,9-tetramethyl-8-oxy xanthine, and mixtures thereof.

According to a preferred embodiment of the present invention (and depending upon the intercalator or intercalators) the binding affinity between the intercalating molecule and the xanthine molecule is preferably at least 150 $MD^{-1}$. The present invention, according to one embodiment, is directed to methods that are useful wherein the polynucleotide is selected from a group consisting of DNA, RNA, and PNA, and the polynucleotide is single or double stranded.

According to another embodiment of the present inventive methods, intercalating molecules may be removed from polynucleotide molecules, by delivering a xanthine molecule and forming a xanthine-intercalating molecule complex and a polynucleotide molecule. The specific xanthine molecule and dosage used are dependent upon the circumstances and intercalating molecule or molecules present. Preferably the xanthine molecule comprises methyl groups at the N1, N3, N7, and/or N9 positions.

Depending on the circumstances and the intercalators present, the xanthine molecule may further comprise preferably oxygen or a halogen (Cl, Br, F, I) at the C8 position. The intercalating molecule is selected from the group consisting of acridine orange, doxorubicin, doxorubicin hydrochloride, novantrone, elipticine, ethidium bromide, Hoeschst 33258, and aflatoxin. The intercalating molecule may be a planar polyaromatic hydrocarbon molecule. The planar polyaromatic hydrocarbon molecule may be benzo(a)pyrene and dimethyl benzathracene.

Additionally, the number of methyl group substitutions on the xanthine molecule may be increased to five or less.

According to yet another embodiment of the present invention, the invention provides a composition for the efficient delivery of an anti-neoplastic agent to a patient. Preferably, the composition is manufactured from an antinoeoplastic agent and at least one carrier molecule. The carrier molecule may be selected from the group consisting of purines, pyrimidines, xanthines, and/or ursic acid. Preferably, the carrier molecule comprises DNA, RNA, or PNA. The carrier molecule of the present invention may be single stranded, double stranded, partially singled stranded and partially double stranded, multiple stranded, looped, and/or cross-linked, etc.

The composition of the present invention may, according to one embodiment, be manufactured from a carrier molecule that contains R-group substitutions around the purine, pyrimidine, xanthine, or uric acid. The composition may also contain R-group substitutions at the N1, N3, N7, or N9 positions. The composition may also contain other substitutions at the C2, C4, or C8 positions.

The present invention is useful for the treatment of mammals, humans, birds, fishs, amphibians, yeast, bacteria, nematodes, and insects. The present invention is also applicable to the treatment of plants, fungi, molds, algae, and/or other entities that contain nucleic acids and/or DNA Compositions of the present invention may be delivered by inhalation, oral administration, topical administration, transdermal administration, IV administration, IP administration, IM administration, by electroporation, or by liposomes.

In still another implementation of one embodiment of the present invention, a method of removing intercalating carcinogenic molecules from a substance that could be ingested by a mammal is provided. The method comprises delivering a xanthine molecule to a complex formed by an intercalating molecule and a substance capable of entering a body of a mammal and complexing with the intercalating molecule. The intercalating molecule may be an aflatoxin.

In still another implementation of the present invention, methods of removing anti-neoplastic intercalating compounds from cellular DNA of a mammal are provided. The methods comprise delivering a xanthine molecule or molecules to the complex formed by the interaction of an intercalating molecule and cellular DNA and forming a xanthine-intercalating molecular complex and cellular DNA. The intercalating molecule may be, e.g., doxorubicin.

Another implementation of the present invention comprises a method for reducing the intercellular concentration of an anti-neoplastic intercalating compounds. The method preferably comprises delivery of a xanthine molecule to an intercalating compound. The intercalating molecule is preferably doxorubicin.

In still another implementation of an embodiment of the present invention, a method of reducing the toxicity to mammals of polyaromatic hydrocarbons is provided. The method comprises delivering a xanthine molecule to the polyaromatic hydrocarbon. The polyaromatic hydrocarbon preferably is benzo(a)pyrene or dimethyl benzathracene.

Another implementation of the invention is to extact polyheterocyclic dyes and compounds from double stranded DNA. The method comprises contacting interceptor molecules with the aforementioned dyes and compounds. Formation of the complex between the polyheterocyclic dyes and interceptor molecules follows the removal of the dye from the double stranded DNA. The interceptor molecules are preferably purines, pyrimidines, xanthines, porphyrins, uric acid, polynucleotides, or polymers or mixtures thereof.

In another embodiment, the invention can be used to concentrate polyheterocyclic dyes. The method comprises contacting a polyheterocyclic dye molecule with an interceptor molecule. Interceptor molecules may comprise purines, pyrimidines, xanthines, uric acid, prophyrins, or polynucleotides. In a preferred embodiment, double stranded DNA is used as the interceptor molecule. Preferably, the concentration of double stranded DNA should be between 0.001% to 10% (wt/wt).

In still another embodiment of the invention, interceptor molecules are used to concentrate active agents in a medium. The method comprises contacting interceptor molecules with the agent to be removed. The choice of the interceptor molecule depends on the circumstances of the enviroment. Preferably the interceptor molecule may be a pyrimidine, purine, xanthine, uric acid, porphyrin, polynucleotides, or combinations or mixtures thereof. In another embodiment, the agent to be removed can exist in either a solid, liquid, or gas phase, and may simply be contacted to a support that is in a solid, liquid, or gas phase.

Other features and advantages will become apparent from the description and claims that follow.

BRIEF DESCRIPTION OF THE DRAWINGS

FIG. 1-2 illustrates chemical structures of selected xanthine compounds.

FIG. 1-3 is a model for a molecular stacking complex of the polyaromatic hydrocarbon pyrene and the xanthine 1,3,7,9-tetramethyl uric acid as proposed by DeSantis et al., 1960, 1961.

FIG. 2-1 illustrates tructural diagrams of the DNA intercalator acridine orange and selective xanthines found to form complexes with AO.

FIG. 2-2 is a spectral analysis and $K_{assoc}$ determination for the theophylline-AO complex.

FIG. 2-3 is an optical absorbance spectra taken from a series of titrations of chlorophyllin with acridine orange.

FIG. 2-4 shows potential energy curves arising from the resonance of the native-bond and no-bond electronic states in complexes of xanthines and acridine orange.

FIG. 3-1 is a plot of the optical absorbance spectra of acridine orange at various concentrations in the presence of and in the absence of 150 mM NaCl.

FIG. 3-2 is a plot of a spectrofluorometric analysis of acridine orange at concentrations ranging from 0.5 µM to 10.0 µM in the absence and presence of 150 mM NaCl.

FIG. 3-3 shows the optical absorbance spectra of acridine orange titrated with caffeine.

FIG. 3-4 is an absorbance binding spectra of 3 µM acridine orange titrated with caffeine.

FIG. 3-5 shows the effect of caffeine and NaCl on the fluorescence of acridine orange and the formation of the acridine orange-caffeine complex.

FIG. 3-6 is an optical absorbance spectra taken from a series of titrations of 3:M acridine orange with different concentrations of dsDNA.

FIG. 3-7 shows a delta absorbance plot of 3:M AO titrated with herring sperm dsDNA at DNA concentrations ranged from 30:M to 170:M.

FIG. 3-8 is a plot of a spectrofluorometric analysis of acridine orange [2 µM] with various concentrations of herring sperm dsDNA in the presence of and in the absence of NaCl [150 mM].

FIG. 3-9 is a plot of a spectrofluorometric analysis of 20 µM dsDNA in the presence of concentrations of acridine orange ranging from 0.5 µM to 10.0 µM, in the presence of and in the absence of 150 mM NaCl.

FIG. 3-10 is a schematic showing the relative population of acridine orange monomers and dimers at concentrations of 2 µM and 20 µM, and the binding of acridine orange monomers to individual molecules of caffeine.

FIG. 4-1 illustrates example chemical structures of the polyaromatic dsDNA binding agents.

FIG. 4-2 is a photomicrograph of chicken erythrocyte smear stained with 10 mM acridine orange at two exposure times to illustrate differential fluorescence color of nuclear chromatin.

FIG. 4-3 are photomicrographs illustrating the staining of the *Drosophila* salivary gland polytene chromosome with the DNA minor groove binder Hoechst 33258 and its subsequent removal by exposure to 100 mM caffeine for 15 minutes.

FIG. 4-4 shows a change in fluorescence intensity of acridine orange stained chicken erythrocytes rinsed with water, caffeine, and aminophylline over varying periods of time.

FIG. 5-1 is a schematic showing the orientation of caffeine and acridine orange within a polarization bonding complex (from Larsen al., 1996).

FIG. 5-2 plots the absorbance binding spectra of doxorubicin titrated with various concentration of caffeine.

FIG. 5-3 shows that optical absorbance spatra taken from a series of titrations doxorubicin with various concentrations of chlorophyllin.

DETAILED DESCRIPTION

The invention is directed, according to one embodiment, to the complexation of DNA intercalators with xanthine-based molecules According to one embodiment of the present invention, an excess of xanthine molecules-is provided such that the intercalator molecules are more likely to bind to the xanthine molecules instead of other molecules; e.g., DNA.

According to one embodiment, the DNA intercalator molecule may be treated with xanthine such that the DNA intercalator molecule will bind to the xanthine molecule. The amount of xanthine molecules present should preferably be greater than the amount of the intercalator molecules present, and the xanthine molecule preferably has a sufficient binding affinity for the DNA intercalator. When DNA is added to the xanthine, and the xanthine has a sufficient binding affinity for the DNA intercalator and an intercalator/xanthine complex is formed, the DNA intercalator will only bind to a minimal extent to the DNA.

Figure 1:
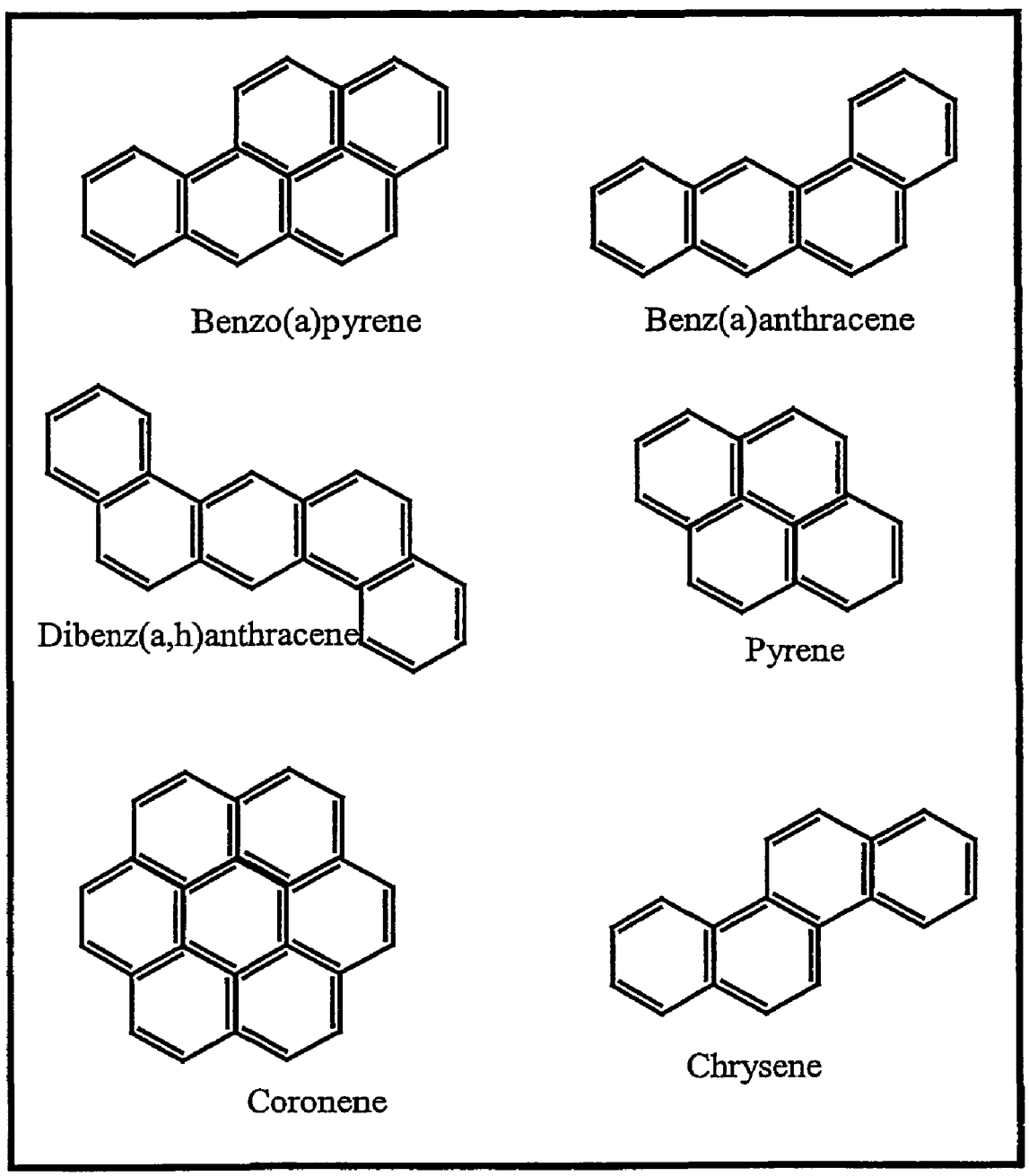
FIG. 1-1 shows chemical structures of example representative planar polynuclear aromatic hydrocarbons.
Figures 1, 2:
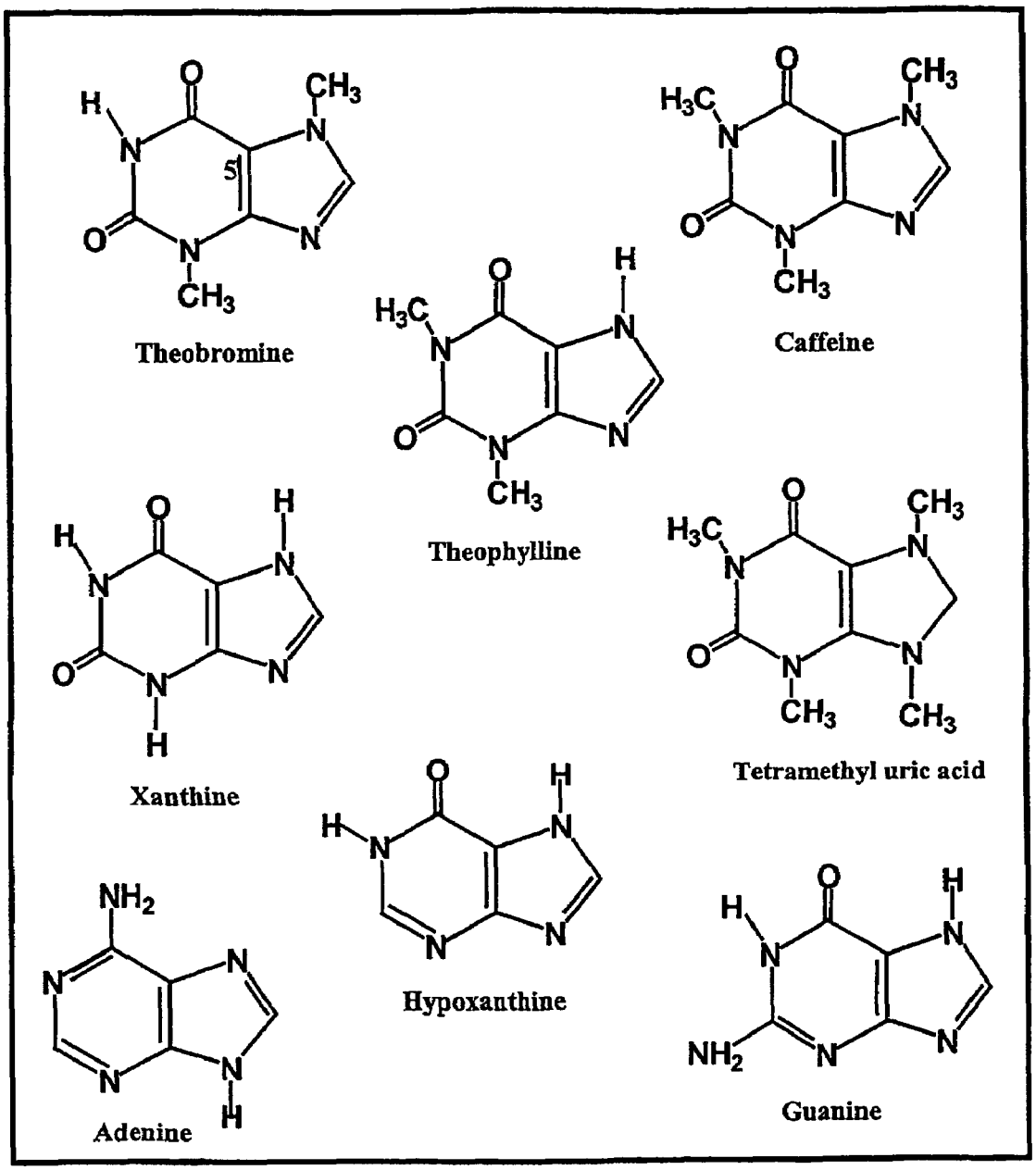

The xanthines and purines used in the following examples were obtained commercially at a purity of 98% or greater (Aldrich Chemical Company, Milwaukee, Wis.) and were used without further purification. Tetramethyl uric acid (1,3,7,9-tetramethyl-8-oxy xanthine) was obtained separately from ICN Biomedicals Inc., Aurora, Ohio. Acridine orange (3,6-bis[dimethylamino]acridine hydrochloride), >99% purity, (Aldrich Chemical Company, Milwaukee, Wis.) was prepared in a stock solution at a concentration of 50 mM in 5 mM HEPES buffer (1.0 M solution, Mediatech, Inc., Herndon, Va.). Acridine orange (AO) was chosen as a representative DNA intercalator because of its known spectral characteristics and its wide use as a fluorescence chromophore marker for both DNA and RNA (Robinson et al., 1973; Kapuscinski and Darzynkiewicz, 1987, 1990; von Tscharner and Schwarz, 1979). All stock solutions and subsequent dilutions were prepared by dissolving the appropriate weighed amount of compound in 5.0 mM HEPES adjusted to pH 7.0 with 0.1 M NaOH. Examples of the molecular structure of AO and some selected xanthines found to form complexes with AO are presented in FIG. 2-1. The following xanthines are shown in FIG. 2-1: (A) 1-methyl xanthine; (B) 1,3-dimethyl xanthine (theophylline); (C) 1,3,7-trimethyl xanthine (caffeine); (D) 1,3,7,9-tetramethyl-8-hydroxy xanthine (tetramethyl uric acid); and (E) 3,6-bis [dimethylamino] acridine (acridine orange).

EXAMPLE 1

Example 1 illustrates the complexation of xanthines with an intercalator molecule. The formation of a xanthine-intercalator complex can be demonstrated via a color shift using fluorscently labeled intercalator molecules. A red spectral shift in the optical adsorption maximum of AO upon the addition of a particular xanthine, indicates the possibility of a complex being formed between the two compounds. Spectral shifts can be measured by optical titrations.

Optical titrations (serial additions of various xanthines to a solution of AO) were performed on a Beckman DU-600 Scanning Spectrophotometer (Beckman Instrument Co., New York, N.Y.) using a 3 mL (1-cm light path) quartz cuvette containing 2.0 mL of a 10 µmol AO solution. The DU600 Spectrophotometer was blanked with 2 mL of a pH 7.0 buffered 5 mM HEPES solution over the full range of wavelengths to be scanned prior to sample analysis. This reduced the need to subtract the background absorbance from the HEPES buffer. Optical absorbance scans were performed over a wavelength range preferably from 400 nm to 550 nm. The absorbance spectra at wavelengths longer than 400 nm were minimal for the xanthines tested. The 10 µM AO solution was scanned before the start of each titration series to quantitatively monitor any changes in the absorbance spectrum. Optical absorbance experiments were performed using aliquots varying in volume from 1:L to 20:L taken from prepared xanthine stock solutions (5 mM to 50 mM) and titrated into the cuvette containing 2.0 mL of the 10 μM AO solution. The solution in the cuvette was then thoroughly mixed by 10 seconds of shaking before scanning. All titrations were performed at room temperature (25±1° C.). The absorbance spectra were measured in 1 nm intervals and stored in digital form. Digitized scan data was converted to a Lotus Spreadsheet file (*.wk1) using a conversion program supplied by the manufacturer (Beckman Instruments Inc.) then imported into a Microsoft Excel 97™ Workbook file (*.xls) and saved in this format for further analysis. Spectral data for each titration was combined and expressed in graphic form (Excel™) (X-axis=wavelength in nm; Y-axis=optical absorbance) for each xanthine titrated with AO. Initial absorbance data was corrected for the dilution due to the addition of the xanthine by multiplying the absorption value by an adjustment factor determined by the volume of aliquot added (Larsen et. al., 1996). This manipulation slightly increased the absorption value to offset the effects of dilution. Adjusted absorption values were plotted and compared to spectra from non-complexed AO. This allowed for the visualization of an expected spectral shift that occurs when AO forms a complex with a xanthine.

FIG. 2.2A shows the optical absorbance spectra of the theophylline-AO complex in the absence (I) and presence (II) of theophylline. The spectrum of the theophylline-AO complex is the result of 5 mM of theophylline and 10 μM of AO in solution and has been adjusted for dilution. The spectral shift (red), shown in FIG. 2-2A, in the optical adsorption maximum of AO upon the addition of a particular xanthine, indicates the possibility of a complex being formed between the two compounds. The optical spectrum of AO at 10 μM is displayed in FIG. 2-2A and exhibits an absorption band in the visible region with a maximum at about 495 nm. Upon the addition of 1,3-dimethyl xanthine (theophylline) for example, this maximum shifts to about 507 nm. This red shift in the absorption maximum of AO in the presence of theophylline provides a convenient method, by using a delta curve (FIG. 2-2B), for determining the association constant for the complex formed between AO and theophylline.

EXAMPLE 2

The kinetics of the system as encompassed in the binding affinity are explored in Example 2. The association constant, $K_{assoc}$, may be used to analyze the binding ability of modified xanthines to DNA intercalators. The association constant may be calculated based upon a differential shift in the absorbance spectrum. When the presence of the xanthine caused a spectral shift, a difference absorbance plot or delta plot was obtained. Delta plots were constructed by subtracting the adjusted absorption spectrum of AO in the presence of the xanthine from the initial spectrum of AO alone at each wavelength and for each aliquot of the titration. This procedure allowed for the creation of difference absorption values or delta absorption values. Delta absorption values obtained in this manner (Y-axis=delta absorption) were plotted against wavelength in nm (X-axis). The appearance of a single isobestic point was indicative of only two species present in solution, AO, and an AO complex. Graphic representation allowed for the selection of a wavelength with the maximum sensitivity for determining the association constant. This wavelength was characterized by the greatest positive response in delta absorbance values observed upon addition of each aliquot of xanthine to the AO solution. The AO-xanthine association or binding constant was determined by the following equilibrium expression:

$$I + X = IX \qquad \text{EQUATION 1:}$$

Where I represents the intercalator (AO), X represents the interceptor molecule (xanthine), and IX represents the AO-xanthine complex, respectively. This leads to the following equation (see Connors, 1987) for the association constant $K_{assoc}$:

$$\Delta A = K D P_o [X]/(1+K[X]) \qquad \text{EQUATION 2:}$$

Where $\Delta A$ is the change in absorption after addition of a xanthine ($\Delta A \% [IX]$) and becomes the Y-axis of the delta plot; D is the delta extinction coefficient (obtained from a fitted curve, as explained below); [X] is the xanthine concentration (moles) in the cuvette following each aliquot addition; $P_o$ is the concentration of the intercalator (AO) in moles; and K is the association constant ($K_{assoc}$). To solve for K, Equation 2 thus becomes:

$$\Delta A = K(\Delta A_{max})[X]/(1+K[X]) \qquad \text{EQUATION 3:}$$

The resulting $\Delta A$ values (Y-axis=)A) were plotted against the final xanthine concentration (X-axis=[X]) at the $\delta_{max}$ that exhibited the greatest sensitivity for monitoring the formation of the AO-xanthine complex. The $\Delta A_{max}$ value is the maximum absorbance of the complex at saturation (maximum amount of complex that can be formed at equilibrium) and is equivalent to the delta extinction coefficient multiplied by the concentration of substrate (i.e. AO) and can be expressed as $D[P_o]$. The $\Delta A_{max}$ value used to calculate the binding association constant (Equation 3) was iterated from the initial AO spectrum by two approaches as described below.

Equation 3 ($\Delta A = K(\Delta A_{max})[X]/(1+K[X])$) is the binding isotherm for a 1:1 interaction as represented by the binding of AO with xanthines. The experimental data consists of $\Delta A$ values obtained as a function of ligand (i.e. xanthine) concentration [X]. The fixed wavelength is chosen to give the largest possible $\Delta A$ value. The $\Delta A_{max}$ value is the maximum absorbance that can occur when the substrate (AO) is saturated or completely bound to ligand (xanthine). The range of xanthine concentrations [X] analyzed is listed in Table 1 and should preferably cover at least 60% of the binding isotherm or as much as is permitted by the experimental situation (Connors, 1987). Percent saturation is determined using the formula $[K_{assoc}[X]/(1+K_{assoc}[X])]*100$. Due to solubility restrictions by many of the xanthines tested, only four compounds exceeded 60% saturation with two compounds at approximately 50% saturation. The $\Delta A_{max}$ value used to calculate the binding association constant (Equation 3) was iterated from the initial AO spectrum by two approaches.

The first approach to determine $K_{assoc}$ was to select a $\Delta A_{max}$ value estimated from the experimental data followed by experimental iteration of this value to maximize the correlation coefficient of the non-linear analysis ($R^2$) while not deviating significantly from the model. The second approach for the determination of the $K_{assoc}$ utilized a two parameter fit where both K and $\Delta A_{max}$ were allowed to float simultaneously. Results from this second approach yielded mean values with standard error ranges for both $K_{assoc}$ and $\Delta A_{max}$. Comparison of the results between the two approaches indicate that either may be used to determine $K_{assoc}$, and in all cases the values obtained for xanthines at approximately 50% saturation and above were not significantly different.

Fits to the association curve were determined and a graph created by nonlinear least square analysis with Prism™ software (San Diego, Calif.). The value of the association constant ($K_{assoc}$) with a standard error was determined from this plot for both approaches described above. Results from the two approaches were compared and the $K_{assoc}$ values having the highest $R^2$ values and minimum standard errors are reported in Table 2-1. In Table 2-1, the compounds are grouped, on the basis of, increasing numbers of carbonyl groups substituted around the purine core structure. The wavelength (λ) in nm of the maximum possible deviation on the delta curve, the square of the correlation coefficient ($R^2$) of best fit of delta absorbance data (see text for equation), and the concentration range over which the xanthine was analyzed are also shown. A $K_{assoc}$ ($M^{-1}$) value of zero indicates no measurable association was detected. The number of resonance states is listed under "R.S." with the number of methyl groups indicated in parenthesis at the far right of the table.

As shown in Table 2-1, a methyl substitution at the N1, N3, N7, or N9 position can increase the binding affinity for the modified xanthine to DNA. Additionally a halogen at the C8 position also may increase its binding affinity to DNA such that the intercalator molecule is less likely to bind to DNA. Table 2-1 illustrates that the xanthines should preferably be selected from a group consisting of—methyl xanthine, 1,3-dimethyl xanthine, 3,7-dimethyl xanthine, 1,7-dimethyl xanthine, 1,3,7-tri-methyl xanthine, 1,3-dimethyl xanthine, 1,3-dimethyl-8-oxy xanthine, 1,3-dimethyl-8-chloro xanthine, and 1,3,7,9-tetramethyl-8-oxy xanthine. In another implementation, the invention may be applied to xanthines with other multiple substitutions on the xanthine molecule

TABLE 2-1

Results of spectrophotometric analysis for the determination of binding affinities ($K_{assoc}$) between acridine orange and substituted xanthines (mean ± S.E.)

| Compounds | $\lambda_{max}$ (nm) | Concentration (μM) | % Sat.[a] | $K_{assoc}$ ± S.E. ($M^{-1}$) | $R^2$ | R.S. (# $CH_3$) |
|---|---|---|---|---|---|---|
| Purine | 509 | 25-2199 | *[b] | ~2 | .9914 | 2 (0) |
| 6-methyl purine | — | 25-805 | — | 0 | — | 2 (1) |
| 6-chloro purine | — | 10-383 | — | 0 | — | 2 (0) |
| 1-methyl-6-amino purine | 507 | 25-1247 | * | ~14 | — | 2 (1) |
| 3-methyl-6-amino purine | 507 | 25-1507 | ~7 | 44.5 ± 0.2 | .9996 | 2 (1) |
| O-methyl guanine (2-amino-6-methoxy purine) | 511 | 25-745 | * | ~2 | — | 4 (1) |
| guanine mono phosphate | — | 50-455 | — | 0 | — | 4 (0) |
| xanthine (2,6-dioxy purine) | — | 50-475 | — | 0 | — | 5 (0) |
| 1-methyl xanthine | 511 | 50-536 | * | 79.2 ± 2.0 | .9818 | 3 (1) |
| 3-methyl xanthine | 545 | 50-762 | * | ~10 | — | 4 (1) |
| 7-methyl xanthine | — | 25-708 | — | 0 | — | 4 (1) |
| 1,3-dimethyl xanthine (theophylline) | 508 | 248-10000 | 61.7 | 157.0 ± <0.1 | 1.000 | 2 (2) |
| 3,7-dimethyl xanthine (theobromine) | 503 | 20-412 | * | 94.5 ± 1.3 | .9951 | 3 (2) |
| 1,7-dimethyl xanthine | 506 | 171-10000 | 61.7 | 155.3 ± 3.1 | .9956 | 2 (2) |
| 1,3,7-trimethyl xanthine (caffeine) | 511 | 495-25000 | 86.5 | 255.7 ± 4.8[c] | .9987 | 1 (3) |
| 1,3-dimethyl xanthine ethylenediamine (aminophylline) | 510 | 25-1503 | 47.4 | 596.2 ± 6.5 | .9976 | 1 (4) |
| uric acid (8-oxy xanthine) | — | 10-338 | — | 0 | — | 7 (0) |
| 1-methyl-8-oxy xanthine | — | 50-1622 | — | 0 | — | 5 (1) |
| 7-methyl-8-oxy xanthine | — | 5-305 | — | 0 | — | 6 (1) |
| 1,3-dimethyl-8-oxy xanthine | 509 | 1000-5000 | 16.2 | 38.5 ± 2.2 | .9660 | 4 (2) |
| 1,3-dimethyl-8-chloro xanthine | 508 | 10-5000 | 67.4 | 412.5 ± 11.7 | .9970 | 2 (2) |
| 1,3,7,9-tetramethyl-8-oxy xanthine | 511 | 25-1644 | 47.6 | 551.5 ± 9.0 | .9945 | 1 (4) |

[a]The percent saturation of the binding curve as calculated by the formula: $K_{assoc}$ [X]/(1 + $K_{assoc}$ [X]) * 100.
[b]Percent saturation is less than 10%.
[c]As validation of our procedure, the $K_{assoc}$ value of CAF-AO complex was found to be 256 $M^{-1}$ that corresponds closely with the value reported by both Larsen et al. (1996) and Kapuscinski and Kimmel (1993) of 258 $M^{-1}$.

In each case where $K_{assoc}$ was determined at xanthine concentrations below approximately 50% saturation of the binding curve, there was evidence to indicate that if $R^2 > 0.99$ then the resulting $\Delta A_{max}$ value was a good prediction of the $\Delta A_{max}$ value obtained using data taken over a wider concentration range and at xanthine concentrations >50% saturation. The spectra gave evidence for complex formation between AO and a xanthine even when xanthine concentrations were limited by solubility and the saturation of the binding curve was substantially less than 50%. However, in these cases a binding constant could only be determined at a low level of confidence, therefore, such values are not given serious weight in the discussion of the results. In one implementation, the $K_{assoc}$ value of CAF-AO complex was found to be 256 $M^{-1}$.

FIG. 2-2B shows the absorbance difference spectra of AO titrated with theophylline. Spectral analysis was performed on a series of AO titrations with theophylline. Absorbance values were obtained and adjusted to take into account the effect of dilution. The initial intercalator (AO) concentration is preferably 10 μM in 5 mM HEPES buffer at pH 7.0. Theophylline was pipetted into the AO solution in 1 μl aliquots from a 50 mM stock solution. The resulting plot shows the presence of a single isobestic point, indicative of only two species in solution. The determination of the association constant, $K_{assoc}$, (the $K_{assoc}$ value between theophylline with AO) is determined from the curve in FIG. 2-2C. The optical difference spectrum of the AO-theophylline complex in solution displays a single isobestic point, characteristic of only two absorbing species in solution. Using the equation ΔA=K ($\Delta A_{max}$)[X]/(1+K[X]) (see Equation 3), the calculated $K_{assoc}$ value for the AO-theophylline complex is about 157.0±<0.1 $M^{-1}$. The other xanthines were similarly analyzed and their $K_{assoc}$ constants are reported in Table 2-1.

Of the twenty-two different xanthines tested, six were determined to have substantial (∃150 $M^{-1}$) association constants. An additional eight compounds showed some evidence of complex formation with AO. These 14 compounds are listed in Table 2-1 along with the wavelength (nm) at which the binding constant was derived, the concentration range of the xanthine tested (μM), the percent saturation of the binding curve, the $K_{assoc}$ ($M^{-1}$) value, the regression analysis $R^2$ value, the number of resonance states "R.S." (discussed later), and the number of substituted methyl groups (# $CH_3$). None of the seven purines tested revealed any substantial binding affinity with AO.

In another implementation, compounds that were found to have substantial binding with AO had three common structural similarities: (1) the $N_1$ or $N_3$ on the xanthine core structure must be substituted with a methyl group, (2) oxygen or chlorine substitution at $C_8$ increased $K_{assoc}$ when the number of resonance states remained unchanged, and (3) $K_{assoc}$ increased with increase in number of methyl group substitutions, generally with an empirical fit ($R^2$=0.99) to a second order polynomial equation.

Compounds without a methyl group substitution such as xanthine and 8-hydroxy xanthine (uric acid) did not complex with AO, as determined by optical titration. Of the six compounds that exhibited significant $K_{assoc}$ values, all had a methyl group substituted at $N_1$ and carbonyl groups at $C_2$ and $C_6$. Alternatively, compounds without a methyl group at $N_1$ of the xanthine base structure, but having substituted methyl groups in other positions (3-methyl xanthine, 7-methyl xanthine, 3,7-dimethyl xanthine, and 7-methyl-8-oxy xanthine) showed little or no affinity to complex with AO except for 3,7-dimethyl xanthine (theobromine). The compounds 1-methyl xanthine, 1-methyl-8-oxy xanthine, 1,3-dimethyl-8-oxy xanthine, and 1,3-dimethyl-8-chloro xanthine have carbonyl groups at $C_2$ and $C_6$ and a methyl group substituted at $N_1$, yet failed to exhibit any significant binding affinity for AO. One difference between 1-methyl xanthine, which has a binding affinity for AO of 79.2±2.0 $M^{-1}$, and 1-methyl-8-oxy xanthine, is a carbonyl group at $C_8$. Likewise, one difference between 1,3-dimethyl xanthine (theophylline) with a binding constant of 157.0±<0.1 $M^{-1}$ and 1,3-dimethyl-8-chloro xanthine or 1,3-dimethyl-8-oxy xanthine is the presence of an atom with high electron affinity (oxygen or chlorine, respectively) substituted at $C_8$. The presence of a carbonyl group at $C_8$ significantly reduces the binding ability of mono- and di-methyl substituted xanthines except for the tetramethyl substituted TMU, which exhibits a lower binding affinity than aminophylline; and also contains a total of four methyl groups.

It is possible that the binding of AO to substituted xanthines can be modified by specific substitutions in systematic ways as discussed below. Additionally, the formation of a complex between AO and xanthine derivatives may be predicted based on the theoretical energy state of that particular xanthine. Finally, it is likely that a correlation between $K_{assoc}$ and the ability of some xanthines to increase solubility of another PAH, benzo(a)pyrene, and other potential applications. It is noted that the invention is not limited in any way by the proposed mechanisms.

The formation of a complex between any two molecules occurs preferably when it is thermodynamically advantageous for the complex to exist (Wallwork, 1961). Since the formation of a complex allows for a reduction in the overall energy state of a molecule, it would be less thermodynamically advantageous for a lower energy molecule to form a complex than for a higher energy molecule. Thus, as the energy of a molecule decreases, the probability of that molecule forming a complex also decreases. The overall energy state of the xanthine molecule, and, therefore, its potential to form a complex with AO, probably is due to three important factors: (1) the number of potential resonance states, (2) the amount and position of N-methylation, and (3) the chemical characteristics of the R-group substituted at the $C_8$ position of the xanthine ring. All of these factors can influence π-orbital charge distribution, the hydrophobicity of the molecule, the electronic energy state, and, therefore, the thermodynamic potential for the formation of a complex.

Resonance states occur within molecules when, quantum-mechanically, they are able to exist simultaneously in different structural forms that de-localize the electronic density. This can occur with a "floating" double bond as seen in the five membered ring in xanthine, or with a double bond that is in equilibrium with a single bond as in tautomeric compounds such as those formed by uric acid. When the resonance states for the molecules tested were counted, those with only one resonance state were found to have the higher $K_{assoc}$ values (see Table 2-1). Conversely, those molecules with four or more resonance states exhibited little or no complex formation. Examination of the $K_{assoc}$ values for both substituted xanthines and uric acids versus the number of resonance states (Table 2-1) shows that as the number of resonance states increases, $K_{assoc}$ values decrease. Among the di-methyl substituted xanthines, 3,7-dimethyl xanthine with three potential resonance states has a 41% lower $K_{assoc}$ value than 1,7- or 1,3-dimethyl xanthine, both of which have only two potential resonance states. The lower $K_{assoc}$ value for 3,7-dimethyl xanthine suggests that there is a lower energy state associated with the higher number of potential resonance states. Both 1,3-dimethyl xanthine and 1,7-dimethyl xanthine have two potential resonance states and have a similar $K_{assoc}$ value. Structurally both molecules differ only by the position of the second substituted methyl group on the xanthine core, either at the $N_3$ or $N_7$ position, suggesting that the position of the second methyl substitution contributes little if any to the stability of the complex. Additionally, the difference in $K_{assoc}$ between 1,3-dimethyl xanthine and 1,3-dimethyl-8-chloro xanthine, both with only two potential resonance states, must be due to the difference in the chemical characteristics between hydrogen and chlorine. The number of potential resonance states in which a molecule can exist in addition to the chemical characteristics of the R-group substituents, probably exert a substantial influence on the energy state of the xanthine molecule. Consequently, the position of the substitution on the ring structure should have only a minor contribution if the number of resonance states is not changed by a shift in the position of the R-group.

One way to increase the electron-donor properties of purines or xanthines is N-methylation. The degree to which such methylation increases these properties depends in part on the chemical structure and, for a given compound, on the position of the alkyl group. Based on molecular orbital theory, the position of N-methylation of the xanthine core structure should increase the electron-donor properties with $N_3 > N_7 \cong N_9 > N_1$ In uric acid however, the activation of its electron-donor properties should occur for N-methylation at $N_7 > N_3 > N_9 >> N_1$. As seen in Tables 2-1 and 2-2, a pattern of increasing $K_{assoc}$ values between substituted xanthines and AO occurred with increasing N-methylation. With each addition of a methyl group to the xanthine core structure, $K_{assoc}$ approximately doubles. Binding affinity ($K_{assoc}$) versus methyl group substitution was plotted using the exponential formula Y =Start*exp(K*X) where the plot begins at Y=Start and increases exponentially with rate constant K with a doubling equal to 0.69/K. Regression analysis resulted in no significant deviation from the exponential equation (P=0.429) with an $R^2$ value of 0.99. Thus, a high correlation exists between the number of methyl substitutions on the xanthine ring and the resulting $K_{assoc}$ value.

The results illustrated in Table 2-1 indicate that binding affinity ($K_{assoc}$) is also affected by the position of the methylated nitrogens around the xanthine core. Among the monomethylated xanthines, both 1-methyl xanthine and 3-methyl xanthine were found to exhibit some evidence of weak binding affinity to AO as determined by spectrophotometric analysis, but the binding was not definitive (i.e., $K_{assoc}$ <150 $M^{-1}$ and limited concentration range i.e., saturation <10%). However, a single methyl substitution at $N_7$ resulted in no detectable evidence for AO complexation (saturation <10%). Examination of the xanthine core structure shows that the $N_1$ position on the ring is situated between two double bonded oxygen groups, whereas $N_3$ is near only one double bonded oxygen at $C_2$, while $N_7$ has no double bonded oxygen nearby. The electron directing effect of a methyl group may likely enhance the resonance between the lone-pair $N_7$ p-orbital electrons and the neighboring oxygen groups. This in turn could contribute to the electron density of the π-electron cloud in the vicinity of the ring structure. Thus, the contribution to the formation of π-π bonds between AO and the monomethyl-substituted xanthines may be enhanced by this nearest neighbor effect, with methyl substitution having the greater effect at $N_1$>$N_3$>$N_7$≅$N_9$. There is probably some contribution to the stability of the complex due to the elevated energy state of the core molecule through the loss of two resonance states, in addition to the electron donor contribution from the methyl group.

In the case of 1,3-dimethyl xanthine ethylenediamine (aminophylline), there are two theophylline groups linked by ethylenediamine. Aminophylline exists in solution as two molecules of 1,3-dimethyl xanthine (theophylline), each molecule bonded ionically at the $N_7$ position of the xanthine core to the nitrogen at each end of the ethylenediamine linker molecule. The chemical structure of aminophylline in solution can thus best be described as 1,3-dimethyl xanthine with an ethylenediamine theophylline R-group ionically bonded at the $N_7$ position. The resulting $K_{assoc}$ value suggests that the loss of a resonance state, together with the increased electron-donor capacity of the R-group at $N_7$, significantly enhances the ability of theophylline to complex AO by 280% as compared to 63% enhancement with the substitution of a methyl group at $N_7$ in the case of caffeine (1,3,7-trimethyl xanthine).

The influence of the number of methyl groups on $K_{assoc}$ is less obvious when there is a simultaneous substitution of either oxygen or chlorine at the $C_8$ carbon. As can be seen in Table 2-1, the substitution of a carbonyl group at $C_8$ significantly decreases the ability of AO to bind with methyl-substituted xanthines (e.g., $K_{assoc}$ for 1,3-dimethyl-8-oxy xanthine is 38.5 $M^{-1}$). By examination of FIG. 2-1, it can be seen that in the xanthine core structure, the double bond at $C_8$ can resonate between $N_7$ and $N_9$ and the hydrogen substituted carbon at $C_8$. With a carbonyl substitution at $C_8$, resonance of the double bond between $C_8$ and $N_7$ or $N_9$ is enhanced and allows for an additional resonate state to exist when the oxygen at $C_8$ tautomerizes between the carbonyl and the hydroxyl form. Simultaneously, the dipole moment of the molecule has significantly decreased and shifted away from the six-membered ring toward the oxygen at $C_8$, becoming more centralized over the core structure. With the substitution of chlorine at $C_8$, the double bond can still resonate between $N_7$ and $N_9$, but the π-electron cloud will be less centered above and below the planar rings of the xanthine and, therefore, will be displaced toward the chlorine atom with its higher electron affinity. These features appear to enhance $K_{assoc}$ about 10-fold. It should be noted that the addition of methyl group substitution at $N_7$ and $N_9$ tends to offset the electron affinity effects of the carbonyl at $C_8$, and the resulting change in the dipole moment. Therefore, the substitution of a carbonyl group in the $C_8$ position creates a mobile or resonate hydrogen (between $N_7$ and $N_9$) that is probably not present in the tri-methyl xanthine or the tetramethyl uric acid molecules.

In the case of the AO-caffeine system, the spectral change is quite similar to that observed for the AO-DNA intercalation complex, suggesting the occurrence of comparable interaction between the chromophore and the hydrophobic surface of the aromatic compounds such as caffeine or DNA base pairs. The monomerizing (disaggregating) capacity of weakly polar solvents, α-cyclodextrin, and detergents originates from the reduction of the degree of dye solvation. Under these conditions, hydrophobic interactions between stacked dye chomophores (dimers) can generally disappear and absorption spectra characteristic of the dye monomers are obtained.

Organic solvents, as well as the internal space of α-cyclodextrin and detergent micelles, provide the same hydrophobic weakly polar environment that occurs in the intercalative cavity of nucleic acids. The simplest formulation, hydrophobic interactions between DNA, AO, and planar xanthines can be represented as stacked complexes.

Table 2-2 compares the $K_{assoc}$ values found in Table 2-1 with the solubility values reported by Weil-Malherbe (Weil-Malherbe, 1946a, 1946b).

TABLE 2-2

Relationship between: number of methylations on the xanthine ring, the $K_{assoc}$ value with acridine orange (this report) and the ability of the xanthine compound to solubilize benzo(a)pyrene in water as reported by Weil-Malherbe (1946a, 1946b).

| Compounds | $CH_3$ | $K_{assoc}$($M^{-1}$) | Solubility |
|---|---|---|---|
| 1-methyl xanthine | 1 | 79[a] | 17[b] |
| 1,7-dimethyl xanthine | 2 | 155 | 27 |
| 1,3-dimethyl xanthine | 2 | 157 | 28 |
| 1,3,7-trimethyl xanthine | 3 | 256 | 100 |
| 1,3,7,9-tetramethyl-8-oxy xanthine | 4 | 552 | 524 |

[a]Percent saturation of the binding curve was less than 10 percent.
[b]Due to lack of a specific solubility value for 1-methyl xanthine, the average of the solubility values reported for 3-, 7-, and 9-methyl xanthine was used.

In Table 2-2, solubility units are based on a comparison to caffeine, which was given a value of 100. A non-linear regression analysis reveals a good fit to the exponential equation Y=Start*exp(K*A) between the number of methyl groups substituted on the xanthine ring and the solubility values reported by Weil-Malherbe (1946a, 1946b) for xanthines with benzo(a)pyrene ($R^2$=0.98). A comparison of the results from both the $K_{assoc}$ values and the solubility values from Weil-Malherbe shows a significant linear correlation (P=0.002, $R^2$=0.90).

The effect of structural changes on the interaction of xanthines with AO follow closely those described by Weil-Malherbe in his studies of the solubilization of polyaromatic hydrocarbons with purine bases. One of the structural differences among a purine, hypoxanthine, xanthine, and uric acid core molecule is the number and presence of oxygen groups bonded to a carbon atom at $C_2$, $C_6$, or $C_8$ of the purine base structure. Purine has no substituted oxygen groups whereas hypoxanthine has an oxygen group substituted at $C_6$, xanthine has an oxygen at $C_2$, and $C_6$, and uric acid has an oxygen at $C_2$, $C_6$, and $C_8$. Weil-Malherbe observed that the solubilization of the PAH benzo(a)pyrene increased with increasing N-methylation and, up to a point, with increasing substitutions and increasing electron affinity of the R-groups at $C_2$, $C_6$, or $C_8$ around the purine ring. He found that increasing the number of carbonyl groups around the purine ring increased the solubility of benzo(a)pyrene in all cases. However, the substitution of a chloro-, thio-, or amino-group might either increase or decrease solubility. The relationship between N-methylation (X-axis) and solubilization (Y-axis) can be fitted, empirically, with the exponential equation $$Y=Start*exp(K*X) (R^2=0.98).$$

This relationship suggests that the solubilization of PAHs such as benzo(a)pyrene, may be due to complex formation between the PAH and the xanthine, and, therefore, directly related to $K_{assoc}$. Table 2-2 compares the $K_{assoc}$ values and the solubility values from Weil-Malherbe (1946a and 1946b) and reveals the existence of a significant linear correlation (P=0.002, $R^2$=0.90) between the two sets of data values. Based on these results, solubilization can be used to screen potential interceptor molecules for their ability to form $\pi$-$\pi$ stacking complexes with DNA Rapid screening of potential interceptor molecules for their ability to form $\pi$-$\pi$ bonding complexes with DNA intercalators, could be achieved using Bowman and Beroza (1965a, 1965b, 1965c, 1966a, 1966b) partitioning values (P-values) utilizing the method described by Robbins (1979).

Knowledge of the interaction of selected xanthines with PAHs has practical applications. The interaction of xanthines such as caffeine with the anti-neoplastic drug doxorubicin (DOX) causes the reduction of blood plasma levels of DOX and a simultaneous increase at the intracellular level. The ability to optimize the binding affinity or $K_{assoc}$ value between two interacting classes of compounds would create novel approaches relevant to drug therapy and delivery. For example, enhancing target site concentration of an anti-neoplastic drug such as doxorubicin could simultaneously increase cellular toxicity within the tumor while decreasing the overall systemic toxicity by a reduction in blood plasma levels. Additionally, interceptor molecules could potentially be designed to bind with specific carcinogens with a very high affinity and therefore, significantly reduce their biological effects. Finally, by using the laws of mass action, on which polarization bonding depends, the possibility exists for the creation of compounds for the selective prevention and/or reversal of DNA intercalation by PAHs.

Results from spectral analyses of various xanthines with the DNA-intercalator AO, demonstrate that specific xanthines can complex with AO. This interaction is attributed to a type of B-B electron orbital interaction known as polarization bonding. Xanthines with specific R-group substitutions modify binding affinity to AO in at least three systematic ways: (1) increased with an increase in N-methylation around the xanthine core, (2) increased by an increase in the potential energy of the xanthine molecule, as evidence by a decrease in the number of resonance states, and (3) the electron affinity and other chemical characteristics of substituents appears to affect $K_{assoc}$. The dominant influence in the formation of such complexes appears to be van der Waals interactions resulting in maximal B-orbital overlap between the two molecules of the complex, and the hydrophobic effects of the methyl group substitutions. Additionally resonance with a donor-acceptor charge transfer state may also contribute to the stabilization of the complex. The hydrophobic effect is an entropic rather than an enthalpic phenomena based on the exclusion of water molecules. These results suggest a possible role for CAF and other xanthines as interceptor molecules in cancer therapy.

These application of this invention is not limited to the DNA intercalator acridine orange. The invention may be applied to other heterocylic compounds such as doxorubicin and its associated salts, novatrone, elipticine, ethidium bromide, Hoeschst 33258, aflatoxin, or other similar molecules. In other implementation, polanar polyaromatic compounds such as benzo(a)pyrene and dimethly benzathracene may be used. Moreover, the invention is not limited to double stranded DNA. Other compounds such as RNA, PNA, and single and double stranded versions thereof, may be used.

Figures 1, 2, 3:
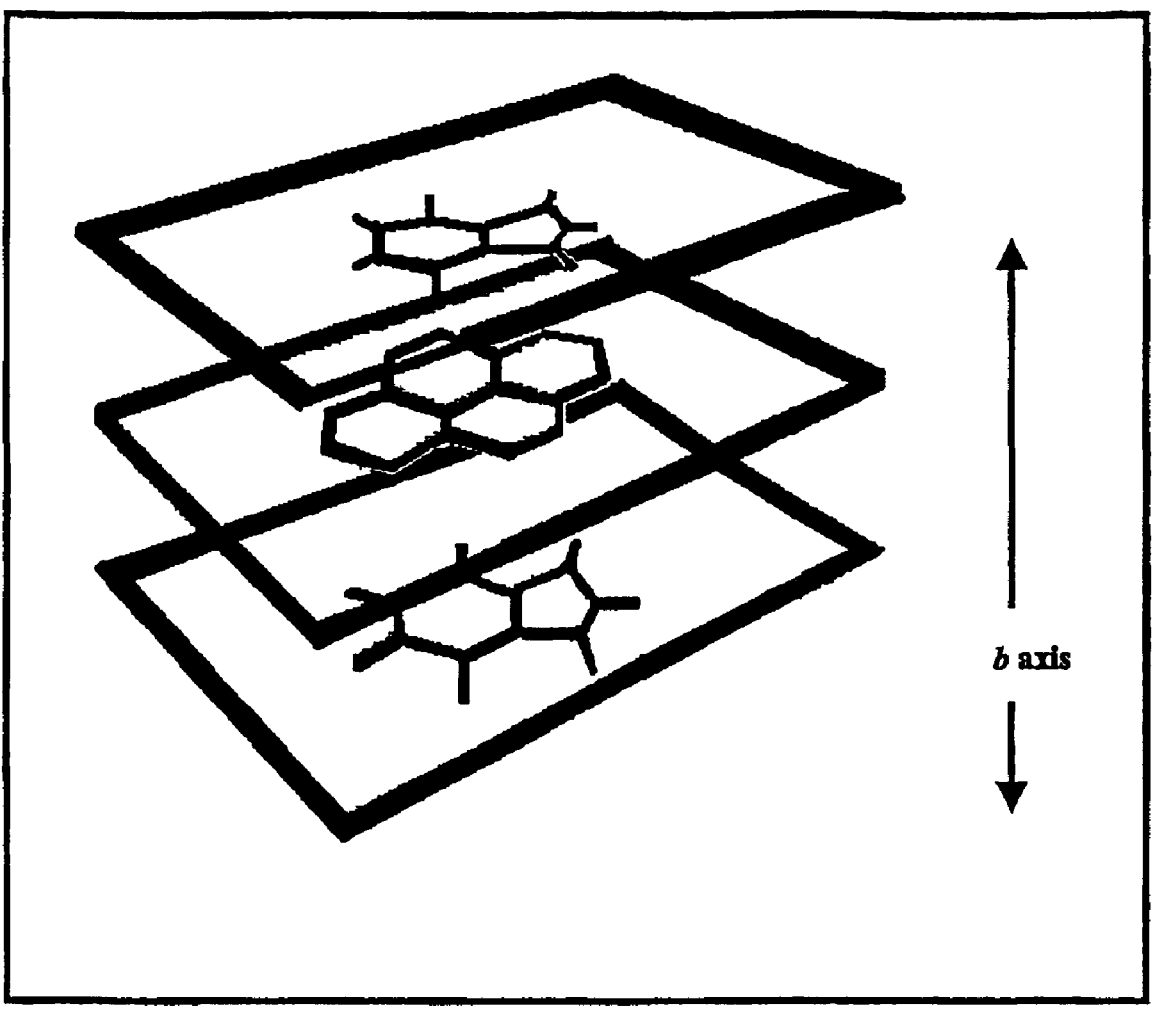
Figure 2:
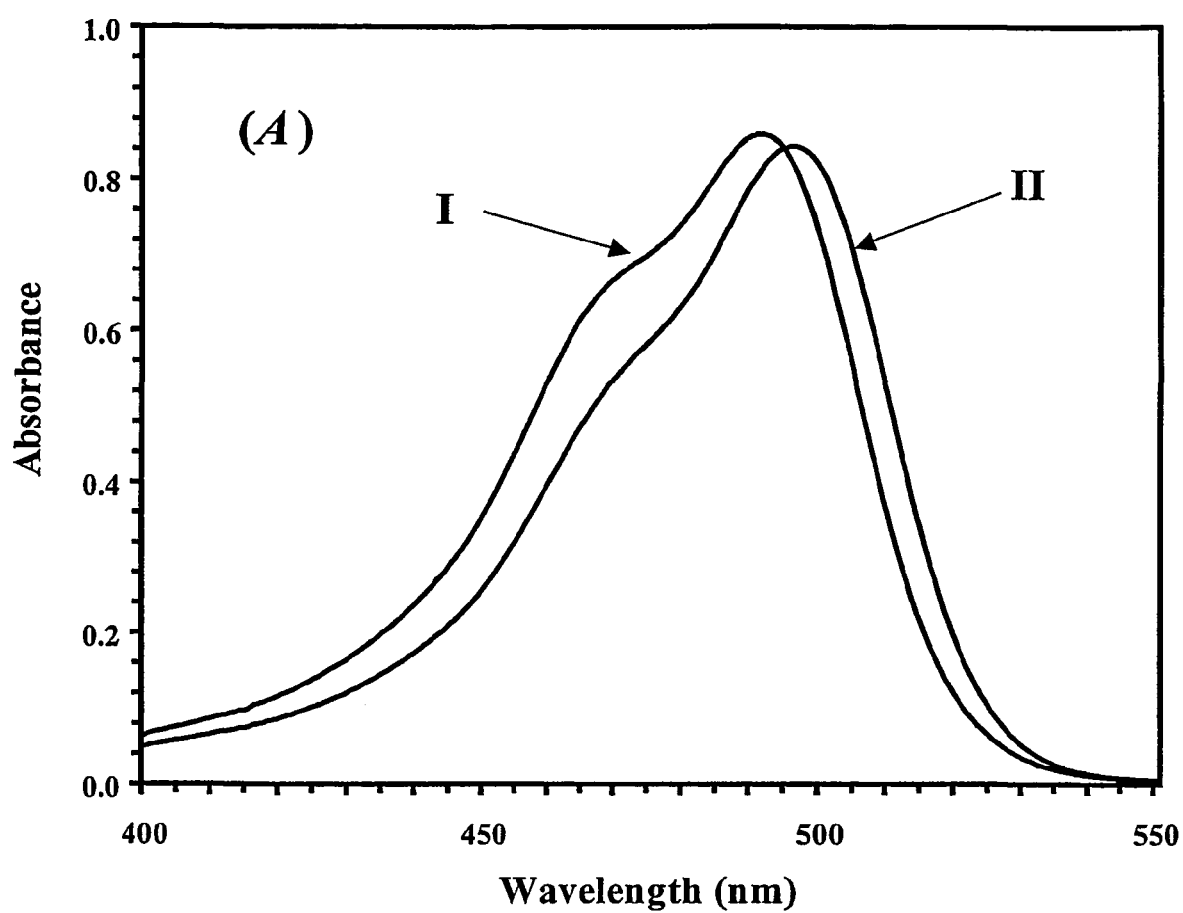
Figure 2:
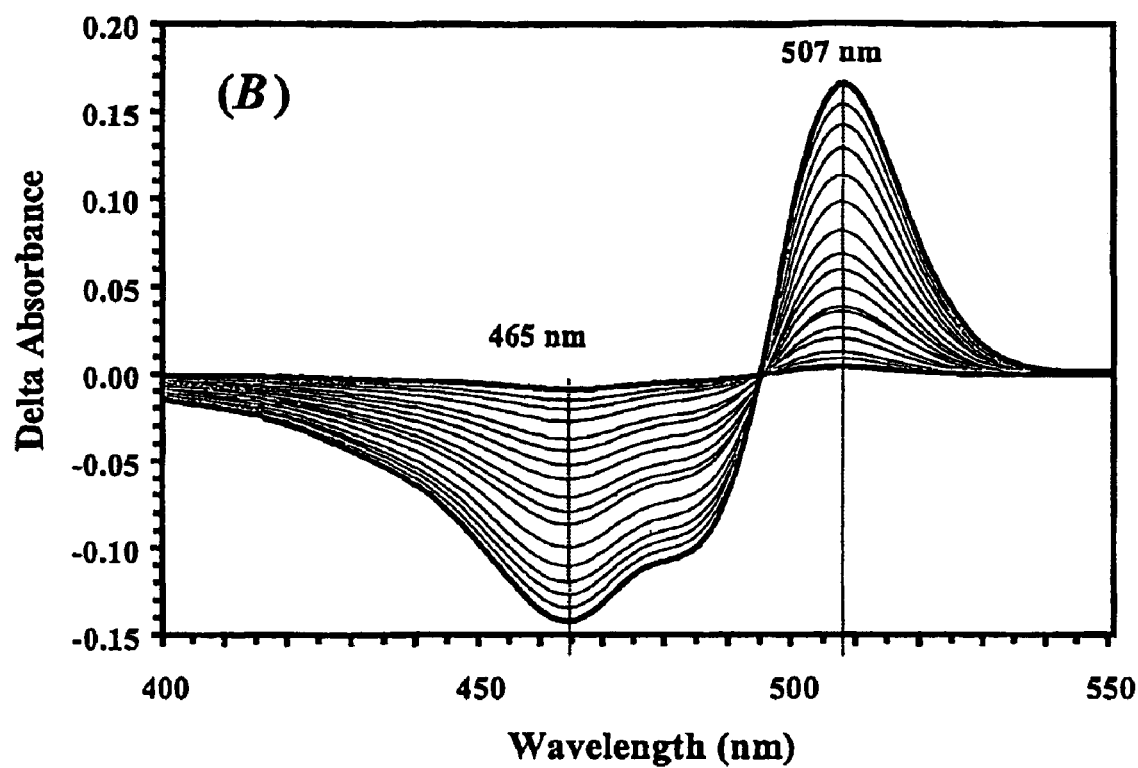
Figure 2:
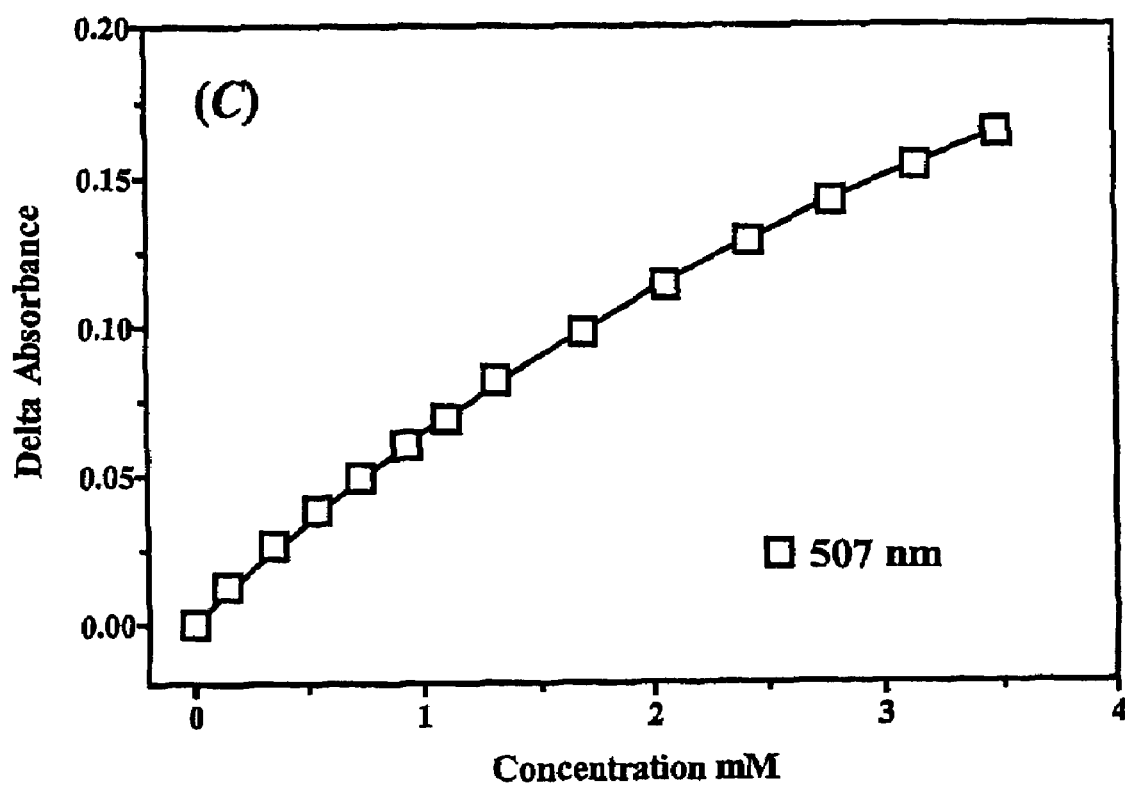
Figures 2, 3:
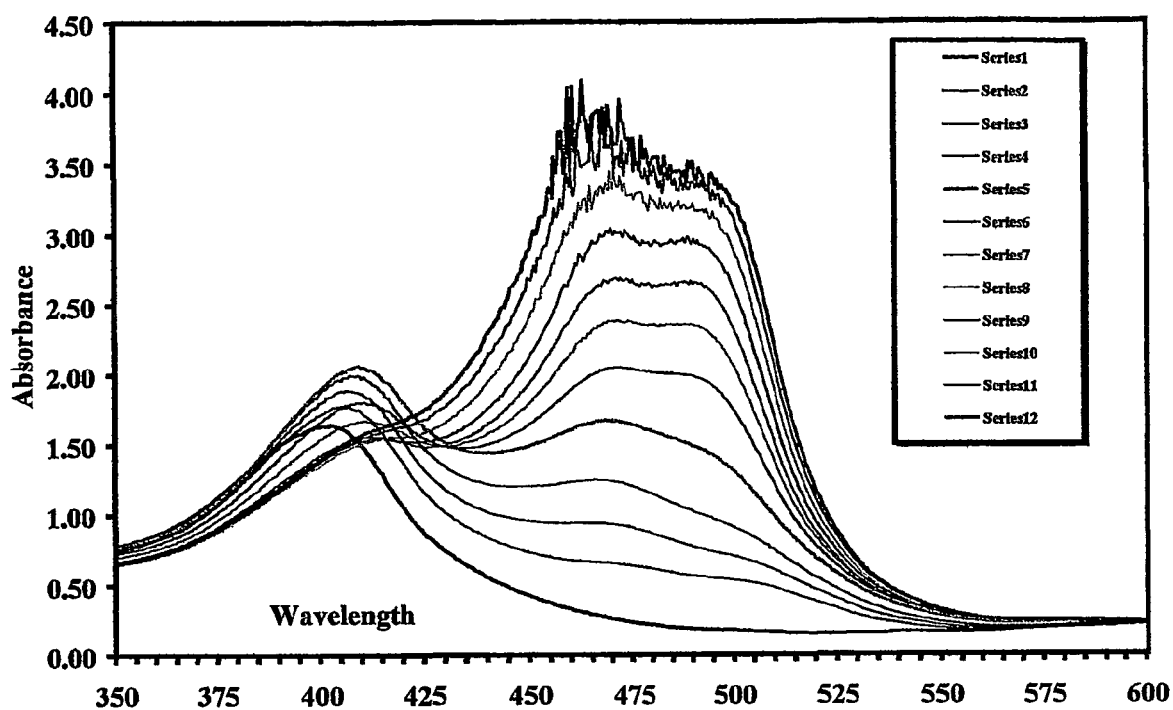
Figure 1:
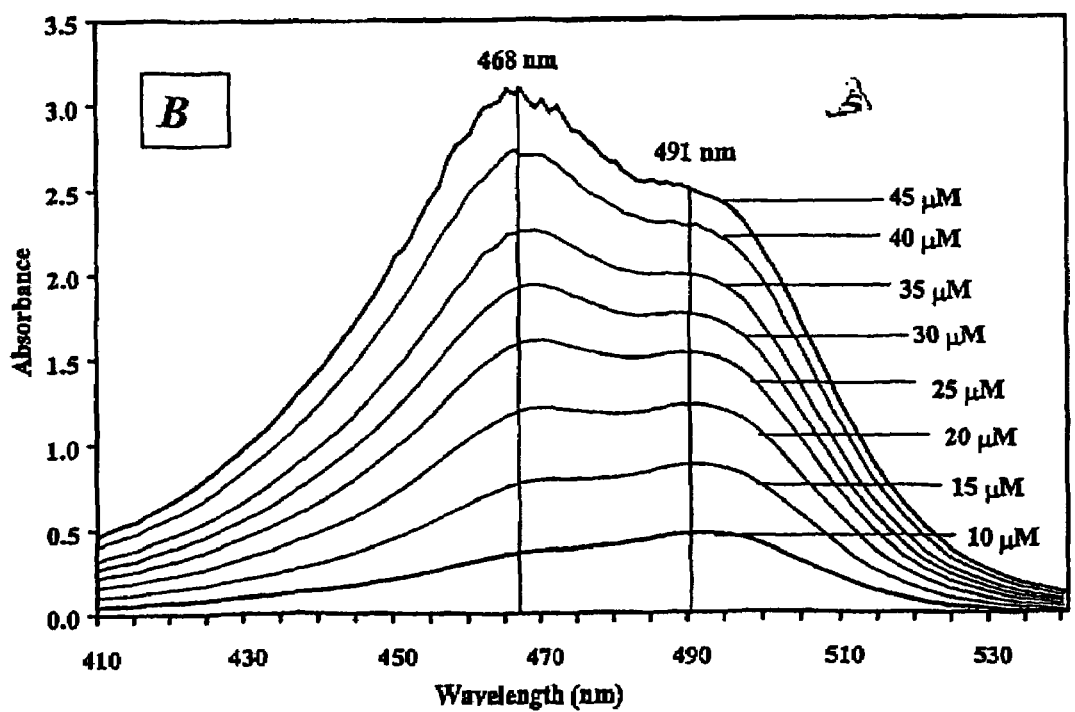
Figure 2:
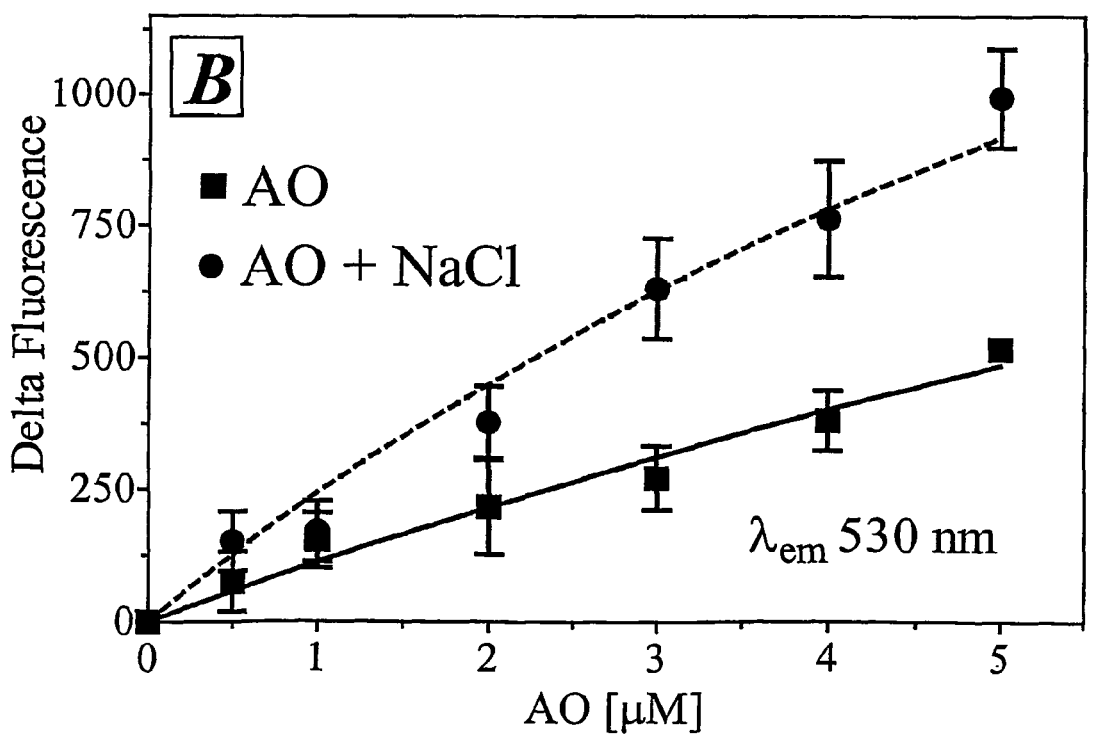

The invention is not limited to the use of xanthines as interceptor molecules. For example, chlorophyllin and porphyrins may be used as a binding agent to intercalator molecules. FIG. 2-3 shoes the optical absorbance spectra titrating cholrphyllin with increasing concentraitons of acridine orange. The selected spectra denoting important transitions within the titration series are denoted by the bold lines. At AO:chlorophyllin ratio between 0.1 and 30, prevalent peaks occur at $\lambda_{abs}$ of 415 nm for chlorophyllin, 475 nm, and 492 nm. These later peaks correspond to the prevalent absorbance peaks found at concentrations of AO at 10 μM and higher concentrations. This figure illustrates that chlorophyllin complexes with acridine orange. Thus, other compounds may be used as interceptors such as, but not limited to porphyrins, purines, pyrimidines, polynucleotides and uric acid.

EXAMPLE 3

The addition of salt affects the conformation of both the polynucleotide and the intercalator molecule. Thus, the use of modified xanthines may be tailored through the control of the ionic environment. As in the previous examples, the ability of the modified xanthines to bind with an intercalating molecule is described via binding affinities.

Association constants were calculated using a modification of an equation described by Zaini et al. (1999) to determine equilibrium constants for weakly bound complexes by absorbance spectrophotometry. By definition $K=X_d/(X_{m^*\ Xm})$, where K is the binding constant $K_{assoc}$, $X_d$ is the concentration of the AO dimer and $X_m$ is the concentration of the AO monomer. Conservation of mass gives $X_t=X_m+2*X_d$, where $X_t$ is the total concentration of AO in solution. Rearranging the conservation of mass equation gives $X_m=X_t-2*X_d$, and substituting into the equation for $K_{assoc}$ and rearranging gives Equation 4:

$$K_{assoc}(X_t*X_t-4*X_t*X_d+4*X_d*X_d)-X_d=0 \quad \text{EQUATION 4:}$$

Rearranging gives:

$$X_d*X_d-(X_t+1/(4*K_{assoc}))*X_d+X_t*X_t/4=0 \quad \text{EQUATION 5:}$$

Applying the quadratic formula (X=[−B±SQRT(B²−4AC]/2A) to Equation 3-5 and taking a physically reasonable root gives Equation 3-6:

$$X_d=[X_t+1/(4*K)-SQRT(X_t/(2*_K)+1/(16*K*A))]/2 \quad \text{EQUATION 6}$$

Where SQRT ( ) indicates taking the square root of the content of the parentheses. The fluorescence values at $\lambda_{em}$ 530 nm ($F_{530}$) is a function of $X_t$ and $F_{530}=X_d*\epsilon$, where "$\epsilon$" is the fluorescence yield of the dimer. The equation was solved by non-linear least squares using Prism™ software and binding constants determined. Concentrations of the reactants were adjusted for dilution whereas AO concentrations are reported without adjustment for dilution. Fluorescence values ($f_i$) are reported as raw data normalized to scale and not adjusted by a dilution factor following aliquot additions. Absorbance data taken at 468 nm was also used to calculate the $K_{assoc}$ for the AO-AO dimer using Equation 6.

In still another implementation, AO is known to exhibit two $\lambda_{max}$ fluorescence peaks, depending upon the type of interaction it has with itself or other compounds. For example, when AO intercalates into DNA, presumably by forming a B-B interaction or stacking complex, it has a characteristic green fluorescence maximum at about $\lambda_{em}$ 526 nm. Alternatively, when AO associates with other compounds electrostatically (ionic) through charge transfer it has a characteristic fluorescence maximum at about $\lambda_{em}$ 650 nm. The two emission wavelengths, $\lambda_{em}$ 635 nm and $\lambda_{em}$ 530 nm, represent the approximate $\lambda_{max}$ for the fluorescence emission of AO when electrostatically associated with other compounds (635 nm) and in a stacked (B-B) association with itself or another compound or compounds (530 nm).

Optical absorbance of AO at various concentrations indicates that AO dissolved in 5 mM HEPES solution buffered at pH 7.0 has two spectral peaks (FIG. 3-1A). In the example shown in FIG. 3-1A, absorbance was scanned between 400 nm and 550 nm over a range of AO concentrations from 2.5 μM to 20 μM in a 5 mM solution of HEPES buffer at pH 7.0. The concentration of AO for each spectrum is indicated in the legend by number. Note that the absorbance at 492 nm ($A_{492}$) is indicative of the concentration of the AO monomer, whereas the absorbance at 468 nm ($A_{468}$) is indicative of the concentration of the AO-AO dimer (Kapuscinski and Kimmel, 1993). AO at a concentration of 2.5 μM exhibits a distinct spectrum with a $\lambda_{max}$ of 492 nm. At increasing concentrations of AO, a secondary spectral peak at 468 nm became more distinct and increased in amplitude. When the ratio of the change in absorbance value at 492 nm over the change in absorbance values at 468 nm was plotted versus AO concentrations ranging from 2.5 μM to 20 μM a significant ($R^2=0.99$) linear correlation indicating a relationship between the formation of AO dimers as a function of AO concentration resulted.

The example in FIG. 3-1B shows the same optical absorbance of AO at various concentrations under the same conditions except with addition of 150 mM NaCl. The absorbance was scanned between 410 nm and 540 nm over a range of AO concentrations from 10 μM-45 μM in a 5 mM solution of BEPES buffer at pH 7.0 in the presence of 150 mM of NaCl. The concentration of AO for each spectrum is indicated by arrow. Note that the magnitude of the absorbance at 492 nm ($A_{492}$) decreases in relation to the absorbance at 468 nm ($A_{468}$), as a function of AO concentration. Thus, the presence of 150 mM NaCl in solution causes an overall decrease in the raw absorbance values. In addition, the presence of a physiological concentration NaCl significantly increased the absorbance peak at 468 nm indicating an increase in the concentration of AO dimer in the presence of NaCl.

The fluorescence characterization of AO at low concentrations [0.5-10 μM] is illustrated in example of FIG. 3-2A, wherein the spectrofluorometric analysis was performed at $\lambda_{ex}$ 485 nm and emission was observed at $\lambda_{em}$ 530 nm and $\lambda_{em}$ 635 nm. The error bars shown standard deviation unless obscured by legend symbols (n=4). The results also indicate the effect of a physiological concentration of NaCl [150 mM] on the fluorescence of AO at both $\lambda_{em}$ 530 nm (green) and $\lambda_{em}$ 635 nm (red) over a range of AO concentrations from 0.5 μM to 10.0 μM. At an AO concentration of between 5-6 μM, the amplitude of green fluorescence at $\lambda_{em}$ 530 nm increases abruptly. The red fluorescence ($\lambda_{em}$ 635 nm) also increases abruptly between 5-6 μM. However, the magnitude of the increase at $\lambda_{em}$ 635 nm is proportionally less than that found at $\lambda_{em}$ 530 nm. As the concentration of AO increases from 5 μM to 6 μM, the mean fluorescence values were changed from 457±16 to 5,197 ±289 at $\lambda_{em}$ 530 nm and from 174±4 to 1,371±41 at $\lambda_{em}$ 635 nm (n=4). At AO concentrations from 0.5 μM to 5 μM, the addition of NaCl [150 μM] significantly increases green fluorescence at $\lambda_{em}$ 530 nm, whereas no significant change in the mean fluorescence values was observed at $\lambda_{em}$ 635 (see FIG. 3-2B). The example shown in FIG. 3-2B depicts the binding plot calculated at $\lambda_{em}$ 530 nm for the molecular association of AO with itself in the absence of and in the presence of NaCl. The association constants ($K_{assoc}$) for AO derived from these two plots are 118,000±16,120 $M^{-1}$ ($R^2=0.98$) in the presence of NaCl [150 mM] and 37,410±4, 758 $M^{-1}$($R^2=0.97$) in the absence of NaCl. Error bars denote standard deviation unless hidden by legend symbols (n=4). The presence of 150 mM NaCl has no significant effect on the fluorescence intensity of AO at either $\lambda_{em}$ 530 nm or $\lambda_{em}$ 635 nm at AO concentrations of 6 μM and above.

Association constants were calculated for AO self-association by assuming the fluorescence values derived at $\lambda_{em}$ 530 nm reflect the extent of dimer formation. Association constants ($K_{assoc}$) were calculated from the change in mean fluorescence values (delta fluorescence) at $\lambda_{em}$ 530 nm (see FIG. 3-2B). At AO concentrations from 0.5 μM to 5 μM, $K_{assoc}$ was determined to be 37,410±4,758 $M^{-1}$ ($R^2=0.97$) in the absence of NaCl and 118,000±16,120 $M^{-1}$ ($R^2=0.98$) in the presence of 150 mM NaCl (see FIG. 3-2B). For AO concentrations >5 μM, the association constants were determined to be 46,700±1,807 $M^{-1}$ ($R^2=0.99$) for AO alone and 41,820±3,671 $M^{-1}$ ($R^2=0.99$) for AO in the presence of NaCl. This indicates a significant AO concentration dependent difference in the association constant in the presence of 150 mM NaCl at low AO concentrations (<5 μM) but not a significant difference at AO concentrations above 5 μM.

Results of the optical titration of 10 μM AO with CAF over a range of 0 to 4.5 mM are depicted in FIG. 3-3. The spectrophotometric analysis shown in the example of FIG. 3-3 was performed on a 10 μM solution of AO in 5 mM HEPES buffered at pH 7.0. CAF was titrated into the cuvette containing the AO solution in aliquots of 20 μl taken from a 50 mM stock solution, thus increasing the CAF concentration in increments of 0.5 mM. Absorbance values were corrected to account for dilution. The initial spectrum of 10 μM AO in the absence of CAF (A) gave a $\lambda_{max}$ of 492 nm. With increasing concentration of CAF, the $\lambda_{max}$ of the AO-CAF spectrum shifted to 500 nm at a final CAF concentration of 4.5 mM (B).

The spectrum shown in FIG. 3-3 exhibits a maximum absorption band in the visible region at 492 nm. Upon addition of CAF, the optical absorbance maximum of AO shifts from 492 nm to 500 nm. This red-shift provides the basis for a method to determine the association constant ($K_{assoc}$) for the complex formed between AO and CAF. This method is demonstrated in FIG. 3-4, which displays the optical absorbance difference spectrum (delta absorbance) of the AO-CAF complex. The delta absorbance values for the example shown in FIG. 3-4 were taken at $\lambda_{max}$ 511 nm. Note the presence of a single isobestic point at 500 nm. The inset shows a plot of CAF concentration versus delta absorbance depicts the binding curve for the formation of the AO-CAF complex. To determine the association constant for the AO-CAF complex, delta absorbance values were taken at $\lambda_{max}$ 511 nm and plotted against the concentration of CAF. The delta absorbance spectrum displays a single isobestic point characteristic of only two absorbing species in solution and a maximum deviation peak at $\lambda_{max}$ 511 nm. The calculated $K_{assoc}$ for the AO-CAF complex was found to be 255±5 $M^{-1}$ ($R^2=0.997$) and a 1:1 stoichiometry. The AO-CAF binding plot depicted in the INSET to FIG. 3-4 fits well to a model in which AO and CAF form a 1:1 complex.

Spectrofluorometric analysis was performed at an AO concentration of 2 μM to determine the effect of CAF and a physiological concentration of NaCl on the fluorescence spectra of AO. CAF was added over a series of CAF:AO molecular ratios ranging from 2500:1 to 0.5:1 and the fluorescence intensity determined at $\lambda_{em}$ 530 nm and 635 nm. The fluorescence intensity was again determined following the addition of NaCl to a final concentration 150 mM and pH 7.0 to each test well containing both AO and CAF.

The data in FIG. 3-5A depicts the mean fluorescence values at $\lambda_{em}$ 530 nm of 2 μM AO with CAF in the absence of, and in the presence of, 150 mM NaCl over a range of CAF to AO molecular ratios from 0.5 to 10.0 (1 μM to 20 μM CAF). The example shown in FIG. 3-5A is a plot of fluorescence intensity of AO excited at $\lambda_{ex}$ 485 nm and monitored at $\lambda_{em}$ 530 nm versus CAF concentration to show the effect of CAF and NaCl on the fluorescence of AO and the formation of the AO-CAF complex. Solutions of 2 μM AO were analyzed using spectrofluorometric techniques in the presence of various concentrations of CAF with and without addition of NaCl [150 mM]. Error bars indicate standard deviation unless hidden behind the symbol (n=3). The initial fluorescence values for AO at a concentration of 2 μM with and without 150 mM NaCl differed significantly prior to titration with CAF. Specifically the presence of NaCl in the 2 μM AO solution significantly increased the fluorescence value at $\lambda_{em}$ 530 nm from a mean of approximately 400 to approximately 500. However, upon the addition of increasing amounts of CAF the mean fluorescence values increased significantly over the initial mean fluorescence values. The addition of 150 mM NaCl to the series of AO-CAF solutions did not significantly effect (p>0.05) the mean fluorescence values over the full range of CAF concentrations tested up to a CAF:AO ratio of 1000. However at the CAF concentration of 5 mM (molecular ratio 2,500:1) there was a significant change in the mean fluorescence intensity with the value going from 1,245±53 for CAF and AO alone to 1,150±34 with the addition of 150 mM NaCl. The gradual change in fluorescence intensity at $\lambda_{em}$ 530 run went from a mean value of 671 ±109 (n=3) at a CAF:AO ratio of 0.5 (1 μM CAF) to a value of 1,245±53 at a molecular ratio of 2,500 (5 mM CAF). The mean values in fluorescence intensity that resulted with the addition of either CAF or CAF with NaCl to AO [2 μM] did not significantly differ from each other in mean fluorescence values at $\lambda_{em}$ 635 nm for most test conditions.

Mean spectrofluorometric values were plotted against CAF concentration (see FIG. 3-5B) to determine an association constant ($K_{assoc}$) for the AO-CAF complex in the absence of and in the presence of 150 mM NaCl. The example association curves of FIG. 3-5B were plotted from net fluorescence values (minus background fluorescence) versus CAF concentration. This delta fluorescence plot was used to determine $K_{assoc}$ for the AO-CAF complex at an AO concentration of 2 μM in the absence and presence of 150 mM NaCl. $K_{assoc}$ for the AO-CAF complex at 2 μM AO was found to be 254±27 $M^{-1}$ ($R^2$=0.89) in the absence of 150 mM NaCl and 216±20 $M^{-1}$ ($R^2$=0.93) in the presence of NaCl. The association constant for the formation of the AO-CAF complex at an AO concentration of 2 μM was determined to be 254±27 $M^{-1}$ and 216±20 $M^{-1}$ in the absence of and in the presence of NaCl respectively. These mean value differences are statistically significant.

Experiments were undertaken to characterize the interaction of AO with DNA over a range of DNA base pairs (bp) to AO ratios in the absence of, and in the presence of, a physiological concentration of NaCl. As the ratio of bp to AO increased from approximately 0.4 to 0.65, an overall drop in absorbance values between the wavelengths of 450 nm and 525 nm occurred (FIG. 3-6). The example shown in FIG. 3-6 is a dsDNA bp: AO ratio of selected spectra denoting important transitions within the titration series are denoted with bolder lines. Some of the spectral series is not shown to simplify the data presentation. At bp: AO ratios between 0.0 and 0.75, prevalent peaks occur at $8_{abs}$ of 468 nm and 492 nm. These peaks correspond to the prevalent absorbance peaks found at concentrations of AO at 10:M and higher concentrations. The absorbance spectra from bp: AO ratios above 0.75 denote a definitive red-shift in absorbance with the simultaneous creation of two distinct peaks, one at 475 nm and the other at 503 nm.

With continued additions of aliquots of DNA, the absorbance peak near 468 nm is still apparent while the initial main absorbance peak at 492 nm is minimally detectable. Additionally, with the continued additions of aliquots of DNA and the subsequent increase in the bp:AO ratio above 0.65, the absorbance at $\lambda_{abs}$ 475 nm began to increase and to display a red shift from 468 nm to 475 nm. This spectral peak at $\lambda_{abs}$ 475 nm gradually increased in height with increasing DNA concentration before reaching an absorbance plateau at a bp:AO ratios of 3.0 and above. Additionally, at bp:AO ratios of about 1.72. The absorbance peak near $\lambda_{abs}$ 503 nm increased in amplitude with each additional aliquot of DNA. This absorbance at $\lambda_{abs}$ 503 nm steadily increased throughout the range of titrations from a bp:AO ratio of 1.72 to 9.13. Table 3-1 is a summary and description of the optical absorbance peaks observed during the titration of 100 μM AO with dsDNA and the range of bp:AO molecular ratios over which these absorbance peaks were observed during the titration series. The data reported in Table 3-1 were confirmed with additional serial titrations of AO at 3 μM, 5 μM, 10 μM, and 20 μM. In another example, titrations at AO concentrations of 3 μM, 5 μM, 10 μM, and 20 μM yielded similar results.

TABLE 3-1

Summary and description of optical absorbance maxima peaks observed during the titration of 100 μM acridine orange (AO) with dsDNA and the range of bp:AO molecular ratios over which these absorbance peaks were observed during the titration series.

| $\lambda_{max}$ Absorbance | bp:AO Ratio |
|---|---|
| 468 nm | <0.09-2.99 |
| 475 nm | 1.72-9.13 |
| 492 nm | <0.09-0.53 |
| 503 nm | 0.97-9.13 |

Spectral data from the titration of 3 μM AO with dsDNA was used to generate the delta absorbance plot shown in FIG. 3-7. The results indicate a single isobestic point at 470 nm. The association constant was calculated from a plot of delta absorbance values at 504 nm versus DNA concentration (see inset FIG. 3-7). The DNA concentrations ranged from 30:M to 170:M. The $K_{assoc}$ from this plot was 37,660±431 $M^{-1}$.

In another implementation, a spectrofluorometric analysis of the interaction of AO with dsDNA at $\lambda_{ex}$ 485 nm and $\lambda_{em}$ 530 nm and 635 nm was also conducted. The interaction of DNA with lower concentrations of AO [2 μM] mimicked the results found at the higher AO concentration of 20 μM for bp:AO ratios of 4:1 and above. The association curve for AO over a series of steadily increasing DNA concentrations ranging from 8 to 250 μM of DNA is shown in FIG. 3-8.

The example shown in FIG. 3-8 illustrating the effect of NaCl on the fluorescence of 2 µM AO was determined over a range of bp:AO ratios from 4 to 62.5. The excitation wavelength was 485 nm while emission was monitored at 530 nm. The association constant for 2 µM AO with DNA was determined to be 31,990±310 M$^{-1}$ (R$^2$=0.98) in the absence of NaCl and 31,690±498 M$^{-1}$ (R$^2$=0.96) in the presence of NaCl. Error bars are shown to denote confidence intervals at 95% unless hidden by a data point symbol. The delta fluorescence values were obtained by subtracting the background fluorescence of HEPES buffered AO at 2 µM in the absence of DNA. The association constant for the interaction of AO with DNA was determined to be 31,990±3,190 M$^{-1}$. As also illustrated in FIG. 3-8, the addition of 150 µM NaCl to the initial 2 µM AO solution had little if any effect on the binding constant between AO and the dsDNA resulting in a value of 31,690±4,980 M$^{-1}$.

Experiments were conducted to determine the effect of physiological concentrations of NaCl on the fluorescence intensity of the AO-DNA complex. FIG. 3-9 depicts the spectrofluorometric analysis of AO at concentrations ranging from 0.5 to 10.0 µM with 20 µM DNA in the presence of, or in the absence of, 150 mM NaCl. Samples were excited at a wavelength of 485 nm and fluorescence emission values were read at $\lambda_{em}$ 530 nm and $\lambda_{em}$ 635 nm. Error bars shown denote standard deviation unless hidden by legend symbols (n=4). Spectrofluorometric analyses of 20 µM DNA at AO concentrations ranging from 0.5 to 3.0 µM revealed a slight, but significant, increase in fluorescence values at $\lambda_{em}$ 530 nm over this concentration range of AO. The addition of NaCl [150 µM] to the environment containing AO and DNA, did not contribute significantly to the fluorescence values at either $\lambda_{em}$ 530 nm or $\lambda_{em}$ 635 nm until AO concentrations exceeded 2 µM as determined by ANOVA statistics. At AO concentrations above 3.5 µM, the fluorescence values of the DNA solution at $\lambda_{em}$ 530 nm in the absence of, and in the presence of, NaCl increased 4 and 5-fold, respectfully. In the absence of NaCl, the plot of fluorescence values at $\lambda_{em}$ 530 run plateaus at AO concentrations ranging from 4.0 to 7.0 µM. Also, the data in FIG. 3-9 reveals that the fluorescence values in the presence of 150 mM NaCl over the AO concentration range 4.0 to 7.0 µM, differed significantly (were increased) from the values obtained at $\lambda_{em}$ 530 nm in the absence of NaCl. At $\lambda_{em}$ 635 nm, fluorescence values increased slightly between AO concentrations of 3.5 to 4.0 µM and continued to gradually rise with increasing concentration of AO. Unlike the results obtained at $\lambda_{em}$ 530 nm, the presence of, or the absence of, NaCl had no significant effect on the fluorescence at $\lambda_{em}$ 635 nm.

The addition of salt could possibly affect the K$_{assoc}$ values of AO and the other reactants by modifying the charge on the reactants and/or decreasing the influence of water molecules. To minimize AO self-association, i.e. dimerization, a relatively low concentration of AO [2 µM] may be used. The interaction between reactants was analyzed by spectrofluorometric methods at $\lambda_{ex}$ 485 nm and monitored at $\lambda_{em}$ 530 nm (green).

Solutions of 2 µM AO alone and in various combinations with 150 mM NaCl, 5 mM CAF, 2 mM DNA were studied. Table 3-2 summarizes the results and the statistical analysis for differences between means.

TABLE 3-2

The effect of 150 mM NaCl, 5 mM caffeine, and/or 2 mM dsDNA on the fluorescence of a 2 µM acridine orange solution.

| Reactants (2 µM AO) | Without NaCl Mean ± S.E. (SNK) | With NaCl [150 mM] Mean ± S.E. (SNK) |
| --- | --- | --- |
| AO* | 514.0 ± 6.5 (A) | 635.5 ± 17.7 (B) |
| AO + CAF | 661.0 ± 19.3 (B) | 701.3 ± 53.7 (B) |
| AO + DNA | 988.0 ± 11.1 (E) | 795.0 ± 17.7 (C) |
| AO + DNA + CAF | 880.3 ± 27.6 (D) | 793.7 ± 14.4 (C) |

In Table 3-2, fluorescence ($\lambda_{ex}$=485 nm and $\lambda_{em}$=530 nm) was measured for AO [2 µM] in the absence of, and in the presence of, NaCl [150 mM], caffeine [5 mM], and DNA [2 mM] alone or in combination. Significant differences were found by one-way ANOVA (p≦0.05). The Student-Newman-Keuls (SNK) multiple range test revealed a significant difference between means (p≦0.05), as indicated in the table. Statistical means having a different letter designation are statistically different (p<0.05) while those means having the same letter are not significantly different (p>0.05). It is noted that n=3 unless denoted by an * which indicates n=4.

The results, as reported in Table 3-2, fell into five distinct groups, each designated by a different capitalized letter, with statistically different means (p<0.05). The lowest mean fluorescence value of 514.0 was produced by 2 µM AO alone. Addition of 150 mM NaCl to 2 µM AO caused a significant increase in the mean fluorescence value from 514.0 to 635.5. This value of 635.5 was not significantly different from either the mean fluorescence value of 661.0 determined for AO in the presence of 5 mM CAF or the mean fluorescence value of 701.3 determined for AO in the presence of both 5 mM CAF and 150 mM NaCl. The addition of 2 mM DNA to the 2 µM AO solution caused the highest mean fluorescence value of 988.0, which was almost double the mean fluorescence value of 514.0 determined with AO alone. Yet, this value of 988.0 was significantly higher than the value of 795.0 obtained with the addition of 150 mM NaCl to the AO-DNA solution.

The fluorescence of 2 µM AO at 8$_{em}$ 530 nm was increased 92% by the addition of 2 mM DNA and by 29% by the addition of 5 mM CAF. The presence of 150 mM NaCl further increased the fluorescence intensity of AO in the presence of CAF. The addition of NaCl significantly reduced the ability of DNA to increase the fluorescence intensity of AO. Therefore, the addition of either DNA or CAF when in the presence of 150 mM NaCl resulted in an increase in fluorescence intensity of AO by 54% and 36%, respectively.

The results from the previously described experiments characterize the specific interactions of AO to each of the binding species, CAF or dsDNA individually, while keeping the concentration of AO fixed at 2µM.

Spectrofluorometric analyses at $\lambda_{ex}$ 485 nm and $\lambda_{em}$ 530 nm were performed on solutions of 2:M AO in combination with 5 mM CAF and 2 mM dsDNA, with and without 150 mM NaCl. Statistical analysis of these results are also reported in Table 3-2. Means with different letter designations are statistically different (p<0.05) while means containing the same letter designation had means that were not significantly different. Manipulation of the AO-DNA solution by the addition of 5 mM CAF significantly lowered (p<0.05) the mean fluorescence value from 988.0 to 880.3. Yet, this value of 880.3 was significantly higher than the value of 795.0 obtained with the addition of only 150 mM NaCl to the same AO-DNA solution. Note that CAF had no significant effect on the fluorescence of the AO solution when in the presence of NaCl (SNK letter designation "B"). The combination of 2 mM DNA, 5 mM CAF, and 150 mM NaCl with AO gave a mean fluorescence value of 793.7 that was not significantly different from the mean value of 795.0, obtained for AO in the presence of 2 mM dsDNA plus 150 mM NaCl but in the absence of CAF.

Bound AO is known to fluoresce at two distinct wavelengths based on the type of molecular association that occurs. When AO binds electrostatically to a compound (e.g. RNA), it has a characteristic red fluorescence with $\lambda_{max}$ emission of 635 nm. Alternatively, when AO intercalates, as occurs with DNA, it fluoresces green at a $\lambda_{max}$ of 530 nm (Haugland, 1994). The fluorescence of free unbound AO monomer is weak at low concentrations (1-10 μM and, therefore, contributes little to background fluorescence. The electrostatic interaction of AO with itself can, therefore, be monitored at $\lambda_{em}$ of 635 nm while the formation of a stacked dimer can be followed by monitoring the fluorescent emission at 530 nm.

concentration, AO exists primarily as a monomer with an increased formation of its dimer species as the concentration of AO increases toward 5 μM. At concentrations above 5 μM, molecular AO exists in solution as a monomer, a dimer, and possibly as unstacked aggregates of dimers. Fluorescence analysis allowed for the clear distinction and specific monitoring of the dimeric and monomeric forms of the AO molecule.

The optical titration and spectral analysis studies of CAF with the DNA-intercalator AO demonstrates that CAF can complex with AO via a B-B type interaction. An important force in the formation of such complexes appears to be van der Waals interactions resulting in maximal ring overlap between the two molecules of the complex. Complexation between CAF and aliphatic mutagens show much lower binding energies relative to CAF complexes with aromatic intercalators. The corresponding binding constant for CAF-AO complexes is on the order of 250 $M^{-1}$ (Table 3-3). In Table 3-3, absorbance was scanned between 400 nm and 550 nm. Fluorescence excitation was at 485 nm whereas emission was observed at 530 nm.

TABLE 3-3

Summary of association constants ($K_{assoc}$) for acridine orange (AO) with itself, with caffeine (CAF), and with dsDNA in the absence of and in the presence of 150 mM NaCl.

| Complex | Method | K ± S.D. [$M^{-1}$] | Concentration | Source |
|---|---|---|---|---|
| AO-AO | Absorbance[a] | 29,100 | AO [20 μM] | Kapuscinski & |
|  | plus NaCl[b] | 42,500 |  | Kimmel, 1993 |
|  | Absorbance | 46,840 ± 5,967 | AO [2.5-20 μM] | This study |
|  | plus NaCl | 47,510 ± 2,420 | AO [10-45 μM] | " |
|  | Absorbance | 49,530 ± 2,953 | AO [10-80 μM] | This study |
|  | Fluorescence | 37,410 ± 4,758 | AO [0.5-5.0 μM] | This study |
|  | plus NaCl | 118,000 ± 16,120 | AO [0.5-5.0 μM] | " |
|  | Fluorescence | 46,700 ± 1,807 | AO [6.0-10.0 μM] | This study |
|  | plus NaCl | 41,820 ± 3,671 | AO [6.0-10.0 μM] | " |
| AO-CAF | Absorbance | 256 ± 5 | AO [10 μM]; CAF [1-5000 μM] | This study |
|  | Absorbance | 258 ± 5 | AO [10 μM]; CAF [1-5000 μM] | Larsen et al., 1996 |
|  | Absorbance | 258 ± 7 | AO [20 μM]; CAF [1-2000 μM] | Kapuscinski & |
|  | plus NaCl[b] | 169 ± 9 | AO [20 μM]; CAF [1-2000 μM] | Kimmel, 1993 |
|  | Fluorescence | 254 ± 27 | AO [2 μM]; CAF [1-20 μM] | This study |
|  | plus NaCl | 216 ± 20 | AO [2 μM]; CAF [1-20 μM] | " |
| AO-DNA | Absorbance | 33,510 ± 285 | AO [0.1-3 μM]; DNA [100 μM] | This study |
|  | Absorbance | 31,960 ± 316 | AO [0.8-3.4 μM]; DNA [20 μM] | " |
|  | Absorbance | 37,660 ± 431 | AO [3 μM]; DNA [5-170 μM] | " |
|  | Fluorescence | 31,990 ± 3,190 | AO [2 μM]; DNA [>20 μM] | " |
|  | plus NaCl | 31,690 ± 4,890 | AO [2 μM]; DNA [>20 μM] | " |

[a]$K_{assoc}$ calculated using absorbance data and a mathematical model.
[b]NaCl concentration of 150 mM The increase of NaCl concentration to 150 mM resulted in an increase in the optical absorbance at 268 nm in relationship to the absorbance at 491 nm indicative of an increase in the concentration of dimer in solution. Also, the addition of 150 mM NaCl resulted in an increase in $K_{assoc}$ from 37,410 $M^{-1}$ to 118,000 $M^{-1}$ at AO concentrations ranging from 0.5 μM to 5.0 μM.

In summary, the formation of the dimer or stacked AO aggregate is dependent, in part, upon the concentration of AO. The addition of salt to AO solutions facilitates dimer formation at lower AO concentrations but has minimal additional effects at AO concentrations above 5 μM. The sharp increase in green fluorescence ($\lambda_{em}$ 530 nm) at an AO concentration of 5 μM is probably due to a shift in AO equilibrium toward the formation of AO dimers. The critical concentration for this phenomenon seems to be approximately 5-6 μM. Below this The spectrophotometric analysis of the AO-DNA binding reported herein suggests the presence of a single bound species at high DNA to AO ratios and, therefore, only one mode of binding (a single isobestic point could be easily identified during the spectrophotometric analysis only at DNA to AO molecular ratios above 5.0). The measurement of an association constant or 'affinity' for the AO-DNA system, under such conditions, was assessed by both absorbance studies and fluorescence studies and the $K_{assoc}$ values were found to be similar (Table 3-3).

Data from optical titrations suggest that the AO-AO self-stacking or dimer formation is practically eliminated at high DNA to AO ratios. These data suggest that the binding process for AO to DNA at lower molecular ratios can be divided into two different processes as has been described for most of the acridine derivatives: one of high affinity (type I) and one of lower affinity (type II). The type I process is strong and corresponds to the intercalation of the AO into the DNA double helix at low binding ratios. Type II process is weak and is normally attributed to an external electrostatic binding at high binding ratios. The use of different fluorescence emission wavelengths allowed for the calculation of association constants for each kind of binding involved in the interaction process. Therefore, binding values determined from data obtained at $\lambda_{em}$ 530 nm should be considered as relative to the intercalation or B-B binding (stacking) of AO to DNA. The $K_{assoc}$ values obtained at low AO to DNA ratios (intercalation process) suggest that the fluorometric determination at $\lambda_{em}$ 530 nm only allows the calculation for the type I strong binding mode association constant.

At low DNA to AO molecular ratios, a decrease in the fluorescence intensity of AO was observed when interacting with DNA. AO has a strong binding affinity for DNA, especially at low AO concentrations. This behavior is sensitive to the concentration of the acridine chromophore as stronger binding between AO and DNA is seen at lower ratios of AO to DNA base pairs (AO concentrations <3 μM).

An increase in NaCl concentration to 150 mM resulted in an increase in $K_{assoc}$ for the dimerization of AO from 37,410 $M^{-1}$ to 118,000 $M^{-1}$ at AO concentrations ranging from 0.5:M to 5.0 :M (inset to FIG. 3-2). This is likely attributed to the stabilization of the AO-AO dimer by decreasing the contribution of water molecules to the solvation of the AO monomer by competing with the electrostatic charge due to the protonization of the nitrogen on AO. Thus the higher $K_{assoc}$ value in the presence of 150 mM NaCl is expected to shift the equilibrium between monomeric AO and dimeric AO to favor the formation of AO dimers. Even at relatively low AO concentrations [2 μM], physiological concentrations of NaCl caused a 23% increase in fluorescence values at $\lambda_{em}$ 530 nm, indicative of an increase in dimer formation (see Table 3-2).

The solution containing AO and DNA gave a fluorescence value almost double that of AO alone (Table 3-2) reflecting the high degree to which AO intercalated into the DNA. The addition of 150 mM of NaCl to a solution containing the AO and DNA caused a 20% reduction in the fluorescence of the solutions In solutions containing NaCl, an increase in the ionic strength causes DNA to lose some of its ability to form electrostatic bonds with AO. At a molecular ratio of 1000:1 (2 mM DNA: 2 μM AO), this should have little if any effect on the fluorescence intensity of the AO-DNA complex. The addition of NaCl causes a shift in the amount of free AO monomer available for intercalation into DNA by increasing the concentration of AO-AO dimer. This increase in the formation of AO-AO dimers would cause a decrease in fluorescence intensity by reducing the concentration of AO-DNA complexes formed by a ratio of 2 to 1 for every dimer formed.

In a solution containing all three reactants, the equilibrium in the AO-CAF-DNA system is controlled by four parameters, i.e., $K_{AO-AO}$, $K_{AO-CAF}$, $K_{AO-DNA\ (i)}$, and $K_{AO-DNA\ (e)}$ which represent (at AO>5 μM) the association constants for AO-AO, AO-CAF, AO-DNA (intercalation), and AO-DNA (electrostatic) respectfully. The $K_{eq}$ for the system would be:

$$K_{eq} = K_{AO-AO} + K_{AO-CAF} + K_{AO-DNA\ (i)} + K_{AO-DNA\ (e)}$$

At any given concentration of AO, at constant temperature, pH, and pressure, $K_{eq}$ is a constant. Changes in the $K_{assoc}$ values for AO-AO, AO-CAF, or AO-DNA$_{(i/e)}$ will not affect the overall $K_{eq}$ of the system, but will instead affect the $K_{assoc}$ values between the other reactants. Results from the interaction of all three reactants in the absence of and in the presence of NaCl, support this concept. However, the $K_{assoc}$ values for each reactant reflects the molecular interaction with the AO monomer and assumes that the concentration of AO in solution is entirely in monomeric form. At AO concentrations <5 μM, this is a reasonable assumption and the interpretation of fluorometric measurement of the interactions between AO, dsDNA, CAF, and NaCl are relatively simple. At AO concentrations >5 μM, the assumption that AO is exclusively in monomeric form is invalid. Even at AO concentrations >5 μM, one can still interpret the spectrofluorometric data at $\lambda_{em}$ 530 nm as discussed next.

The model presented in FIG. 3-10 illustrates the molecular populations of AO at 2 μM and at 20 μM. At a concentration of 2 μM, AO is almost exclusively in monomeric form whereas at a concentration of 20 μM, there exists a dynamic equilibrium between the monomeric and dimeric forms. The monomeric form of AO reacts with CAF to form an AO-CAF complex (also shown in FIG. 3-10) and only the monomeric form of AO can intercalate into dsDNA. The availability of monomeric AO is critical to its intercalation into dsDNA and/or its complexation with CAF. Conditions that affect the equilibrium between the dimeric and monomeric forms of AO, such as NaCl, effect the overall concentration and availability of monomeric AO. Table 3-2 shows that the addition of CAF to the AO-DNA system causes a significant decrease in fluorescence with no significant decrease upon the addition of NaCl. This suggests that the relatively high concentration of CAF (5 mM) is able to reduce the amount of AO intercalated into DNA through competitive complexation of monomeric AO, based on the laws of mass action. The addition of CAF to the AO-DNA-NaCl system causes no significant change in fluorescence, because CAF is in a non-charged state and because the $K_{assoc}$ value for the AO-DNA complex is much greater than that for AO-CAF and, therefore, is the primary force controlling the equilibrium and availability of monomeric AO.

The results of these experiments reveal that the interaction of CAF with increasing AO concentration follows the law of mass action in that fluorescence increases proportional to the increase in AO concentration. The addition of dsDNA to the AO-CAF system causes a significant reduction in fluorescence response. This is attributed to the electrostatic bonding of AO to the DNA backbone and, therefore, a reduction in available AO monomers for AO-AO dimerization and for complexation with CAF thus resulting in the lowering of the fluorescence intensity. The addition of NaCl to this system slightly increases the amount of fluorescence along the series of increasing AO concentrations and can be attributed to charge neutralization of the phosphate group on the DNA backbone freeing up monomeric AO as well as the ability of NaCl to stabilize AO-AO dimers. The charge neutralization of the phosphate backbone on DNA also results in an equilibrium shift to more available monomeric AO thus contributing to the formation of AO-CAF complexes and/or AO-DNA intercalation that results in a higher fluorescent intensity.

The use of xanthines is not limited to merely binding to free DNA intercalators. Xanthines can also be used as interceptors of compounds intercalated into DNA. As discussed previously, the law of mass action can be exploited to inhibit the binding of DNA intercalators. In a similar fashion, because the DNA intercalators are in dynamic equilibrium with polynucleotides, the law of mass action can be exploited to remove bound intercalators. Furthermore, the use of the interceptor molecule is not limited to modified xanthines. Any molecule that binds with the DNA intercalator through the law of mass action can be used. Examples include, but are not limited to, purines, pyrimidines, uric acid, porphyrin, polynucleotides, DNA, RNA, PNA, and combinations thereof.

EXAMPLE 4

In another implementation of the invention, the cationic fluorescent dye acridine orange (AO; 3,6-bis[dimethylamino] acridine hydrochloride, >99% purity), was obtained from Aldrich Chemical Company, Milwaukee, Wis., and HEPES buffer was obtained from Mediatech, Inc., Herndon, Va. Highly polymerized herring sperm deoxyribonucleic acid sodium salt was obtained from ACR_S Organics, Pittsburgh, Pa. was used without further purification. Caffeine (CAF; 1,3,7-trimethyl xanthine, Aldrich), and three other methylated xanthines, 1,7-dimethyl xanthine, theophylline (3,7-dimethyl xanthine, ACR_S) 1,3,7,9-tetramethyl-8-oxy xanthine (TMU; tetramethyl uric acid, ICN Biomedicals, Inc., Aurora, Ohio), aminophylline (theophylline ethylenediamine) were also obtained commercially at 99% purity and used without further purification. Stock solutions of CAF and AO were prepared at a concentration of 50 mM. A stock solution of herring sperm DNA was prepared fresh the day of use. The concentration for dsDNA was based on the average molecular weight of all four nucleoside bases to obtain an approximate formula weight of 340 g/mole (one base) or 680 g/mole (one base pair or "bp"). This method assumed that each base occurs equally within the DNA. Using the formula weight of 340 g/mole, stock solutions of DNA were prepared at a concentration of 5 mM. All solutions and subsequent dilutions were prepared by dissolving the appropriate weighed amount in 5.0 mM HEPES that was adjusted to pH 7.0 with 0.1 M NaOH. AO was prepared in a stock solution at a concentration of 50 mmol in 5 mmol HEPES buffer (1.0 M solution, Mediatech, Inc., Herndon, Va.). AO was chosen as a representative DNA intercalator because of its known spectral characteristics and its wide use as a fluorescence chromophore marker for both DNA and RNA (Robinson et al., 1973; Kapuscinski, 1990; Kapuscinski and Darzynkiewicz, 1987, 1990; von Tscharner and Schwarz, 1979). Specifically, AO exhibits two $\lambda_{max}$ fluorescence peaks, depending upon the type of interaction it has with itself or other compounds (Larsen et al., 1995; Haugland, 1994; Darzynkiewicz et al., 1996). For example, when AO intercalates into DNA, presumably by forming a B-B interaction or stacking complex, it has a characteristic green fluorescence maximum at about $\lambda_{em}$ 526 nm (green). Alternatively, when AO associates with RNA or other compounds electrostatically (ionic) through charge transfer it has a characteristic fluorescence maximum at about $\lambda_{em}$ 650 nm (red). The two emission wavelengths used in this study, $\lambda_{em}$ 635 nm and $\lambda_{em}$ 530 nm, represent the approximate $\lambda_{max}$ for the fluorescence emission of AO when electrostatically associated with other compounds (635 nm) and in a stacked (B-B) association with itself or another compound or compounds (530 nm).

All stock solutions and subsequent dilutions were prepared by dissolving the appropriate weighted amount of compound in 5.0 mmol HEPES adjusted to pH 7.0 with 0.1 M NaOH.

EXAMPLE 5

In another implementation of the invention, depurinated nucleotides can be used as sites that only minimally bind the intercalator acridine orange.

Chicken erythrocytes were chosen as one implementation of this invention. These nucleated cells have mature erythrocytes with no RNA. Blood was taken from a mature chicken. The blood was drawn from a wing vein into 50 ml glass heparin containing tubes to prevent clotting. This blood was used to make smears on microscope slides. These blood smeared slides were allowed to dry at room temperature and were stored in microscope boxes.

Depurination of dsDNA within the nuclear chromatin of chicken erythrocytes was accomplished by using a modification of the Feulgen method (Feulgen and Rossenbeck, 1924). Specifically, the nucleated chicken erythrocyte slide preparations were rinsed in a 1 N solution of HCl at room temperature for 60 seconds. This was followed by placement of the slide in a pre-heated (55° C.) solution of 1 N HCl for 10 minutes under static conditions followed by several rinses in distilled water at room temperature. Slides were allowed to dry at room temperature then stained with AO at two different concentrations, one at 5 mM and the other at 10 µM for 15 min and 2 min, respectively. The depurination of DNA was expected to remove the site on the DNA polymer where AO intercalation can occur.

Solutions of AO were prepared at 5 mM and 10 µM concentrations in distilled water. Microscope slides smeared with chicken erythrocytes were stained by placing the slide into a glass slide holder containing 50 ml of AO solution under static conditions from 2 min to 30 min, followed by three 10 second rinses in distilled water before drying at room temperature. The staining of nuclear chromatin dsDNA of the chicken erythrocyte at high AO to DNA ratios allowed for both the intercalation of AO into dsDNA and for AO to electrostatically bind to the phosphate backbone of the nuclear chromatin dsDNA strand. Alternatively, the staining at low AO to DNA ratios allowed for only intercalation into the dsDNA. Control slides consisted of chicken erythrocyte smeared slides that were subsequently placed in pure distilled water (no stain) prior to drying (negative control) and blank slides (no erythrocytes) placed in AO staining solutions then dried. Processed slides were stored in the dark then read and photomicrographs taken (Zeiss Model 63 Microscope, 1600 ASA Kodak film) soon after removal from the dark to avoid photobleaching.

Table 4-1 lists the results observed upon staining chicken erythrocyte nuclear chromatin with two different concentrations of AO before and after acid hydrolysis to produce apurinic acid (ap). Results from these experiments show that when the purine bases are removed from dsDNA within the nuclear chromatin, AO is unlikely to form a complex as evidenced by the lack of green fluorescence at $\lambda_{em}$ 530 nm. However, electrostatic binding continues to occur as evidenced by the continued presence of red fluorescence at $\lambda_{em}$ 635 nm.

TABLE 4-1

Color observed upon staining chicken erythrocyte nuclear chromatin with acridine orange before and after acid hydrolysis of dsDNA to apurinic acid (ap) as determined by fluorescence microscopy.

| Chicken Erythrocytes | Fluorescent Color | |
| --- | --- | --- |
|  | 10 µM | 5 mM |
| Chromatin | Green | Red |
| apChromatin | No Color | Red |

In the example shown in Table 4-1, the chicken erythrocytes were smeared and dried on a microscope slide prior to exposure to two different concentrations of AO (10 µM and 5 mM), rinsed with distilled water, and allowed to dry. Erythrocytes were examined with fluorescence microscopy and the color of the nuclei recorded. Xanthine exposure times for 10

μm AO and 5 mM AO were 15 min and 2 min, respectively. The depurinated nucleotides (apChromatin) exhibited essententially no green color in the presence of 10 μM AO illustrating essentially no binding thereto.

EXAMPLE 6

In another implementation of the invention, modified xanthines are used to inhibit the binding of DNA intercalators. By providing an excess of xanthines as compared to DNA intercalators, the binding of these intercalators can be inhibited for more than 10 minutes.

Microscope slides coated with chicken erythrocyte were stained with 10 μM AO at three separate areas on the microscope slide as described above. Slides were exposed to five different xanthies at four different molar ratios for three different periods of time. The xanthines, theophylline, caffeine, 1,3,7,9-tetramethyl uric acid, and aminophylline, were prepared with 10 μM AO at molar ratios of 50:1, 500:1, 2500:1, 5000:1 xanthine to AO in distilled water. Microscope slides coated with chicken erythrocytes were exposed to a mixture of xanthine/AO at each molar ratio for periods of 10 min, 1 min, and 10 seconds under static (non-agitated) conditions. Slides were also treated with mixtures of dsDNA/AO solutions under the same conditions to study the effect of a competitor DNA molecule with a significantly higher $K_{assoc}$ value for AO than the xanthines. Following exposure to the xanthine/AO or to the DNA/AO solutions, the slides were rinsed in distilled water, allowed to dry at room temperature, examined by fluorescence microscopy, and the color of the nuclei recorded. Results were recorded as follows: 0=no blocking effect; 1=slight blocking; 2=moderate blocking; 3=almost total blocking (very slight green fluorescence detectable); 4=complete blockage (no green fluorescence detectable).

Experiments testing the ability of different xanthines with known binding affinities for AO, as well as pure dsDNA, to inhibit the intercalation of AO into chicken erythrocytes chromatin were performed (results summarized in Table 4-2). At AO concentration of 10 μM, xanthines with the highest binding affinity for AO tended to block intercalation relative to the strength of their binding affinity and molar ratio to AO. For example, aminophylline with a $K_{assoc}$ value of 596.2 $M^{-1}$ showed a significant ability to block AO intercalation and to maintain that inhibition even at 10 minutes exposure. The efficacy of blocking was correlated to the molar ratio of aminophylline to AO. As the molar ratio of aminophylline to AO increased by two orders of magnitude from 50:1 to 5000:1 the efficacy of inhibition also increased proportionally. Theophylline, with a binding affinity of 160.8 $M^{-1}$ had minimal effect even at an exposure time of 10 seconds. Exposure to dsDNA with the highest binding affinity to AO (~4000 $M^{-1}$) was more effective than any of the xanthines tested at blocking AO from staining nuclear chromatin.

TABLE 4-2

Effect of increasing exposure time and xanthine concentration on the ability of xanthines with increasing $K_{assoc}$ values for acridine orange to block acridine orange intercalation into chicken erythrocyte nuclear chromatin as determined by fluorescence microscopy.

| Compound | Xanthine/AO | Exposure Time | | |
|---|---|---|---|---|
| ($K_{assoc}$ $M^{-1}$)* | Molar Ratio | 10 min | 1 min | 10 sec |
| Theophylline | 5000:1 | 0 | 0 | 0 |
| (157) | 2500:1 | 0 | 0 | 0 |

TABLE 4-2-continued

Effect of increasing exposure time and xanthine concentration on the ability of xanthines with increasing $K_{assoc}$ values for acridine orange to block acridine orange intercalation into chicken erythrocyte nuclear chromatin as determined by fluorescence microscopy.

| Compound | Xanthine/AO | Exposure Time | | |
|---|---|---|---|---|
| ($K_{assoc}$ $M^{-1}$)* | Molar Ratio | 10 min | 1 min | 10 sec |
|  | 500:1 | 0 | 0 | 0 |
|  | 50:1 | 0 | 0 | 0 |
| Caffeine | 5000:1 | 1 | 2 | 3 |
| (256) | 2500:1 | 0 | 1 | 2 |
|  | 500:1 | 0 | 0 | 2 |
|  | 50:1 | 0 | 0 | 0 |
| 1,3,7,9-Tetramethyl Uric Acid | 5000:1 | 2 | 2 | 2 |
| (552) | 2500:1 | 1 | 1 | 0 |
|  | 500:1 | 0 | 0 | 0 |
|  | 50:1 | 0 | 0 | 0 |
| Aminophylline | 5000:1 | 3 | 3 | 3 |
| (596) | 2500:1 | 1 | 2 | 3 |
|  | 500:1 | 0 | 2 | 2 |
|  | 50:1 | 0 | 0 | 0 |
| DNA | 500:1 | 2 | 3 | 3 |
| (~4000) | 50:1 | 1 | 2 | 3 |
|  | 5:1 | 0 | 0 | 0 |
|  | 1:1 | 0 | 0 | 0 |

In the implementation shown in Table 4-2, the relative intensity of the green fluorescent color ($\lambda_{em}$ 360 nm) utilizing a red blocking filter ($\geq$600 nm) was used as the indicator of the intensity of staining. The molar ratio is expressed as the ratio of xanthine concentration to 10 μM AO. Results were recorded as follows: 0=no blocking effect; 1=slight blocking; 2=moderate blocking; 3=almost total blocking (very slight green fluorescence detectable); 4=complete blockage (no green fluorescence detectable). *$K_{assoc}$ values for the xanthines are taken from Table 2-1 and the $K_{assoc}$ values for DNA were taken from Table 3-2.

The application of this invention is not limited to the modified xanthines tested or to the concentrations used. This invention is applicable to a wide range of modified xanthines, including, but limited to 1-methyl xanthine, 1,3-dimethyl xanthine, 3,7-dimethyl xanthine, 1,7-dimethyl xanthine, 1,3,7-tri-methyl xanthine, 1,3-dimethyl xanthine, 1,3-dimethyl-8-oxy xanthine, 1,3-dimethyl-8-chloro xanthine, and 1,3,7,9-tetramethyl-8-oxy xanthine. Additionally, the excess amount of xanthines need not be limited to that given in Table 4-2. Variations of Xanthine to intercalator ratio are included within the scope of this invention. In addition, an polynucleotide, whether it is DNA, RNA, or PNA may be used in either a single, double, or higher order stranded structure. Furthermore, the use of the interceptor molecule is not limited to modified xanthines. Any molecule that binds with the DNA intercalator through the law of mass action can be used. Examples include, but are not limited to, purines, pyrimidines, uric acid, porphyrin, polynucleotides, DNA, RNA, PNA, and combinations thereof. In addition, this invention also includes the varying the salt concentration as discussed previously to stabilize the dimer fomation of intercalator molecules.

EXAMPLE 7

In still another implementation, the modified xanthine may be used to intercept and remove the an intercalator bound to a DNA complex. For this aspect of the invention, an excess amount of modified xanthines are delivered to the DNA/intercalator complex. Because intercalator molecules are in dynamic equilibrium with the DNA, an excess of modified xanthine can be used to remove the intercalator molecule from DNA/intercalator complex.

Figure 3:
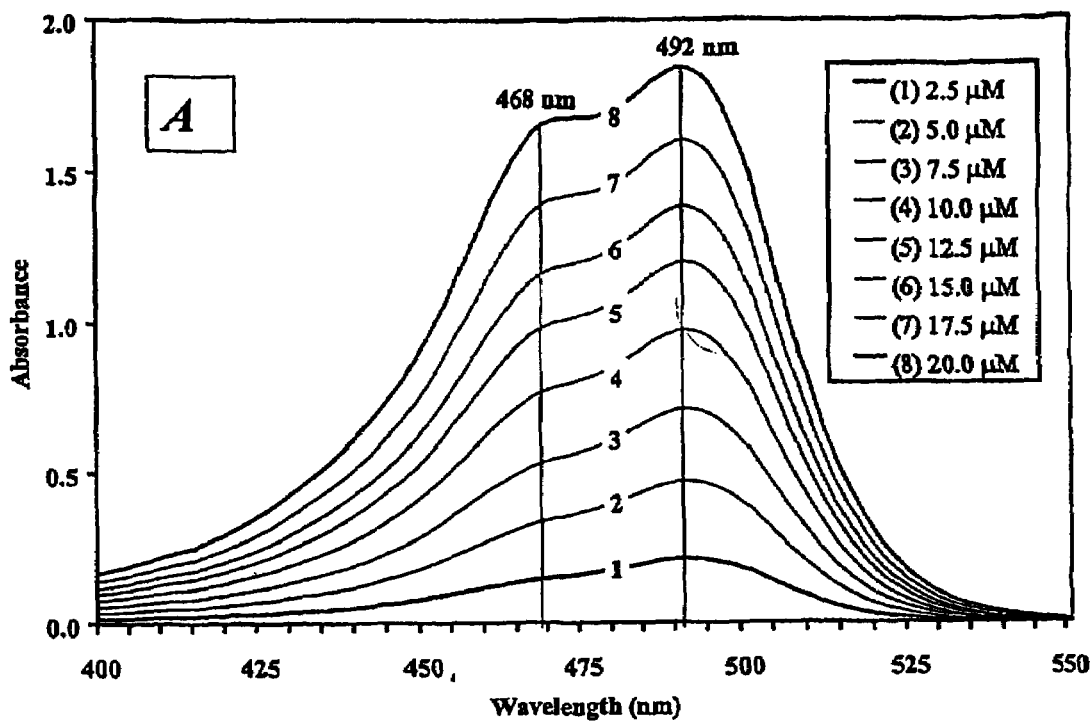
Figure 3:
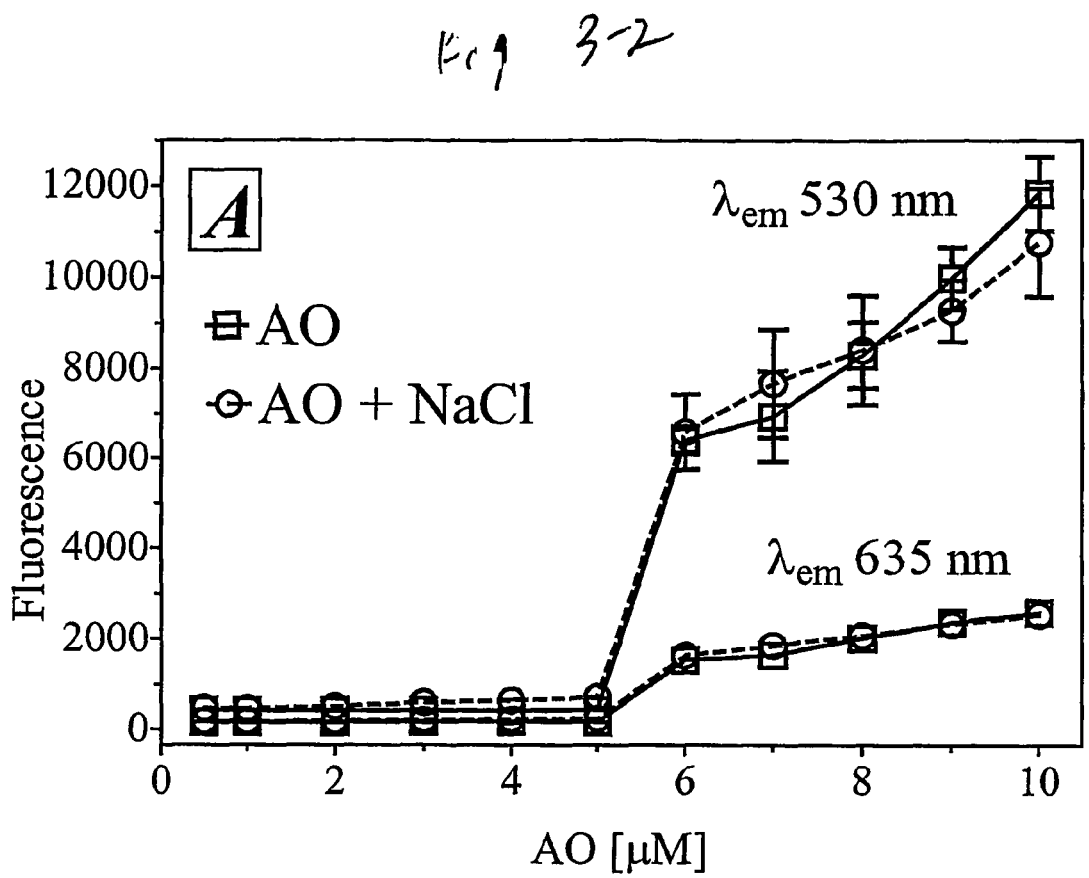
Figure 3:
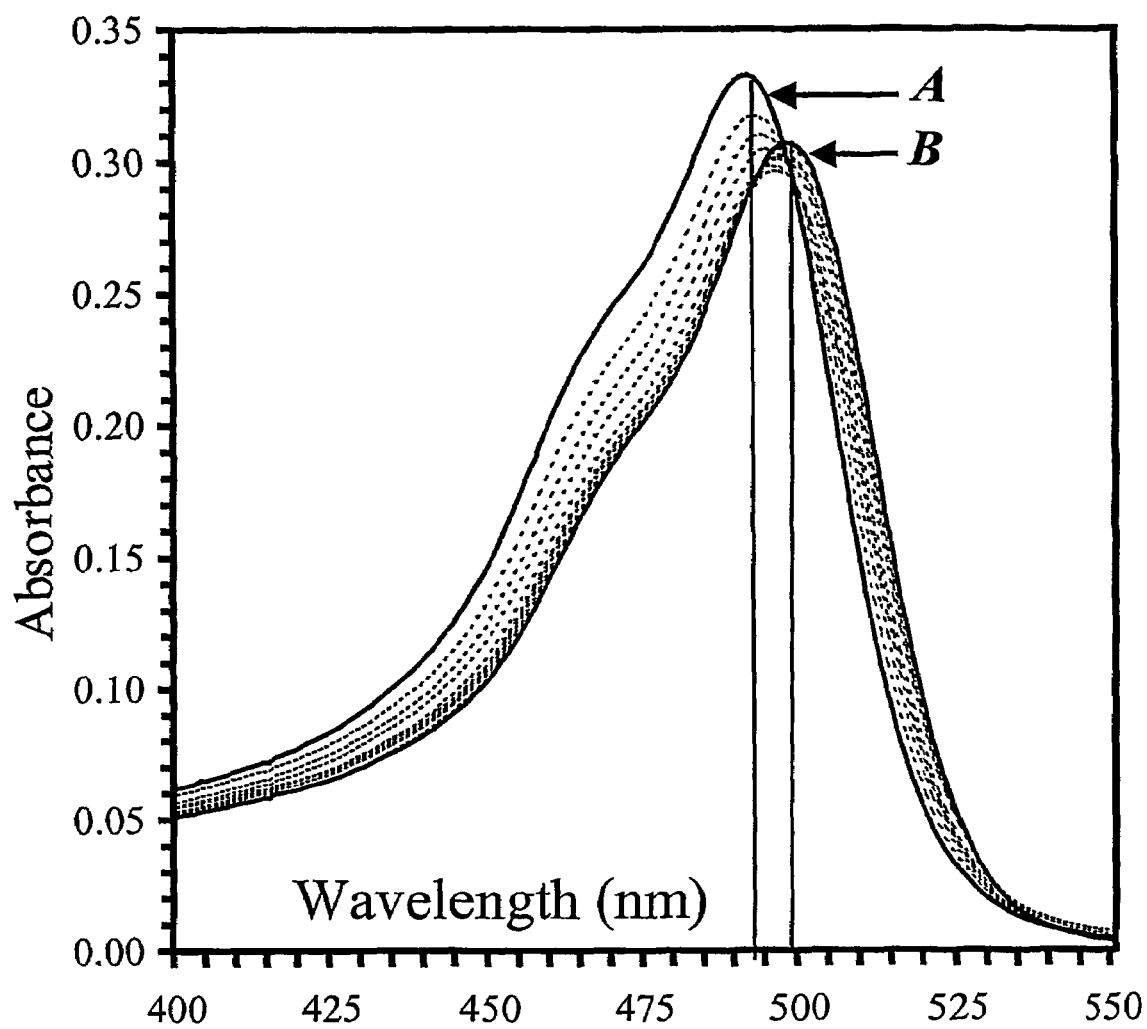
Figures 3, 4:
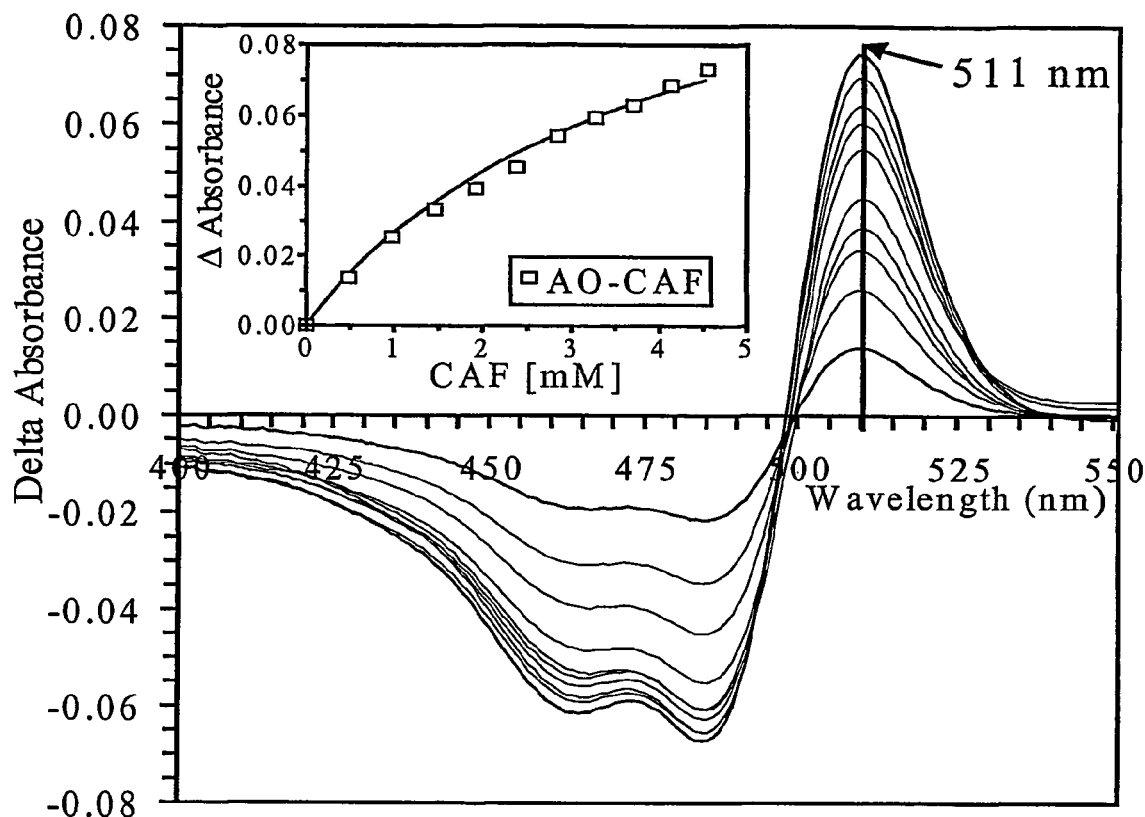

Experiments were conducted to determine whether xanthines with known binding affinities to AO could compete with nuclear DNA for binding to AO and, therefore, be able to remove AO from its intercalation position within nuclear chromatin. Fluorescence microscopy was used to observe the fluorescent color produced by the AO-DNA complex following the staining of chicken erythrocyte nuclear chromatin with AO at both 5 μM and 5 mM. A red fluorescence was observed at higher AO:bp ratios when the amount of AO far exceeds the number of possible intercalation sites. This red fluorescence, is attributed to its electrostatic bonding to the charge groups on the phosphate backbone of the DNA molecule and, fully masks the green fluorescence of the intercalated AO. Alternatively, at low AO:bp ratios when the amount of AO is less than or equal to the number of available intercalation sites, green fluorescence predominantly occurred, characteristic of AO intercalation between purine base pairs on dsDNA (Haugland, 1994). Since the binding affinity for AO intercalation (green fluorescence) is significantly higher than its affinity to form electrostatic bonds (red fluorescence), AO prefers to bind to dsDNA via intercalation, FIG. 4-2 shows two photomicrographs taken of microscope slides smeared with chicken erythrocytes then stained with 10 mM AO at two exposure times to illustrate the differential fluorescence color of nuclear chromatin. Nuclei (top) exposed to the AO solution for 10 minutes then rinsed with water fluoresce red (electrostatic bonding) while nuclei (bottom) exposed to AO for 10 seconds then rinsed with water, fluoresce green (intercalation). A rinse of the slides with 50 mM of CAF for 10 minutes reduced the fluorescence intensity to background level.

Table 4-3 lists the results from the rinsing of chicken erythrocytes with different xanthines having different binding affinities for AO. The two xanthines with the lowest $K_{assoc}$ values had little significant effect on the observed fluorescence produced by the AO stained nuclear chromatin However, as the $K_{assoc}$ value of the xanthine increased to ~256 $M^{-1}$, as seen with CAP, reversibility of AO staining to dsDNA occurred as evidenced by the disappearance of both, green fluorescence in erythrocytes lightly stained with AO (low AO:bp ratio) and, a slight but observable reduction in red fluorescence for erythrocytes highly stained with AO (high AO:bp ratio). Rinses with both, 1,3,7,9-tetramethyl uric acid ($K_{assoc}$ 552 $M^{-1}$) and aminophylline ($K_{assoc}$ 596 $M^{-1}$), resulted in a removal of most, if not all, green and red color as observed under fluorescence microscopy. These results indicate that xanthines with higher $K_{assoc}$ values are more effective in the removal of AO from chicken erythrocyte nuclear chromatin.

TABLE 4-3

Nuclear color observed by fluorescence microscopy after staining chicken erythrocyte nuclear chromatin with acridine orange at either 5 μM or 5 mM, before and after xanthine rinses, and after re-staining with acridine orange.

| COMPOUNDS | | | AO [5 μM] | | | AO [5 mM] | | |
|---|---|---|---|---|---|---|---|---|
| Xanthine Rinse | mM | $K_{assoc}$ ($M^{-1}$) | Stain | After Rinse | Re-stain | Stain | After Rinse | Re-stain |
| Theophylline | 50 | 161 | Green | Green | Green | Red | Red | Red |
| Caffeine | 50 | 256 | Green | None | Green | Red | Red-Green* | Red |
| Tetramethyl uric acid | 50 | 552 | Green | None | Green | Red | None | Red |
| Aminophylline | 50 | 596 | Green | None | Green | Red | None | Red |

*Transitional from red to green fluorescence having a color that appeared greenish yellow.

The invention is not limited to chicken erthrocyte DNA. The application of this invention is not limited to the modified xanthines tested or to the concentrations used This invention is applicable to a wide range of modified xanthines, including, but limited to 1-methyl xanthine, 1,3-dimethyl xanthine, 3,7-dimethyl xanthine, 1,7-dimethyl xanthine, 1,3,7-tri-methyl xanthine, 1,3-dimethyl xanthine, 1,3-dimethyl-8-oxy xanthine, 1,3-dimethyl-8-chloro xanthine, and 1,3,7,9-tetramethyl-8-oxy xanthine. Additionally, the excess amount of xanthines need not be limited to that given in Table 4-2. Variations of Xanthine to intercalator ratio are included within the scope of this invention. In addition, an polynucleotide, whether it is DNA, RNA, or PNA may be used in either a single, double, or higher order stranded structure. Furthermore, the use of the interceptor molecule is not limited to modified xanthines. Any molecule that binds with the DNA intercalator through the law of mass action can be used. Examples include, but are not limited to, purines, pyrimidines, uric acid, porphyrin, polynucleotides, DNA, RNA, PNA, and combinations thereof. In addition, this invention also includes the varying the salt concentration as discussed previously to stabilize the dimer fomation of intercalator molecules.

EXAMPLE 8

This invention can also be applied to staining and/or labeling of DNA. Chicken erythrocytes were used as example system to illustrate the use of labeling of DNA.

Microscope slides smeared with chicken erythrocytes were stained with either 5 μM or 5 mM AO for a period of 30 minutes followed by three 10 second rinses in distilled water before drying at room temperature. Slides were then examined by fluorescence microscopy using a, Zeiss Model 63 Microscope with a xenon source fluorescent emitter. In some instances, a blocking filter was used to filter out fluorescence emission in the red and higher wavelengths. Photomicrographs were taken with Kodak Gold 35 mm ASA 1600 speed film, developed and color prints made. Comparative photomicrographs were taken at the same magnification and at the same exposure time. Selected photomicrographs were digitally scanned (Hewitt-Packard, Model 4L Scanner, Palo Alto, Calif.) and stored on 100 MB ZIP cartridges.

Slides were then exposed to 50 ml solutions of theophylline (50 mM), caffeine (50 mM), 1,3,7,9-tetramethyl uric acid (50 mM), and aminophylline (50 mM) for 1 hour under static conditions, rinsed with distilled water, then, allowed to dry at room temperature. Slides were again examined by fluorescence microscopy and fluorescence color of the nuclei recorded. Slides were again stained with 5 mM AO then re-examined by fluorescence microscopy and fluorescence color of the nuclei recorded.

In the example shown in Table 4-3, the chicken erythrocytes were smeared and dried on a microscope slide prior to exposure to the AO solution for 30 minutes followed by water rinses to remove excess AO. Following drying, each slide was observed under fluorescence microscopy then placed in one of the xanthine solutions (50 ml volume) for 1 hour under static conditions, rinsed with water, then dried prior to being observed by fluorescence microscopy without a red blocking filter. Finally, each slide was restained following the initial staining procedures and again observed by fluorescence microscopy. $K_{assoc}$ values are taken from Table 2-1 and are expressed in $M^{-1}$.

To demonstrate that dsDNA would give the same fluorescent color results as chicken erythrocyte nuclear chromatin, dsDNA in distilled water was placed on microscope slides and was allowed to dry. Additionally this invention can be used to not only inhibit the binding of the intercalator, but to actually remove the intercalator from the DNA using the law of mass action.

In another implementation, giant polytene chromosomes were prepared by the squash technique from the salivary gland of *Drosophila melagaster* larva The salivary gland was placed on a microscope slide, squashed with a glass cover slide, fixed with acidic acid, rinsed with distilled water, and allowed to dry (kindly provided by Linda Chadwell, UTH-SCSA-IBT). Three known DNA intercalators, ethidium bromide (98% purity, Aldrich Chemical Company, Milwaukee, Wis.), doxorubicin (98%, Sigma Chemnical Company, St. Louis, Mo.), and acridine orange plus the minor groove binding DNA stain Hoechst 33258 (98%, ACROS Chemical Company, NJ) were prepared in distilled water at a concentration of 1 mM (for chemical structures see FIG. 4-1, where acridine orange (3,6-bis [dimethylamino] acridine) is shown in Panel A, ethidium bromide is shown in Panel B, doxorubicin is shown in Panel C, Hoechst 33258 is shown in Panel D). The slides with prepared chromosomes were immersed in these stains for a period of 30 minutes, rinsed with distilled water, and dried at room temperature. Fluorescence microscopic analysis was conducted at $\lambda_{ex}$ 360 nm and photomicrographs were conducted on a Zeiss Model 63 Microscope with a xenon source fluorescent emitter. Photomicrographs were taken using Kodak Gold 35 mm ASA 1600 speed film noting the position of one individual chromosome on the slide. The stained slides were then subjected to 100 mM caffeine or 100 mM aminophylline under static conditions for a period of 15 minutes, rinsed with distilled water, then allowed to dry at room temperature. The presence of the same individual unstained chromosome in the field was confirmed by phase contrast microscopy. The chromosome was viewed again under fluorescence microscopy at $\lambda_{em}$ 360 nm, and color recorded. Slides were re-stained by immersion in the 1 mM stain for a period of 30 minutes, rinsed with distilled water, and dried at room temperature, and the same individual chromosome was examined by fluorescence microscopy and the fluorescence color recorded.

Microscope slides (slides) coated with chicken erythrocytes were stained by placing the slide into a 50 ml beaker filled with a 1 mM solution of AO prepared in distilled water for approximately 10 seconds (static) followed by three successive 10 second rinses in distilled water before drying at room temperature. Care was taken to store all slides in the dark when not in use to avoid photobleaching. Stained slides were dried prior to being exposed to 50 ml of a 100 mM solution of either CAF or aminophylline (AM) for set time periods under static conditions. Exposure to the xanthine solution was followed by three 10-second rinses with distilled water and drying of the slides in the dark prior to fluorescence analysis. Control slides consisted of erythrocyte coated slides that were subsequently placed in only distilled water (no stain) prior to drying, blank slides (no erythrocytes) placed in AO staining solutions then dried served as negative controls, and erythrocyte coated cells stained with AO but exposed to only distilled water and not a xanthine solution served as positive control. The stained microscope slides were then attached by tape to a plastic frame (upside down 96-well plate cover) and fluorescence determined using a Perkin-Elmer Model HTS 7000 Bio Assay Reader with $\lambda_{ex}$ 485nm and $\lambda_{em}$ 530 with the gain set at 40. Neither the blank slide exposed to AO nor the erythrocyte smeared slide exposed to distilled water resulted in detectable fluorescence.

These DNA coated slides were then treated in the same xanthine solution washes as the slides coated with chicken erythrocytes. Examination of these DNA coated slides using the same AO staining conditions and xanthine exposure conditions used for the chicken erythrocytes did yield the same color fluorescent microscopy changes seen in the erythrocyte nuclear chromatin. Re-staining of these DNA coated slides with the AO solution following xanthine treatments confirmed that stainable DNA was still present on the slides.

FIG. 4-3 depicts three photomicrographs of the same *Drosophila* polytene chromosome: after staining with the DNA minor groove binder Hoechst 33258 dye (Panel A), after rinsing with CAF for 15 minutes (Panel B), and a phase contrast verification of the presence of the chromosome after the CAF rinse (Panel C). Table 4-4 summarizes the results from the experiments using caffeine (CAF) and aminophylline (AM) to remove the following DNA intercalators: doxorubicin, ethidium bromide, acridine orange, and the DNA minor groove binder Hoechst 33258 from their binding sites within polytene chromosomes. The results demonstrate the ability of CAF or of AM to extract intercalated AO from dsDNA polytene chromosomes. AO appeared to be completely removed with AM washes while exposure to CAF washes did not completely remove the stain from the chromosome under these experimental conditions. Results from tests with the other DNA intercalators show that either aminophylline or caffeine can be used to remove these DNA intercalators from the chromosome bands. Results from tests with the DNA minor groove binder Hoechst 33258 dye demonstrate an apparently complete removal of Hoechst 33258 from the chromosomes with the addition of either CAF or AM. Doxorubicin, known to form a binding complex with caffeine, also appeared to be completely removed from the chromosomes upon exposure to CAF. However, exposure to AM only moderately removed doxorubicin from the chromosome. Finally, using ethidium bromide as the DNA intercalator revealed that AM was less effective in removing the ethidium bromide molecule from the chromosome than was CAF. With all DNA intercalators, the staining of chromosome bands was intense before the xanthine rinses and was again intense following re-staining.

TABLE 4-4

The removal of the DNA intercalators ethidium bromide, doxorubicin, acridine orange, and the DNA minor groove binder Hoechst 33258 from polytene chromosome bands by 15 minute wash treatment with 100 mM aminophylline or with 100 mM caffeine followed by distilled water rinse and drying.

| DNA Intercalator | Staining before Xanthine Exposure | Degree of Stain Removal | | Re-staining following Xanthine Exposure |
| --- | --- | --- | --- | --- |
| | | Exposure to CAF (100 mM) | Exposure to AM (100 mM) | |
| Acridine Orange | Banding | Almost complete | Complete | Complete Banding |
| Ethidium Bromide | Banding | Complete | Almost complete | Complete Banding |
| Doxorubicin | Banding | Complete | Moderate | Complete Banding |
| Hoechst 33258 | Banding | Complete | Complete | Complete Banding |

To verify the observations and results from the experiments using fluorescence microscopy, experiments were conducted to quantify the removal of intercalated AO from DNA with the xanthines caffeine (CAF) and aminophylline (AM), utilizing a fluorescence plate reader. FIG. 4-4 shows the relationship between the length of time of exposure (no mixing or shaking) and the $K_{assoc}$ value of the xanthine on the removal of AO from nuclear chromatin. The example shown in FIG. 4-4 illustrates AO stained (1 mM AQ for 10 sec) chicken erythrocytes smeared slides exposed under static conditions to aqueous solutions of either 100 mM caffeine (CAF) (n=3), of 100 mM aqueous solution of aminophylline (AM) (n=3), or to distilled water for periods of 10 seconds, 10 minutes, one hour, and two hours. Distilled water served as solvent control (n=8). The reduction of fluorescence ($\lambda_{ex}$ 485 nm; $\lambda_{em}$ 530 nm) for AM and CAF followed first order decay kinetics with significant fits to the exponential decay model ($R^2_{CAF}$=0.998, P value (runs test)=0.90; $R^2_{AM}$=0.879, P value (runs test)= 1.00). A plot of the mean fluorescence values percent of control) versus time of exposure to the xanthine containing solution shows a good fit to a first order decay model equation for both CAF ($R^2_{CAF}$=0.998) and AM ($R^2_{AM}$=0.879). By holding the concentration of both xanthines constant, these results indicate that, the removal of AO from nuclear chromatin DNA follows first order decay kinetics and is dependent on time of exposure, as expected by mass action and on the $K_{assoc}$ value of the xanthine.

Lability to acids is a property of DNA. Under mild acid hydrolysis most of the purine bases are very readily removed from the DNA molecule resulting in the formation of a potential aldehyde group in the sites where the purine bases were bound. This liberated potential aldehyde group should react with aldehyde reagent. By using the depurination portion of the Feulgen method to selectively remove the purine bases, the active sites on the DNA polymer available for AO intercalation were removed. The phosphate backbone as well as the pyrimidine bases are left intact and are still able to facilitate electrostatic bonding of the AO molecule to the DNA.

EXAMPLE 9

In another implementation of this invention, by increasing the binding affinity of a modified xanthine with a DNA intercalator, the modified xanthine can be used as an interceptor of DNA intercalators. The use of modified xanthines is not limited to unbound intercalators, but may be applied to intercalators bound to polynucleotides as well. The degree of intercalator removal is related to the ratio of xanthine to intercalator molecules.

The effect of increasing exposure time and of increasing relative xanthine concentration (molecular ratio of xanthine to AO) on the ability of xanthines with increasing $K_{assoc}$ values to block the intercalation of AO into chicken erythrocyte nuclear chromatin, demonstrates that the blocking of AO intercalation into nuclear chromatin, can be controlled, by increasing the molar ratio of xanthine to AO, and further demonstrates that, the xanthines with higher $K_{assoc}$ values require lower molar ratios (xanthine to AO) to have a blocking effect than those with lower $K_{assoc}$ values. The blocking effect of the relative concentration between AO and the xanthines (molar ratio) and their respective $K_{assoc}$ values can be offset by exposure time to dsDNA. This was expected based on the high $K_{assoc}$ value of dsDNA with AO (~4000 $M^{-1}$, Lyles and Cameron, 2000).

By keeping the exposure times and the molar ratio constant, the removal of AO staining of the nuclear chromatin was directly related to the $K_{assoc}$ values of the xanthines. The value of 256 $M^{-1}$ for CAF being at a transition $K_{assoc}$ value under the experimental conditions listed in Table 4-3. The ability of the nuclear chromatin to be re-stained further indicates that the bonding of AO to dsDNA is in dynamic equilibrium and that intercalation of AO into nuclear DNA is reversible.

The quantitative results presented in FIG. 4-4 confirmed the observations with fluorescence microscopy. By holding the molar ratio (concentration) constant, the effect of exposure time was assessed on a quantitative basis. The removal of AO from its intercalation site within nuclear chromatin significantly fit an exponential decay model with an excellent fit with more rapid removal of AO from the nuclear chromatin with AM ($K_{assoc}$ 596 $M^{-1}$) than with CAF ($K_{assoc}$ 256 $M^{-1}$).

These experiments with *Drosophila* salivary gland polytene chromosomes indicate that the bonding of known PAH-DNA intercalators into chromosomal DNA is reversible. The ability of CAF and AM to remove the different PAHs tested demonstrates that CAF and AM can remove PAH intercalators from dsDNA in nuclear chromatin. Xanthines with $K_{assoc}$>150 $M^{-1}$ for AO could intercept the AO molecule in a concentration dependent manner resulting in either the inhibition of intercalation into nuclear chromatin or the removal of AO from nuclear chromatin once intercalated. Bonding of known intercalators to chromosome DNA is reversible. Efficacy of AO removal from chicken erythrocyte nuclear chromatin and *Drosophila* polytene chromosome nuclear chromatin was found to be dependent on: 1) the concentration of the xanthine, 2) the concentration of AO, 3) the $K_{assoc}$ value for the AO-xanthine complex, and 4) the time of exposure to the xanthine.

The results also support a general role of specific methyl substituted xanthines with relatively high $K_{assoc}$ values for DNA intercalators as blockers and scavengers of planar PAH-DNA intercalators from their binding sites in chromatin. Thus selected methyl xanthines may serve as desmutagens. The results also suggest a possible role for interceptor molecules such as CAF in the field of pharmacodynamics, drug delivery, and the lessening of cytotoxic effects caused by certain planar polyaromatic carcinogens and anti-neoplastic drugs.

The interactions of AO with itself and with DNA are probably non-covalent. Accordingly, the xanthine, AO, and dsDNA, are in dynamic equilibrium and, therefore, comply with the law of mass action. Based on this, many polyaromatic mutagens or carcinogens that bind to dsDNA through intercalation may be able to bind with a specific xanthine and thus can be blocked from intercalation into dsDNA or removed once intercalated into dsDNA.

The application of this invention is not limited to the modified xanthines tested or to the concentrations used. This invention is applicable to a wide range of modified xanthines, including, but limited to 1-methyl xanthine, 1,3-dimethyl xanthine, 3,7-dimethyl xanthine, 1,7-dimethyl xanthine, 1,3,7-tri-methyl xanthine, 1,3-dimethyl xanthine, 1,3-dimethyl-8-oxy xanthine, 1,3-dimethyl-8-chloro xanthine, and 1,3,7,9-tetramethyl-8-oxy xanthine. Additionally, the excess amount of xanthines need not be limited to that given in Table 4-2. Variations of the ratio of xanthine to intercalator are included within the scope of this invention. In addition, an polynucleotide, whether it is DNA, RNA, or PNA may be used in either a single, double, or higher order stranded structure. Furthermore, the use of the interceptor molecule is not limited to modified xanthines. Any molecule that binds with the DNA intercalator through the law of mass action can be used. Examples include, but are not limited to, purines, pyrimidines, uric acid, porphyrin, polynucleotides, DNA, RNA, PNA, and combinations thereof. In addition, this invention also includes the varying the salt concentration as discussed previously to stabilize the dimer fomation of intercalator molecules.

EXAMPLE 10

The invention is applicable to to targeting other DNA intercalators. For example, the CAF-AO model could be used to design planar interceptor molecules to complex with specific DNA intercalators. An example would be to design an interceptor molecule to complex with planar aflatoxin molecules, a class of potent DNA intercalator carcinogens that contaminate many seeds and grains. Aflatoxins are known to intercalate into dsDNA at specific sites and are a leading cause of liver cancer in third world countries. The ability to selectively complex these molecules, either as a wash to remove the molecules from foodstuffs or as a treatment for accidental ingestion, could significantly reduce their hazardous impact. Thus, another implementation of the invention is to remove intercalating molecules that enter into a patient; entry could be through mouth, nose, eye, ear, skin, lung, or anus of a patient.

According to one embodiment of the invention, xanthines or other complexing agents may be used to remove aflatoxins from foodstuffs. An aqueous solution of a methyl substituted xanthine containing by weight 3% of the complexing agent can be applied to seeds and grains contaminated with aflatoxins from the fungus *Aspergillis niger*, such that the exposure to the complexing agent significantly reduces the amount of aflatoxin contamination rendering the seed or grain non-toxic. The method is not limited to aflatoxins, but may be applied to, including but not limited to nucleotides, porphorins, xanthines, purines, uric acids, alone or together, as monomers or polymers.

EXAMPLE 11

The cytotoxic side affects of doxorubicin as well as other anti-neoplastic medicinals are well documented. The design and use of an interceptor molecule to remove doxorubicin from the blood stream and from non-neoplastic cells could be of benefit to patients suffering from extreme side affects from the repeated use of doxorubicin and other anti-cancer drugs. Additionally, continued exposure to doxorubicin causes myocardial toxicity. Therefore, the ability to remove doxorubicin from myocardial muscle cells through complexation with an interceptor molecule could greatly decrease this hazardous side effect. The ability to remove or reduce intercellular concentrations of these drugs following successful anti-cancer therapy may significantly reduce the continued toxicity to other non-neoplastic cells.

Figures 3, 4, 5, 6:
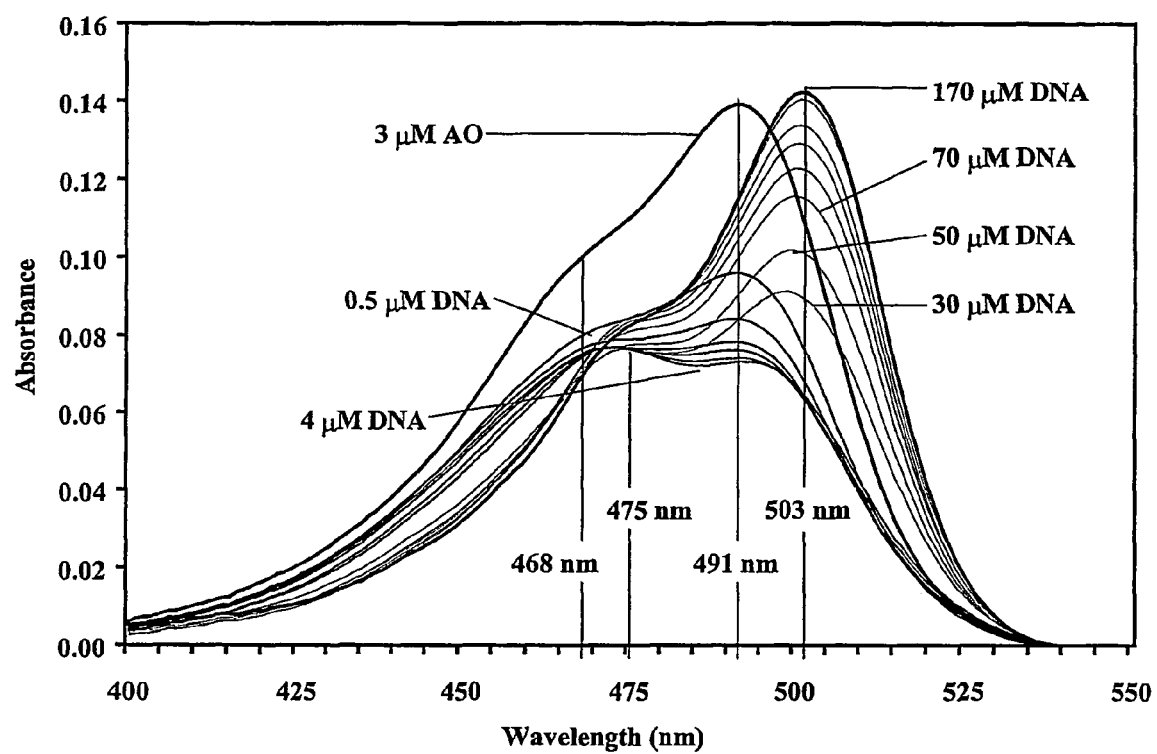
Figures 3, 4, 5, 6, 7:
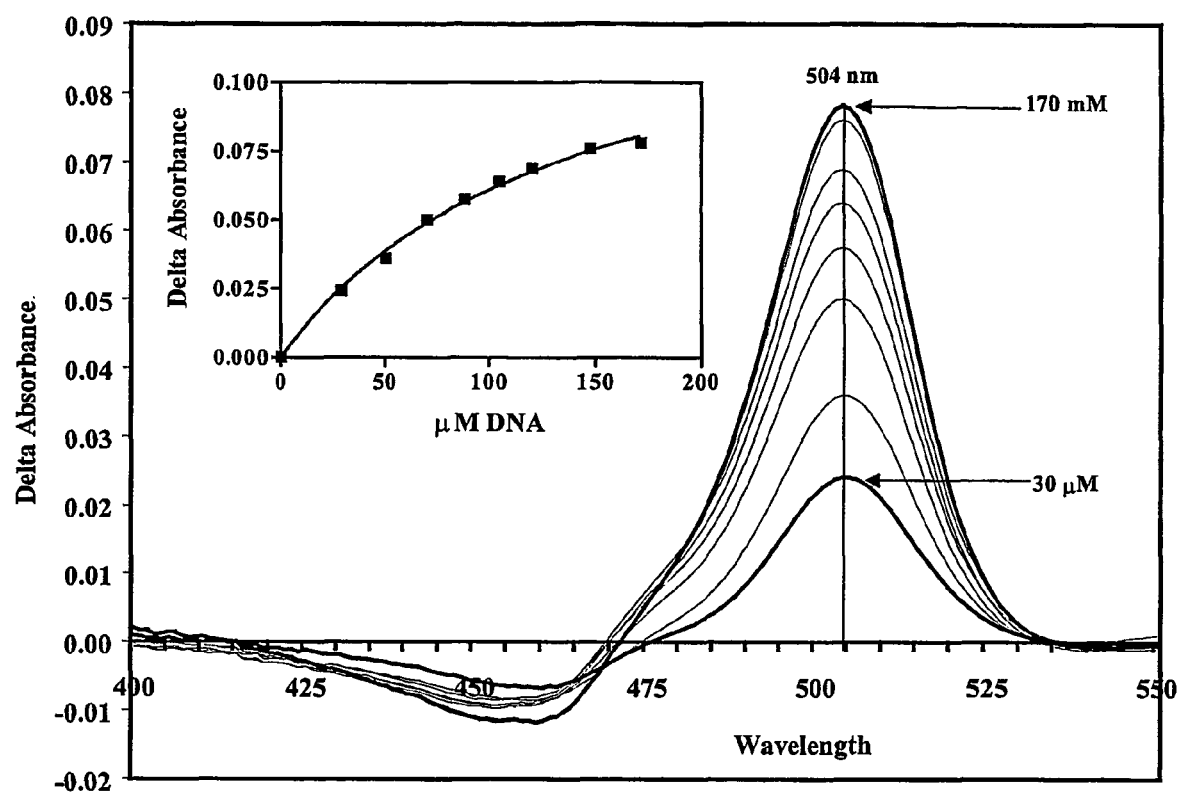
Figures 3, 4, 5, 6, 7, 8:
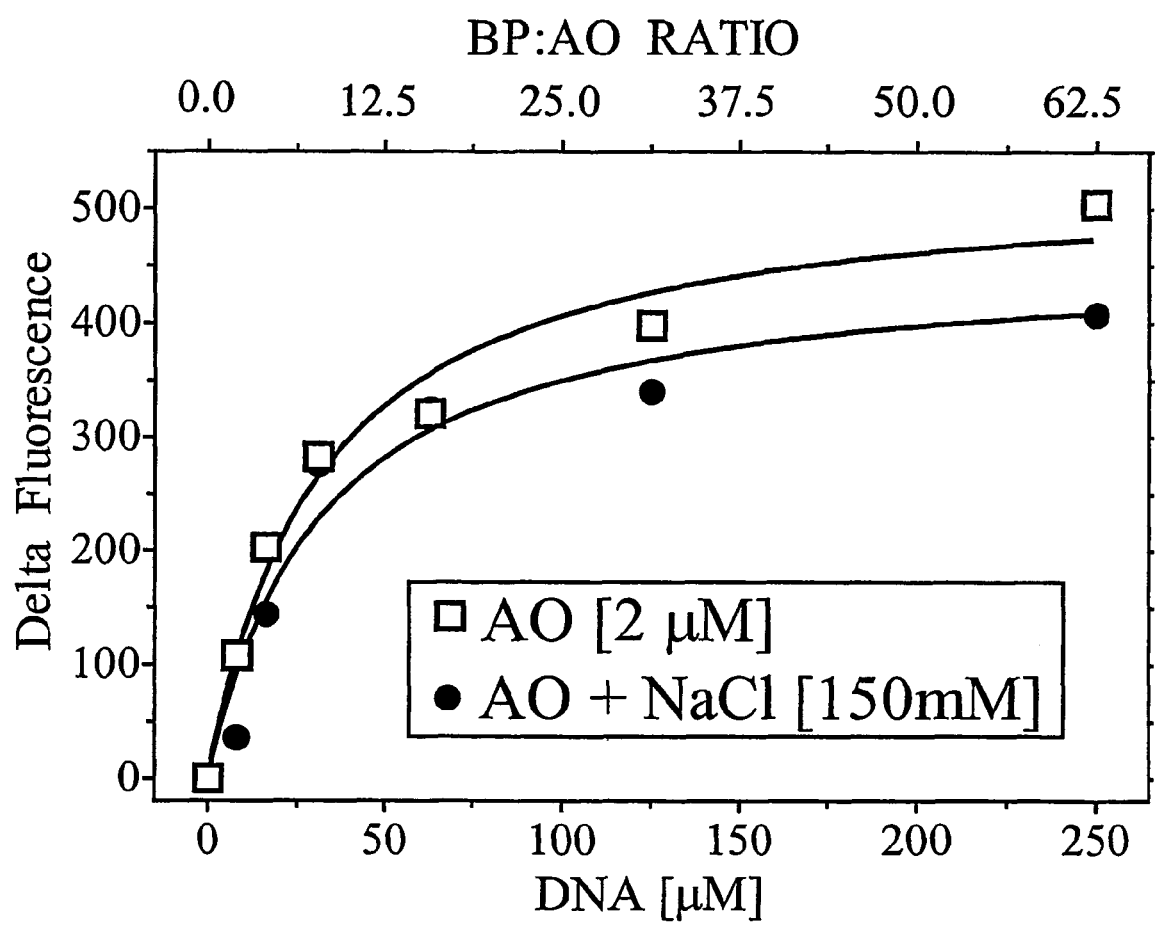
Figures 3, 4, 5, 6, 7, 8, 9:
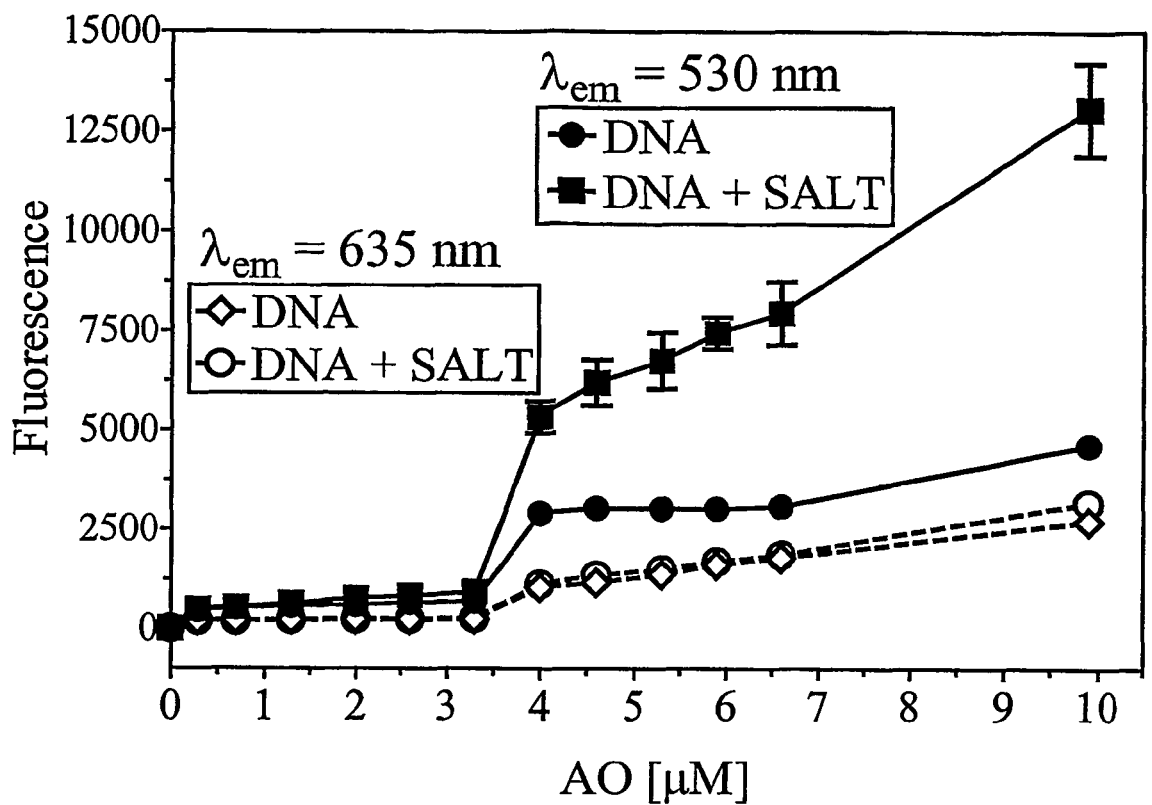
Figures 3, 4, 5, 6, 7, 8, 9, 10:
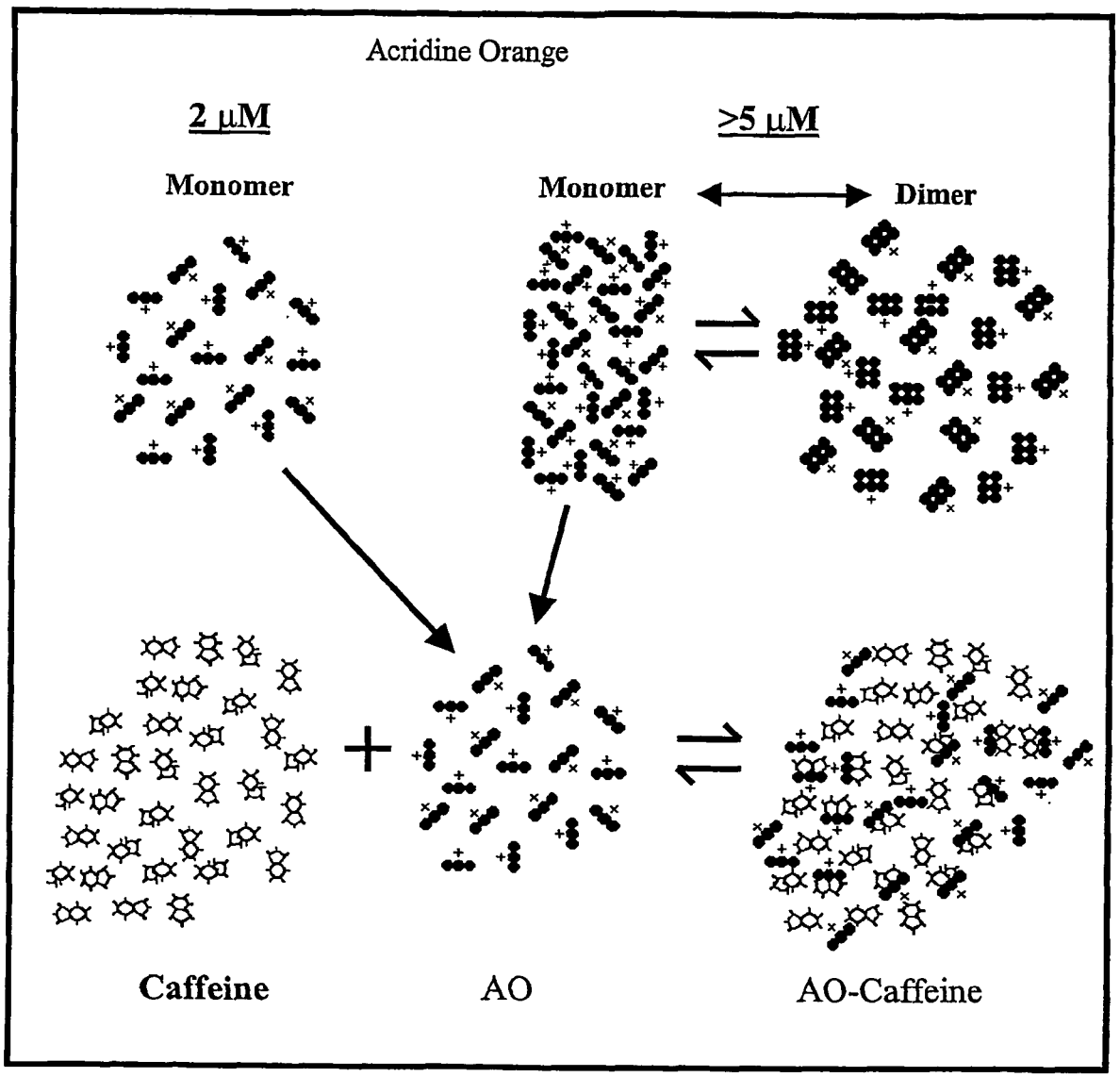
Figures 2, 4:
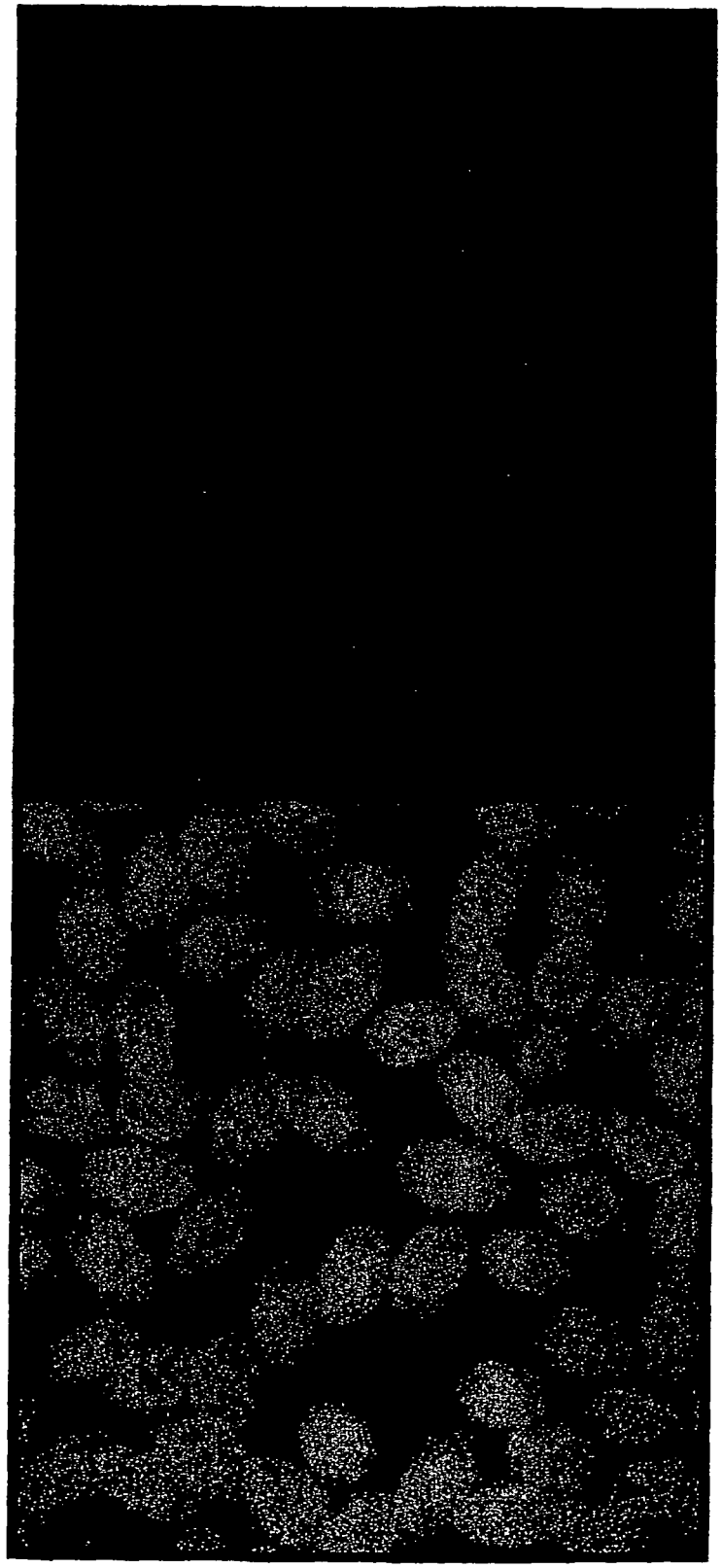
Figures 3, 4:
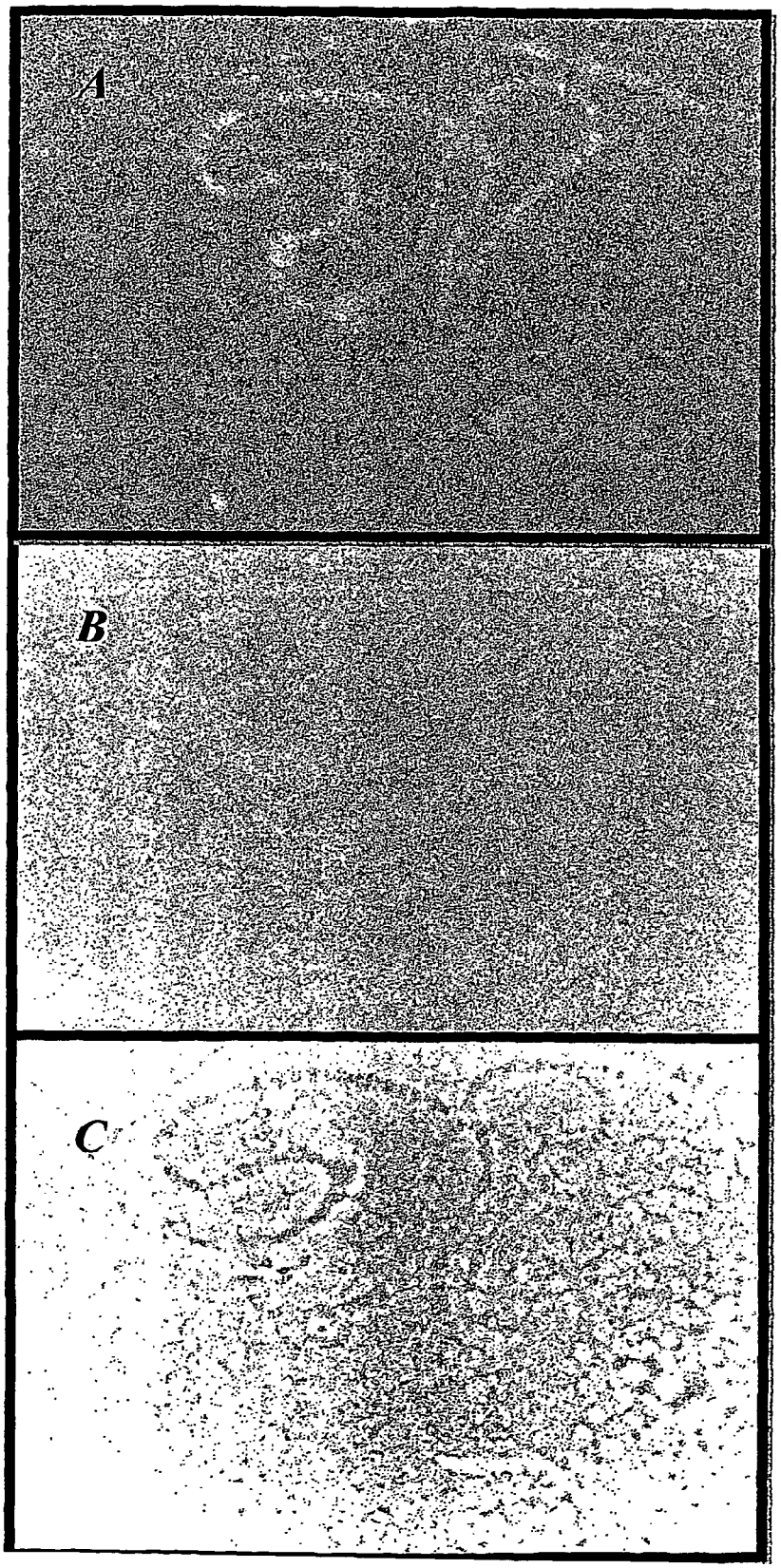
Figure 4:
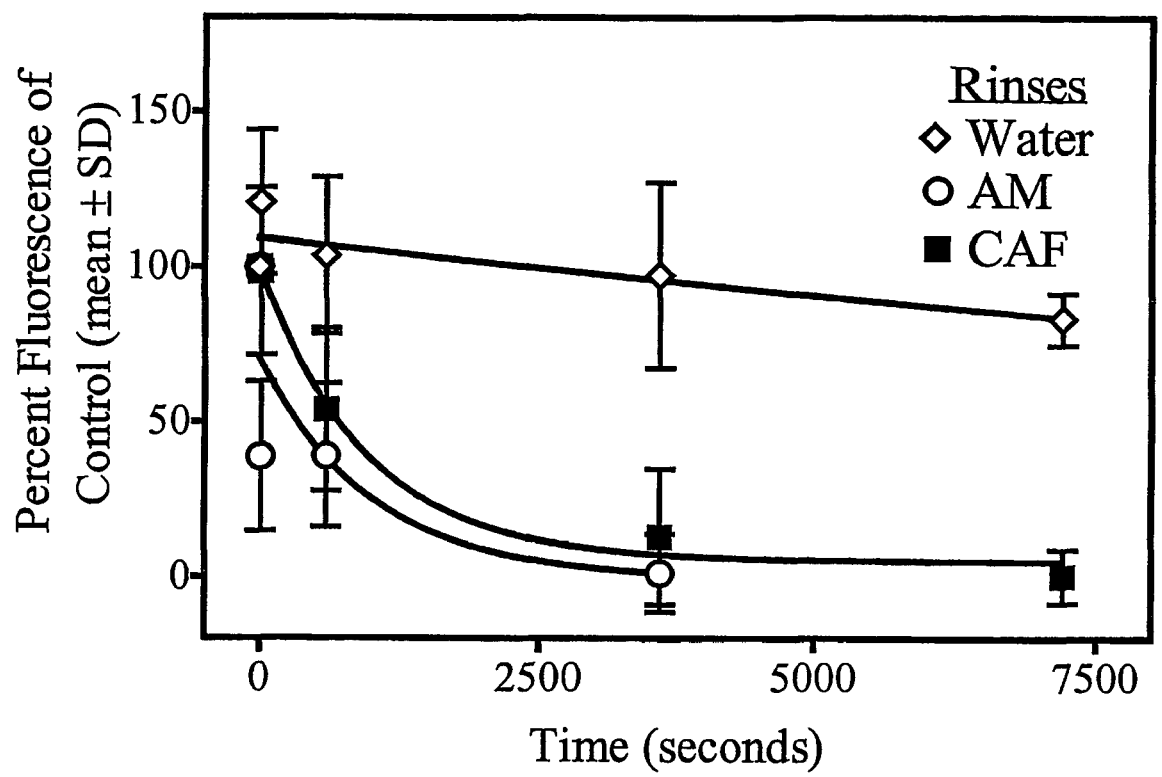
Figures 1, 5:
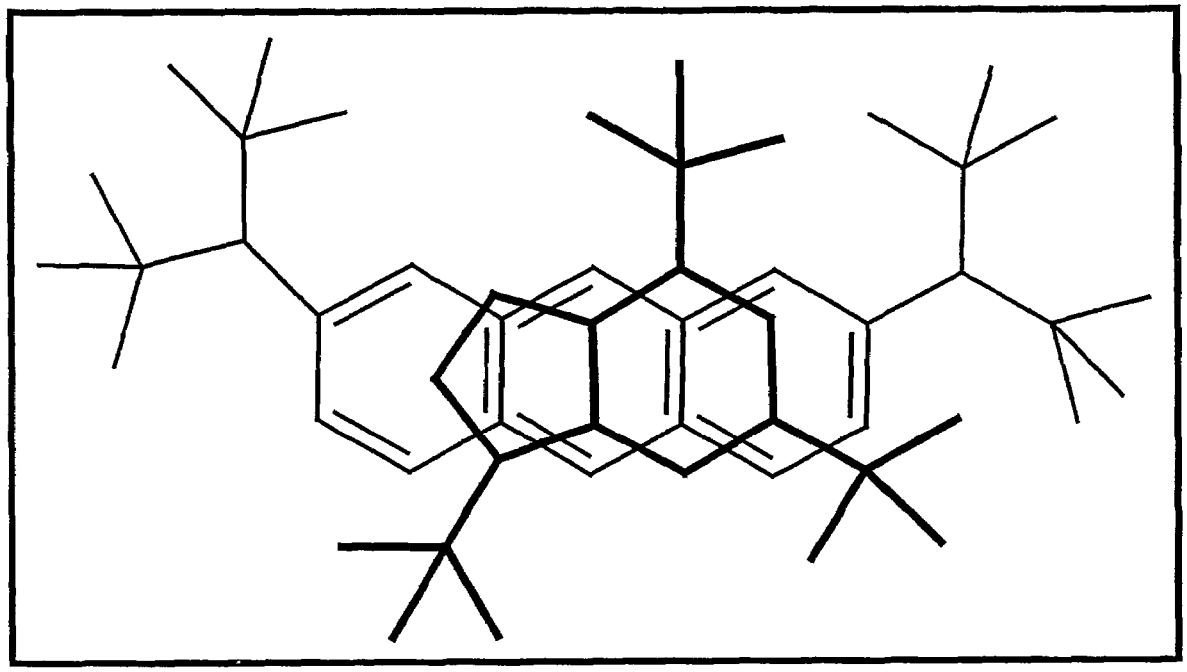
Figures 3, 5:
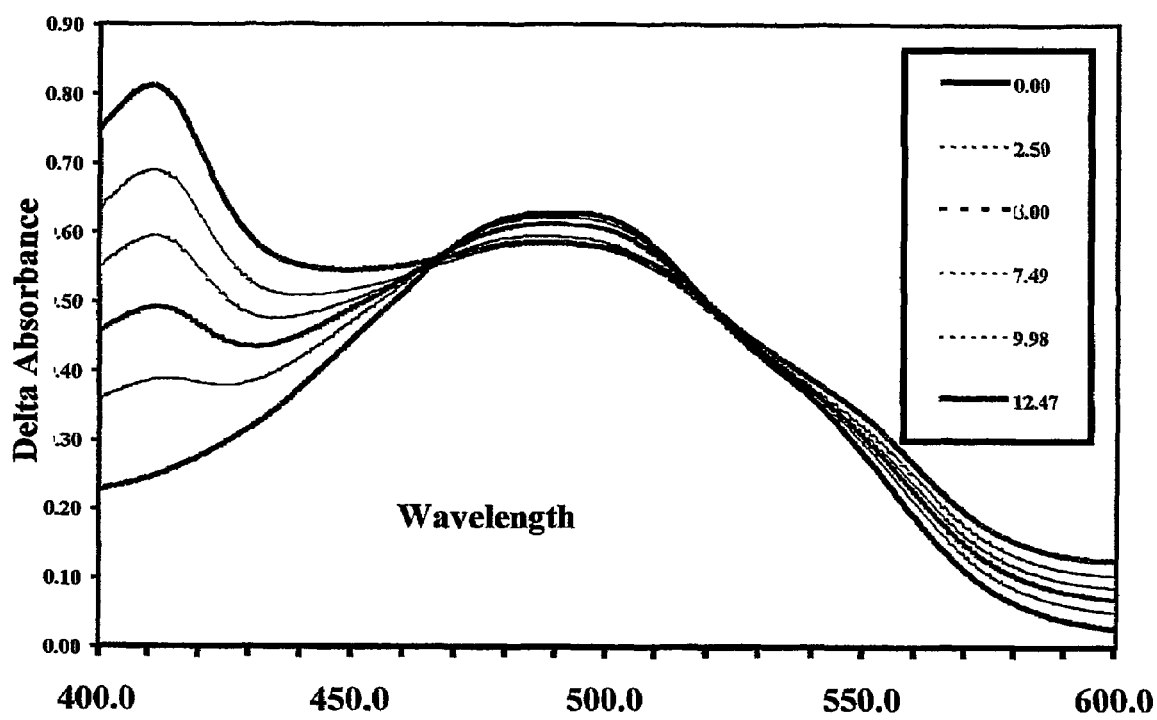

An embodiment shown in FIG. 5-2 illustrates that caffeine binds with doxorubicin. FIG. 5-2 illustrates the absorbance binding spectra of 10 µM doxorubicin titrated with increasing concentration of caffeine. Accordingly caffeine binds with doxorubin. In another implementation, doxorubicin can be bound to chlorophyllin as shown in FIG. 5-3. The selected spectra in FIG. 5-3 denote important transitions within the titration series. Prevalent peaks occur at $\lambda_{abs}$ of 475 nm and 500 nm. These peaks correspond to the prevalent absorbance peaks found at concentrations of doxorubicin at 10 µM and higher concentrations. The absorbance denotes a definitive red-shift in absorbance indicating complexation occurring. The invention is not limited to caffeine or, chlorophyllin, but includes, and is not limited to, other xanthines and porphyrins.

EXAMPLE 12

The use of selected xanthines as carrier molecules, to not only increase the aqueous solubility of many anti-neoplastic medicinals but also as a facilitator for increased intracellular concentrations of this molecule, is a novel idea. A good example of a potential anti-neoplastic drug that could benefit from such a carrier would be paxitaxol, which has a very low solubility in water and, therefore, tends to attach to plastic tubing and to self-precipitate out of solution. The complexation of an interceptor molecule with this planar drug would change the aqueous solubility of the drug as well as its transport kinetics. Theoretically, this would increase the intercellular concentrations of the drug while having no interference with the anti-cancer drug's ability to bind to the DNA within the cell. This is due to the fact that, the carrier molecule-drug complex is in dynamic equilibrium and, therefore, the drug would be available for intercalation into the DNA based on the difference in $K_{\alpha\circ\circ\circ\chi}$ values between the drug and the carrier molecule and the drug and DNA.

This delivery system can be used for topical, oral, interperitoneal, or intravenous delivery of bioactive agents, specifically, anti-neoplastic agents, to tissues, eukaryotic cells, or prokaryotic cells, or yeasts, or fugi. The carrier may consist of a polymer of purines and/or pyrimidines, and/or xanthines and/or uric acids singularly or in combination with modifications of all or one. The carrier can be single stranded, double stranded or can contain multiple strands, loops, cross-links or other such modifications that may alter the secondary, tertiary, quaternary structure of the carrier. The carrier may contain R-group substitutions around the purine, pyrimidine, xanthine, or uric acid base structure. R-group substitutions may be rendered at the N-1, N-3, N-7, N-9 positions and may involve electron donating, electron withdrawing, electronegative, electropositive, hydrophilic, hydrophobic, organic or inorganic chemical groups. Additionally, substitutions can occur at the C-2, C-4, or C-8 positions.

In another example, monomers or polymers of purines, pyrimidines, xanthines, or uric acid may be used for delivery of insoluble bioactive agents to cells or solubilization of bioactive agents using DNA or DNA-like compounds.

Antineoplastic drugs are known to be useful for the treatment of various cancers. A typical property of antineoplastic drugs is their low solubility in water. This property leads to difficulties when creating formulations suitable for administration to humans or other animal patients. Commonly, low concentrations, detergents, oils, liposomes, or other means of solubilization are used.

Taxol (paclitaxel) is supplied by Bristol-Myers Squibb Company as a mixture in Cremophor EL (polyethylated castor oil) and dehydrated alcohol. For every 6 mg of paclitaxel, 527 mg of oil and 49.7% alcohol is used. Vials are supplied as 30 mg in 5 mL, 100 mg in 16.7 mL, and 300 mg in 50 mL liquid (all 6 mg/mL).

Navelbine (vinorelbine tartrate) is used as a single agent or in combination with cisplatin for the first-line treatment of ambulatory patients with unresectable, advanced non-small cell lung cancer. It is supplied by Glaxo Wellcome at 10 mg/mL in water without preservatives or additives.

Ideally, a method for the solubilization of antineoplastic drugs would be available which results in high solubility without the introduction of exogenous, non-native materials to the patient. Thus, there exists a need for novel administration methods for antineoplastic drugs.

Nucleic acids have been found to be an effective carrier agent for the delivery of antiheoplastic agents to patients. The nucleic acid-antineoplastic agent composition improves the solubility and clinical application of typically water insoluble drugs.

Nucleic acids have been found to be an effective carrier agent to aid in the delivery of antineoplastic agents to a patient. A composition is formed comprising one or more antineoplastic agents and nucleic acids. The composition is then administered to the patient. As the nucleic acids are degraded in the patient, the antineoplastic agent becomes more available.

Generally, any antineoplastic agent may be used in connection with this invention. Particularly attractive are antineoplastic agents which bind to nucleic acids, and which have low or negligible solubility in water. In such a situation, the nucleic acids can serve as solubilzing agents. The resulting compositions can have a higher concentration of antineoplastic agents than would a similar composition lacking nucleic acids. Examples of antineoplastic agents include TAXOL (paclitaxel, TAXOL is a registered trademark of Bristol-Myers Squibb Company), 5-FU (5-fluorouracil), ADRIAMYCIN (doxorubicin hydrochloride, ADRIAMYCIN is a registered trademark of Pharmacia & Upjohn), Cytoxan (cyclophosphamide), Mexate (methotrexate), NOVANTRONE (mitoxantrone, NOVANTRONE is a registered trademark of Immunex Corporation), NAVELBINE (vinorelbine tartrate, NAVELBINE is a registered trademark of), and TAXOTERE (docetaxel, TAXOTERE is a registered trademark of Aventis Pharmaceuticals). Additional chemotherapy drugs include Actinomycin D, Altretamine, Asparaginase, Bleomycin, Busulphan, Capecitabine, Carboplatin, Carmustine, Chlorambucil, Cisplatin, Cytarabine, Dacarbazine, Daunorubicin, Doxorubicin, Epirubicin, Etoposide, Fludarabine, Gemeitabine, Hydroxyurea, Idarubicin, Ifosfamide, Irinotecan, Liposomal Doxorubicin, Lomustine, Melphalan, Mercaptopurine, Mitomycin, Oxaliplatin, Procarbazine, Streptozocin, Tamozolomide, Thioguanine, Thiotepa, Tomudex, Topotecan, Treosulfan, Vinblastine, Vincristine, Vindesine. and Vinorelbine. Although most of these compounds are soluble in water to some extent, the addition of DNA significantly enhances the solubility and structural stability of the bioactive agent or rug whether bound via intercalation or electrostatic attraction or both.

While described in the context of antineoplastic agents, nucleic acids can be used to improve the solubility of any low water solubility drug which binds to or complexes with nucleic acids.

The nucleic acids can generally be any nucleic acid. The nucleic acid can be DNA, RNA, PNA, or other synthetic nucleic acids. Preferably, the nucleic acids are DNA. The nucleic acids can be single or double stranded, and preferably are double stranded. The nucleic acids can generally be of any size. The nucleic acids can be at least about 4 bp (or bases), 8 bp, 10 bp, 12 bp, 14 bp, 16 bp, 18 bp, 20 bp, 30 bp, 50 bp, 100 bp, 200 bp, 500 bp, 1 kb, 2 kb, 3 kb, 4 kb, 5 kb, 6 kb, 7 kb, 8 kb, 9 kb, 10 kb, 20 kb, 30 kb, 40 kb, 50 kb, 1 mb, or multiple mb. Longer nucleic acids may be desired for their increased stability, while shorter nucleic acids may be desired for their ease of preparation and degradation in the patient. The nucleic acids may be chemically modified. The nucleic acids may be a mixture of an array of sizes, e.g. nucleic acids isolated from a natural source such as salmon testes or calf thymus.

The composition may comprise other materials such as buffers, flavorings, sugars, drugs, glycerol, stabilizers, antioxidants, or any other pharmaceutically acceptable materials.

The solubility of the antineoplastic agent in the inventive composition is preferably at least about 2 times, 3 times, 4 times, 5 times, 6 times, 7 times, 8 times, 9 times, 10 times, 20 times, 30 times, 40 times, 50 times, 100 times, 200 times, 300 times, 400 times, 500 times, or 1000 times that in the same composition lacking the nucleic acid.

The patient may be a mammal, bird, fish, or amphibian. The mammal can be a human, dog, cat, rabbit, hamster, ferret, horse, cow, pig, or goat Preferably, the mammal is a human.

The antineoplastic agent—nucleic acid composition can be administered to the patient in any pharmaceutically or medically acceptable method. For example, the composition can be delivered orally, topically, transdermally, by IV, by inhalation, by IP injection, by IM injection, by electroporation, or by liposomes.

As an example, the anti-neoplastic agent Doxorubicin or pasitaxol is dissolved in a primarily aqueous I.V. solution containing an oligonucleotides consisting of 10 mers with 1:1 molar ratio or more specifically an amount equal to or exceeding 50% of the binding curve; whereas the oligonucleotides is poly adenosine-thymidine in a double helix.

The law of mass action can be exploited to determine the required concentrations of interceptor or carrier compound according to the following equations:

$$[X] = K_{assoc}[Y]/(1 + K_{assoc}[Y]) \quad \text{Equation I:}$$

OR $$[Z] = K_{assoc}[X]/(1 + K_{assoc}[X]) * 100. \quad \text{Equation II:}$$

Here $K_{assoc}$ is the binding affinity of the interceptor or complexing agent for the compound or bioactive agent to be complexed; [X] is xthe concentration or amount of active sites of the interceptor or complexing agent; [Y] is the concentration or amount of active sites of the agent to be complexed; and [Z] is the percent of the binding curve from no binding to infinite or complete binding. Preferably [Z] should have a value between 0.1 and 99, and more preferably [Z] should be between 40 and 99, and even more preferrably [Z] should be equal to or greater than 50. Ideally, the concentration of the complexing or binding agent should approach saturation of the binding curve to the greatest extent possible considering the solubility of the binding agent and the toxicity of said agent.

In another embodiment of the invention other molecules can be used as a carrier. For example xanthines and chlorophyllin have been shown to exhibit a binding affinity for doxoribucin as illustrated in Example 12.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 13

The the use of specialized xanthines to complex with these PAHs prior to human exposure, offers benefits as a preventive modality. For example, the potential hazardous effects from environmental exposure to PAHs, such as benzo(a)pyrene and dimethyl benzanthracene, could be significantly decreased if the PAHs were first exposed to a xanthine with a high $K_{assoc}$ value for that particular PAH. For example, professional chimney sweeps, who are occupationally exposed to a variety of carcinogen PAHs, would be able to significantly reduce their risk of exposure to these carcinogens. The addition of selected xanthines to the walls of the chimney prior to cleaning could reduce the biological hazards from exposure to these PAHs. Additionally, many occupations that risk exposure to planar carcinogens could benefit for either a preventive treatment prior to exposure or a therapeutic treatment following accidental exposure.

In one embodiment a solution containing an effective amount of complexing or binding agent or agents may be applied to the skin of a person. The solution may be in a liquid or a gel. For example, a 3% solution of dsDNA would be applied to the skin of chimney sweepers to prevent exposure to bioactive agents and carcinogens; or is applied post-exposure as a treatment for the prevention of skin cancer.

In one implementation a modified xanthine or porphyrin may be used as an interceptor of PAHs. The interceptor need only be delivered to DNA region that has bound with the PAH in the patient Once the interceptor is delivered to the intercalator molecule in a molar excess, the law of mass action will drive the reaction such that the binding of the intercalator to the DNA will be reduced.

EXAMPLE 14

A cigarette filtering material consisting of a DNA coating would be a good vehicle to remove PAHs in both primary and secondary smoke. A cigarette filter containing an active DNA surface could extract not only polyaromatic hydrocarbons, but also other toxic compounds known to interact with DNA. In one implementation of this invention, a cigarette filter would be comprised of dsDNA material. As the smoke passes through the DNA in the filter, the PAHs, among others, would bind to the DNA.

EXAMPLE 15

Another implementation of this invention is a method for removing bound intercalated dyes from DNA. Many intercalators, such as AO, have a fluorescent tag that can be used for detecting the intercalator bound to the DNA. The addition of one or more specific dyes or compounds to the compound of choice (e.g. RNA, DNA, dsDNA, or similar molecules) that has a specific bining affinity $K_{assoc}$ for that substrate. Once bound to the substrate, a solution containing one or more compounds with a known binding affinity or $K_{assoc}$ for the dye is added to the substrate in either static or dynamic suspension, washing, rinsing, or other means whereby the binding compound can remove, extract, or mask the dye or compound in a manner following the law of mass action and relating to the $K_{assoc}$ between the extracting compound and the compound to be extracted, the molar ratios between general and specific binding affinities and/or $K_{assoc}$ ranges may be determined and specific and/or general eterminations may be made concerning active sites, genetic makeup, chemical composition, secondary, tertiary, and quaternary structure as well as a variety of other issues.

The interceptor molecule may be chosen from, among others, purines, xanthines, pyrimidines, uric acid, porphyrins, and polynucleotides, and polymers and mixtures thereof. The polynucleotides are preferably double stranded DNA. The concentration of DNA in the medium should be between 0.001% and 10% (wt/wt).

EXAMPLE 16

Another embodiment of the invention is a screening or diagnostic device. In diagnostic or screening studies the interceptor or complexing molecules may be chemically or physically placed in a gel or other solid state form so as to immobilize them to preferentially extract biologically active compounds with significant binding affinities such that the flow of either solutions or gases containing the bioactive agent or agents of choice can be concentrated or extracted from said medium.

Additionally, once complexed in a stationary or static form, selected bioactive agents can be preferentially extracted based on binding affinity by further exposure to solutions or gases containing an effective amount of complexing agent or agents to remove said bioactive agents from the static or solid state system in a $K_{assoc}$—concentration dependent manner.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention.

I claim:

1. A composition for delivery of an anti-neoplastic agent to a patient, the composition comprising:
    an antinoeoplastic agent, and
    a carrier molecule comprising one or more monomers selected from the group consisting of xanthines, uric acid, and mixtures thereof.

2. The composition of claim 1 wherein the carrier molecule R-group substitutions around the xanthine, or uric acid.

3. The composition of claim 2 wherein the carrier molecule is a xanthine having R-group substitution at the N1, N3, N7, or N9 position.

4. The composition of claim 2 wherein the substitution is selected from the group consisting of electronegative, electropositive, hydrophobic, and hydrophilic R-group substitution.

5. The composition of claim 1 wherein antineoplastic agent is selected from the group consisting of paclitaxel, 5-fluorouacil, doxorubicin, doxorubicin hydrochloride, cyclophosphamide, methtrexate, mitoxantrone, and taxotere.

6. A method for the efficient delivery of an antineoplastic agent to a patient, the method comprising:
   obtaining a mixture comprising an antineoplastic agent and a carrier molecule, said carrier molecule comprising one or more monomers selected from the group consisting of xanthines, uric acid, and mixture thereof; and
   delivering the composition to the patient.

7. The method of claim 6 wherein the antineoplastic agent is selected from the group consisting of paclitaxel, 5-fluorouracil, doxorubicin, doxorubicin hydrochloride, cyclophosphamide, methotrexate, mitoxantrone, and taxotere.

8. The method of claim 6 wherein the patient is a mammal, bird, fish, amphibian yeast, bacteria nematode, fungi, or fruit fly.

9. The method of claim 8 wherein the patient is a mammal and is human.

10. The method of claim 8 wherein the patient is a mammal and is selected from the group consisting of a mouse, rat, monkey, dog, cat, rabbit, hamster, ferret, horse, cow, pig, and goat.

11. The method of claim 6 wherein the delivering step comprises oral administration, topical administration, transdermal administration, IV administration IP administration IM administration, by electroporation, inhalation, or by liposomes.

* * * * *